US007706915B2

(12) United States Patent
Mohapatra et al.

(10) Patent No.: US 7,706,915 B2
(45) Date of Patent: Apr. 27, 2010

(54) SYSTEM AND SOFTWARE OF ENHANCED PHARMACY SERVICES AND RELATED METHODS

(75) Inventors: Om Mohapatra, Dhahran (SA); Rao Arimilli, Dhahran (SA); Masood U. Farooki, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 11/173,354

(22) Filed: Jul. 1, 2005

(65) Prior Publication Data
US 2006/0149416 A1 Jul. 6, 2006

Related U.S. Application Data

(63) Continuation of application No. 11/003,264, filed on Dec. 3, 2004, now abandoned.

(51) Int. Cl.
*G06F 17/00* (2006.01)
(52) U.S. Cl. .................. 700/231; 700/232; 700/236; 700/241; 700/242; 700/2; 702/2
(58) Field of Classification Search .............. 705/2–4; 700/231–244
See application file for complete search history.

(56) References Cited

U.S. PATENT DOCUMENTS

| 4,847,764 A | 7/1989 | Halvorson |
| 6,175,779 B1 | 1/2001 | Barrett |
| 2002/0111829 A1 * | 8/2002 | Robibero ................ 705/3 |
| 2003/0055531 A1 * | 3/2003 | Liff et al. .............. 700/235 |
| 2003/0099158 A1 * | 5/2003 | De la Huerga ........... 368/10 |
| 2003/0191670 A1 * | 10/2003 | Hatcher et al. ............ 705/2 |
| 2004/0078220 A1 | 4/2004 | Jackson |
| 2004/0143459 A1 | 7/2004 | Engleson et al. |

FOREIGN PATENT DOCUMENTS

WO WO 99/15990 4/1999

OTHER PUBLICATIONS

Pyxis Envoy Automated Point-of-Use Packaging and Dispensing System, found at www.pyxis.com/products/altenvoy.asp.
Web page article titled AHFS Framework found at www.firstdatabank.com/integrated content/ahfs.

* cited by examiner

*Primary Examiner*—Jeffrey A Shapiro
(74) *Attorney, Agent, or Firm*—Bracewell & Giuliani LLP

(57) ABSTRACT

A system, software, and methods related to enhanced pharmaceutical order entry and administration by medical personnel, and enhanced pharmaceutical inventory control within a medical institution are provided. An embodiment of the system includes a pharmaceutical information management server having memory and a medication administration program product including a set of instructions stored in the memory of the pharmaceutical information management server to enhance provision of pharmacy services. The system also includes medical institution physician computers to provide for computerized physician medication order entry, pharmacy computers to provide for review and verification by a pharmacist of electronic medication orders placed through the physician computers, and medical institution nursing unit computers, to provide for review of and input to electronic medication administration records.

38 Claims, 28 Drawing Sheets

FIG. 11.

| Change Management | | |
|---|---|---|
| # | Title | Functional Area |
| | PRIMARY ITEMS | |
| 1 | Formulary | Formulary & other Master Data |
| 2 | Computerized Physician Order Entry (CPOE) | Order Entry and Management |
| 3 | Single patient medication profile | Order Entry and Management |
| 4 | EMAR and charting | Medication Administration |
| 5 | EMAR posting | Medication Administration |
| 6 | EMAR and inventory management | Medication Administration; Inventory Management |
| 7 | ADDD EMAR functionality | Medication Administration |
| 8 | Ad hoc clinical checking | Clinical & Non Clinical Checking and Drug Information |
| 9 | Drug information | Clinical & Non Clinical Checking and Drug Information |
| 10 | Label re-printing | Label Printing |
| 11 | Bar-coding | Label Printing |
| 12 | Implementation considerations | ALL |
| | SECONDARY ITEMS | |
| 1 | CPOE-agent order entry | Order Entry and Management |
| 2 | Advance filling of outpatient orders | Order Entry and Management |
| 3 | Clinical checking during order entry | Clinical & Non Clinical Checking and Drug Information |
| 4 | Non-clinical checking | Clinical & Non Clinical Checking and Drug Information |
| 5 | Medication orders from Dental clinics | Order Entry and Management |
| 6 | Clinical workstation | ALL |
| 7 | Work queue management | Order Entry and Management; Medication Administration |
| 8 | Notifications on changed and new orders | Order Entry and Management |
| 9 | Label maintenance | Label Printing |
| 10 | Ad hoc reporting | Reporting |
| 11 | Policies and Procedures | ALL |
| 12 | Training | ALL |

*FIG. 25.*

SYSTEM AND SOFTWARE OF ENHANCED PHARMACY SERVICES AND RELATED METHODS

RELATED APPLICATIONS

This is a Continuation Patent Application which claims priority to and the benefit of U.S. patent application Ser. No. 11/003,264, filed Dec. 3, 2004 now abandoned, which is incorporated herein by reference in its entirety.

BACKGROUND OF THE INVENTION

1. Field of the Invention

The present invention relates generally to healthcare management systems. More specifically, the present invention relates to a system, software, and related methods for providing pharmaceutical services and inventory control.

2. Description of the Related Art

The approach to healthcare information management systems, in general, has changed significantly over the past few years. Previously mainframe computers with closed system architectures were the only solution. Today's technology uses three-tier client/server open system architectures, enabling: improved system flexibility; fully integrated applications with the ability to use multiple hardware and software vendors; and greatly enhanced information flow. Such integrated healthcare information management systems, typically connected to the computer networks in modern hospitals, allow hospitals to share information among departments and across facilities to enhance patient care.

Despite these advances in healthcare information management systems, hospital information systems typically do not properly integrate pharmacy information services. For example, SAPS® healthcare software provided by the SAP Aktiengesellschaft Corp. and partners T-Systems®, Austria, provides modular hospital information system software that does not include a pharmacy module. In such systems, ordering and delivery of pharmaceuticals typically relies heavily upon the use of manual processes. Written prescription are sent through the hospital mail distribution system to the pharmacy where the physician's order is then entered into a pharmacy's computer system through a dedicated terminal and separately entered into electronic medical records of the hospital information system.

Use of such systems has hampered efficient pharmaceutical order entry, comprehensive clinical and non-clinical checking, electronic recording of medication administrations, maintenance of approved drug formularies, capture of patient allergy information, accurate management of medication inventory, and allocation of healthcare costs to patients and to other cost center users. Improved information communication between the pharmacy and the hospital information system is also required for efficient management of operations and to realize significant cost savings and improved financial management through decision support. Lack of computerized integration with pharmacy hampers integration with automated drug dispensing systems/devices such as the Pyxis MedStation® 2000 by Pyxis Corporation of San Diego, Calif.

Thus, there is a need for an enhanced system integrated into the overall Hospital Information System to provide improved and timely access to drug information, to facilitate computerized physician order entry (CPOE), and to provide pharmacy verification and order management processes, to allow for integration of both inpatient and outpatient clinics, and to improve operations and the safe administration of drugs to patients, to reduce delays, and to streamline the order entry and management process.

SUMMARY OF THE INVENTION

In view of the foregoing, embodiments of the present invention advantageously provide a system, software, and methods related to provision of enhanced pharmaceutical order entry and administration by medical personnel, and enhanced pharmaceutical inventory control within a medical institution. Embodiments of the present invention include healthcare and pharmacy information management software and program products to provide efficient pharmacy-related functions including order entry; comprehensive clinical and non-clinical checking; printing of required bilingual medication labels and patient instructions, electronic recording of medical administration; integration with automated drug dispensing device e.g. PYXIS®, maintenance of approved drug formularies, capture of patient allergy information and accurate management of medication inventory and allocation of costs to patients and to other cost center users. The enhanced system can provide improved and timely access to drug information, to facilitate computerized physician order entry, pharmacy verification, and order management processes, for quality patient care. Improved information access is also provided for management and administrative functions including operations and financial management.

Embodiments of the present invention integrate pharmacy functionality, for both inpatient and outpatient clinics, into the overall hospital information system to provide significant cost savings and improved financial management through decision support, to provide an overall contribution towards limiting increases in operating costs while providing improved quality of patient care, and to provide safe administration of drugs to patients while reducing delays and streamlining the order entry and management process.

Embodiments of the present invention provide a system of enhanced pharmaceutical order entry and administration by medical personnel, and enhanced pharmaceutical inventory control within a medical institution. For example, in an embodiment of the present invention, a system includes a medical institution pharmaceutical information processing and management computer including memory to store data therein, to thereby define a pharmaceutical information management server. The system includes a plurality of patient medication profile records and a corresponding plurality of electronic medication administration records for each of a respective plurality of patients. The system includes at least one, and options for a plurality of hospital drug formularies, and can include a plurality of medication inventory records. These records are preferably stored in a relational database associated with the pharmacy information management server.

The system also includes a medication administration program product including a set of instructions preferably stored in the memory of the pharmaceutical information management server that when executed by the pharmaceutical information management server are adapted to accept remote input from a physician to access the plurality of patient medication profile records, to thereby allow display of a selected patient medication profile. The medication administration program product also includes instructions adapted to produce and allow display of a medication order entry form having input fields that when accessed through instructions by the medication administration program product provides medication administration data to form an electronic medication order accessible by a pharmacist to perform a medication order verification. The medication administration program product instructions are also further adapted to provide the medication administration data to the electronic medication administration records, and to provide to medical institution nursing unit members and other care givers automated medication administration scheduling requirements, to thereby provide enhanced management of medication administration in the medical institution.

The medication administration program product is adapted to access the plurality of patient medication profile records stored in the memory of the pharmaceutical information management server to display a single consolidated patient medication profile including both inpatient and outpatient prescribed medications for each respective patient, and to access the plurality of electronic medication administration records to display a single consolidated patient medication administration profile for a corresponding plurality of patients including both inpatient and outpatient prescribed medications.

The system also includes a communications network in communication with the pharmaceutical information management server, and a plurality of medical institution physician computers positioned remote from the pharmaceutical information management server, each in communication with the pharmaceutical information management server through the communication network. Each physician computer includes memory and software stored in the memory adapted to provide access to the medication administration program product, to allow the physician to display a patient medication profile for a preselected patient, select a desired medication, and display a medication order entry form, so that the physician can create an electronic medication order to provide data to an associated medication profile record and an associated electronic medication administration record, defining computerized physician order entry.

The system also includes at least one but preferably a plurality of medical institution nursing unit computers each positioned remote from the pharmaceutical information management server, in communication with the pharmaceutical information management server through the communication network. Each nursing unit computer includes memory and software stored in the memory adapted to provide access to the medication administration program product to also allow computerized physician order entry so that a nursing unit member can input a physician's medication order, to allow display of medication orders so that the nursing unit member can review pharmacist and physician notes and special instructions and sign-off the scheduled medication orders, and to allow input to the electronic medication administration records so that the nursing unit member can indicate completed administration of the medication orders.

Each nursing unit computer can also include a video display. Advantageously, the medication administration program product is adapted to signal the medical institution nursing unit computer to display on the video display an automated alert indicating a modified medication order, in response to entry of the modified medication order. Also, the medication administration program product is adapted to display on the nursing unit video display an administration schedule auto-refreshed at a preselected time interval to allow automated screen shifting along a medication administration timeline, to thereby provide an automated medication administration schedule.

In an embodiment of the present invention, each nursing unit can include or be associated with a nursing unit printer each positioned remote from the pharmaceutical information management server, in communication with the pharmaceutical information management server through the communication network. Each nursing unit printer includes memory and software stored in the memory adapted to provide access to the medication administration program product. The medication administration program product is adapted to signal either the medical institution nursing unit computer or the medical institution nursing unit printer to cause the medical institution nursing unit printer to print a modified medication order report, in response to entry of the modified medication order. Advantageously, this prevents inadvertent administration of an old medication order and can prevent non-delivery of a new medication order.

In an embodiment of the present invention, the system can include at least one but preferably a plurality of automated drug dispensing devices each positioned in the medical institution and in communication with the pharmaceutical information management server through the communication network to store pharmaceuticals therein and to dispense the pharmaceuticals to authorized medical institution personnel located at the medical institution. Each automated drug dispensing device includes memory and software stored in the memory to provide access to the medication administration program product, to receive electronic medication administration record data, and to provide an interface to modify electronic medication administration records, to thereby provide nursing unit members a tool for recording medication administered to patients.

The system further can include at least one but preferably a plurality of medical institution pharmacy computers in communication with the pharmaceutical information management server through the communication network. Each pharmacy computer includes memory and software stored in the memory adapted to provide access to the medication administration program product, to allow display of queued electronic medication orders awaiting verification by a pharmacist placed through the medical institution physician computers, and to allow input from the pharmacist indicating verification of such medication orders so that the pharmacist can document verifying the electronic medication orders.

In an embodiment of the present invention, the system includes, in addition to or in place of the pharmaceutical information management server, a hospital information processing and management computer including memory to store data therein to thereby define a hospital information management server which can perform the functions described above with respect to the pharmacy information management server. Further, the medication administration program product can function as a module of the hospital information management software stored in the memory of the hospital information management server.

Advantageously, embodiments of the present invention include methods to enhance provision of pharmacy services to medical personnel within a medical institution including pharmaceutical administration, pharmaceutical medication order entry, and enhanced pharmaceutical inventory control. For example, in an embodiment of the present invention, a method to enhance pharmaceutical order entry by medical personnel within a medical institution includes providing a graphical user interface medication order template or form having database entry fields displayed on a video display device to allow medication order entry by an authorized physician at a location remote from a medical institution pharmacy. The medication order template or form can provide default values and/or templates to help expedite the computerized physician order entry. The medication order template or form is also adapted to display and includes provisions for performing clinical and non-clinical checks. If a physician encounters a clinical or non-clinical alert, advantageously, the physician can either change the affected medication order entry or override the clinical or non-clinical alert. If the physician chooses to override the alert, the physician is provided an entry field in the graphical user interface medication order template or form to input an override reason, either free-text or by way of a reason code. In response to the entry of the electronic medication order, a respective patient electronic medication administration record is then updated or created.

A pharmacist is provided a computer (or clinical workstation) including a video display device to display a graphical user interface including the medication order entered by the physician, along with other queued orders from other physicians. Advantageously, along with each electronic medication order, the graphical user interface can display both clinical and non-clinical alerts encountered by the respective physician along with overriding reasons posted by the physician with the alerts. This configuration enhances reviewing and verifying the medication order displayed on the pharmacy clinical workstation.

In an embodiment of the present invention, a method to enhance pharmaceutical medication order entry while simultaneously reducing medication order errors is provided. The method includes the steps of providing a structured computer-based electronic medication order form including medication route, dose, frequency, and duration; and providing in the form default values for the route, dose, frequency, and/or duration, to help expedite the computerized physician and/or pharmacist order entry. Further, the method can include the steps of providing in the form access to dosing recommendations including minimum and maximum dose, lifetime cumulative dosing, pediatric dosing, neonatal dosing, and geriatric dosing; and providing in the form access to standard medication order sets, IV templates, and/or chemotherapy templates.

In an embodiment of the present invention, a method to enhance pharmaceutical medication order entry while simultaneously reducing medication order errors includes the steps of providing a graphical user interface database template having database entry fields displayed on a video display device to allow electronic medication order entry by a physician at a location remote from a medical institution pharmacy; displaying in the database template, tools to access default values for medication dosing, sets of medications frequently prescribed together, and default medication order templates, provided to enhance medication order entry and reduce likelihood of medication order errors. The method also includes the step of displaying in the database template, tools to access products available to treat a preselected disease condition with emphasis on drugs in the medical institution drug formulary.

In an embodiment of the present invention, a method to enhance pharmaceutical medication order management compliance is provided. The method includes the step of providing a structured computer-based electronic medication order form including access to a master list of intervention codes grouped by code type to allow for the capture of interventions by physicians during computerized medication order entry, the capture of interventions by pharmacists during computerized medication order entry and computerized medication order verification, and the capture of interventions by nursing unit members during computerized medication order entry and medication administration, to thereby enhance non-compliance tracking. The method also includes the step of providing an alert during computerized physician medication order entry signaling that an entry requiring an intervention event has been encountered and that an action is required to override the alert. The method further includes the steps of providing automated intervention logging to capture details of the intervention event, and providing exception documentation for alert overrides to allow for enhanced management review.

In an embodiment of the present invention, a method to enhance pharmaceutical order entry by medical personnel and enhanced pharmaceutical inventory control within a medical institution is provided. The method includes the steps of: providing a report, preferably organized by nursing unit or prescribing physician, listing medication orders for inpatient residents at the medical institution that are about to expire within a preselected time period; and providing automated stop notification to a physician responsible for a medication order scheduled to expire within the preselected time period. The method further can include the step of providing a physician work queue requiring the notified physician to either extend the medication order or confirm the medication order stop time, preventing inadvertent interruption of patients' medication services.

In an embodiment of the present invention, a method to enhance pharmaceutical administration is provided. The method includes the steps of: displaying on a nursing unit video display device a nursing unit-level electronic medication administration screen providing a listing of electronic medication administration records; monitoring by a nurse the nursing unit-level electronic medication administration screen for new and changed (modified) medication orders; and providing automated highlighting on the nursing unit-level electronic medication administration screen of any new or changed (modified) medication orders.

In an embodiment of the present invention, a method to enhance pharmaceutical administration is provided. The method includes the steps of: displaying an administration schedule auto-refreshed at a preselected time interval to allow automated screen shifting along a medication administration timeline; and can include providing automated highlighting of new and changed (modified) medication orders on the administration schedule, responsive to entry of a new or changed (modified) medication order. The method can further include the step of providing automated printing of the new or changed (modified) medication order on a nursing unit printer, responsive to entry of the new or changed (modified) medication order.

In another embodiment of the present invention, a method to enhance pharmaceutical order entry by medical personnel within a medical institution is provided. The method includes the steps of: displaying on a video device positioned at a nursing unit located remote from a medical institution pharmacy, a graphical user interface including electronic medication administration record data to allow medication administration entry by an authorized nursing unit member; posting a medication administration for an emergency medical services medication order in the graphical user interface; and performing an automated creation of an electronic emergency medical services medication order responsive to posting the medication administration for the emergency medical services medication order. Advantageously, this provides for electronic medication order creation and thus, a convenient means for documenting both a medication order and its administration, in an emergency medication situation.

In another embodiment of the present invention, a method to enhance pharmaceutical order entry by medical personnel within a medical institution includes the steps of: displaying on a video device positioned at a nursing unit located remote from a medical institution pharmacy a graphical user interface including electronic medication administration record data to allow medication administration entry by an authorized medical institution member; posting a medication administration for an immunization medication order in the graphical user interface; and performing an automated creation of an electronic immunization medication order including an optional physician confirmation requirement within a preselected time interval, responsive to posting the medication administration for the immunization medical order.

Embodiments of the present invention also include a computer readable medium or means that is readable by a computer (or server) to enhance pharmaceutical order entry and administration by medical personnel, and enhanced pharmaceutical inventory control within a medical institution. For example, in an embodiment of the present invention, the computer readable medium or means includes a set of instructions that, when executed by the computer cause the computer to perform the operation of displaying on a physician video display device a graphical user interface including a medication order template or form having database entry fields to allow medication order entry by a physician. The instructions can further perform the operations of: populating the medication order template or form with default values or applying a medication order ingredient template. The medication order template or form can provide access to tools for the physician to perform clinical and non-clinical checks.

In response to receipt of an entry in the medication order template or form of a medication order parameter violating a preselected rule, a clinical and/or non-clinical alert is displayed. Further, the operations performed can include displaying on the graphical user interface, an entry field providing the physician an ability to override the clinical or non-clinical alert, followed by automated intervention logging and an automated update of a respective patient electronic medication administration record.

In an embodiment of the present invention, the computer readable medium or means includes a set of instructions that cause the computer to perform the operations of receiving a electronic medication order entered by a physician, responsive to the medication order entry by the physician, and queuing in a pharmacist working queue the electronic medication order. The queued electronic medication order can be displayed on a pharmacy clinical workstation video display device along with any clinical and non-clinical alerts encountered by the physician and any override reasons posted by the physician.

Further, displayed is an entry field providing the pharmacist an ability to override any clinical or non-clinical alerts encountered during medication order review and verification. As with the physician, in response to such an intervention by the pharmacist, operations performed include automated intervention logging, and can include the displaying of an entry field to provide for entry by the pharmacist of either a reason code or free-form text to describe a reason for the intervention. Further, the operations performed can include processing the electronic medication order responsive to the review and verification of the medication orders and the clinical and non-clinical checks of the medication order.

In an embodiment of the present invention, the computer readable medium or means includes a set of instructions that cause the computer to perform the operation of displaying on a video device positioned at a nursing unit located remote from the pharmacy, a graphical user interface including a nursing unit-level electronic medication administration screen having electronic medication administration record data to allow medication administration entry by an authorized nursing unit member. The instructions can also include those to perform the operation of displaying an electronic medication administration schedule auto-refreshed at a preselected time interval to allow automated screen shifting along a medication ETC administration timeline, and providing an alert to the nursing unit indicating a new or changed (modified) electronic medication order.

In an embodiment of the present invention, the computer readable medium or means includes a set of instructions that cause the computer to perform the operations of: receiving a posting of a medication administration for an unscheduled medication order in a graphical user interface preferably displayed on a nursing unit video display device; performing an automated creation of an electronic medication order for the administered medication order, in response to the posting of the medication administration; and providing a special queue for a pharmacist to review and verify electronic medication orders created through posting such a medication administration.

In an embodiment of the present invention, the computer readable medium or means includes a set of instructions that cause the computer to perform the operations of: determining if any of a plurality of medication orders for inpatient residents at a medical institution are about to expire within a preselected time period; and providing automated stop notification to a computer associated with a physician responsible for a medication order scheduled to expire within the preselected time period. The instructions can also include those to perform the operation of providing a physician work queue requiring the notified physician to either extend the medication order or confirm the medication order stop time. Advantageously, this requirement helps ensure inpatient medication service is not inadvertently interrupted.

Advantageously, computerized physician order entry (CPOE) enhances the medication ordering process. CPOE can provide on-line eligibility checking during medication order entry, can eliminate transcription errors by replacement of manual transcription of order information, and can provide structured orders: route, dose, frequency, and duration, utilizing physician choice lists, standard order sets, ordering regimens, and IV and TPN templates. CPOE can provide dosing recommendations: min/max, lifetime cumulative, pediatric, neonatal, and geriatric dosing from e.g. First DataBank. CPOE also can provide specialized protocol ordering, e.g., chemotherapy including attributes such as: dose, frequency, route; and duration in compliance with protocol; and can provide access to external drug information (e.g., AHFS® and ETC® Monographs from First DataBank). CPOE can advantageously provide a check against a hospital or medical institution drug formulary, and can provide enhanced clinical checking e.g., duplicate therapy checking; drug-drug interaction checking; drug-allergy interaction checking; drug-lab interaction checking; therapeutic substitutions; and dose check against age, weight, and body surface area. CPOE can provide expiring medication orders alerts, exception documentation for alert overrides and interventions, integration with laboratory results, optional drug-disease interaction checks with available ICD-9 coding, and can support pharmacy verification of medication orders.

Advantageously, implementation of electronic medication administration records (EMAR) enhance the medication administration process with complete point-of-care documentation. EMAR helps users identify easily what medications have been ordered for a patient, and allows for nursing sign-off of scheduled medication orders. EMAR can provide for the display of scheduled administration times with order details, and can provide for real-time reminders and alerts to nursing units, resulting in a decrease in medication errors. EMAR allows nursing unit members to review pharmacist and physician notes and special instructions, and to review a patient medication profile, a patient significant datasheet, patient laboratory/other results, patient demographics, and patient diagnosis information. EMAR helps simplify recording of medication administrations and pertinent details, and enables real-time recording of nursing interventions and notes.

Advantageously, the medication administration program product can support EMAR posting of unscheduled orders in inpatient (e.g., STAT/ASAP orders) and in outpatient clinics (e.g., EMS, Immunizations) settings, can provide for integration and support for automated drug dispensing device-EMAR functionality, and can provide storage location management of the drug to be administered. The medication administration program product can also provide for integration of EMAR and Care Docs, improved medication inventory management, and advantageously can capture accurate medication costs for patient and other user-cost centers, at the patient level, for enhanced financial reporting and business planning.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

Figure 11:
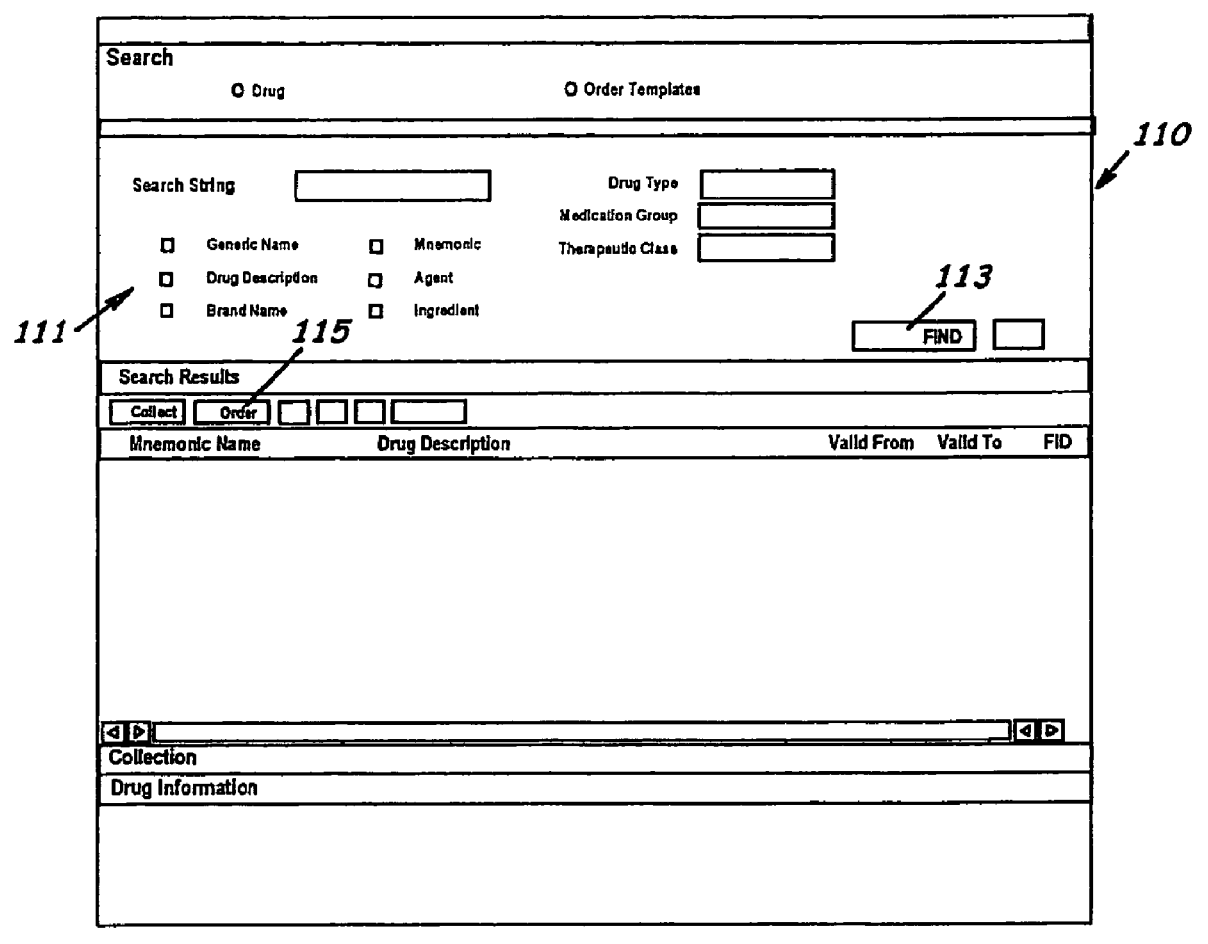

FIG. 11 is a schematic view of a graphical user interface according to an embodiment of the present invention;

FIG. 25 is a schematic table diagram illustrating change management functional areas and associated functional area categories according to an embodiment of the present invention.

DETAILED DESCRIPTION

The present invention now will be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1:
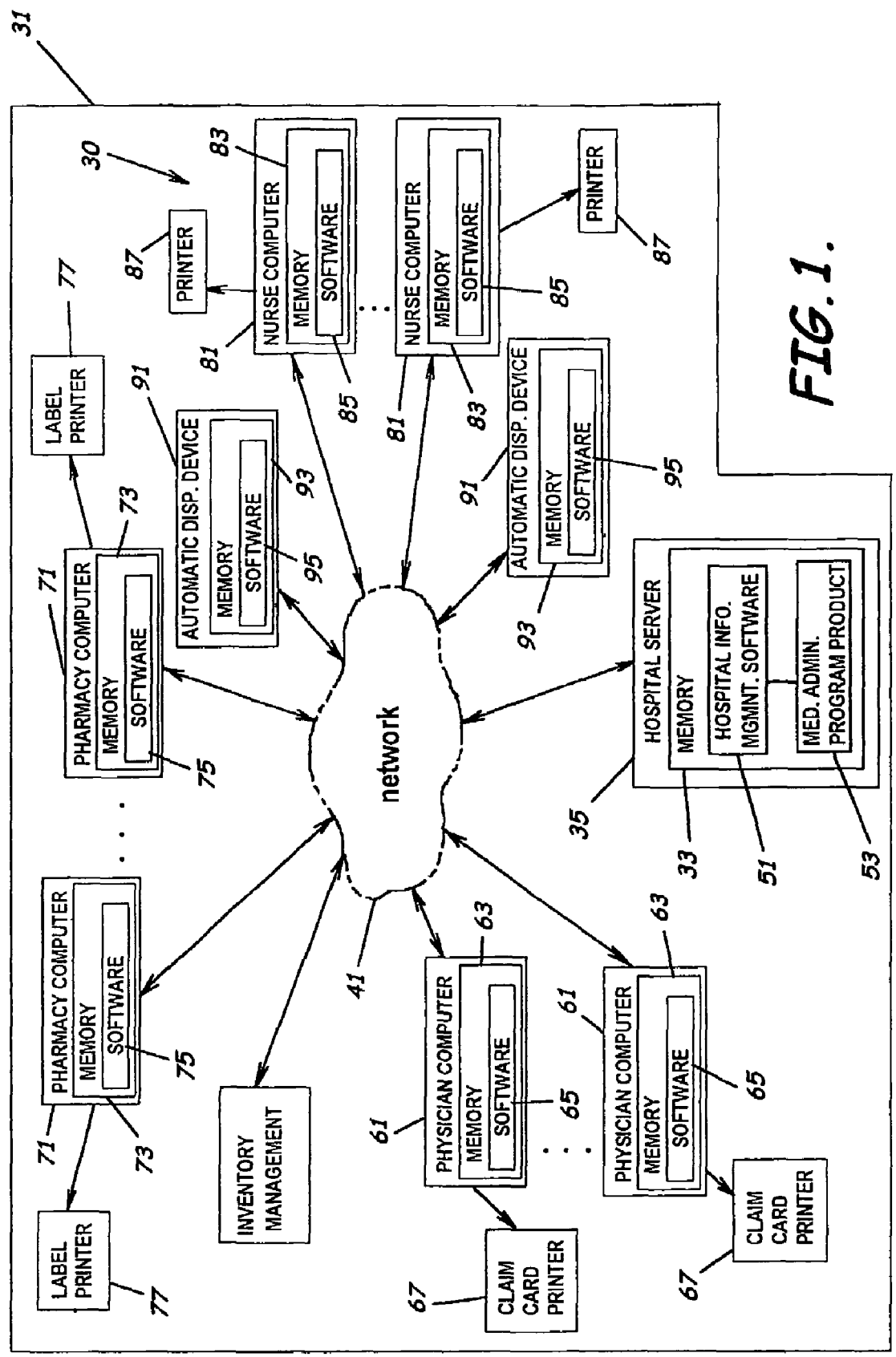
FIG. 1 is a schematic block diagram of a plurality of physician computers, pharmacy computers, and nursing computers networked to a hospital server to provide enhanced pharmacy services for a medical institution according to an embodiment of the present invention.
Figure 2:
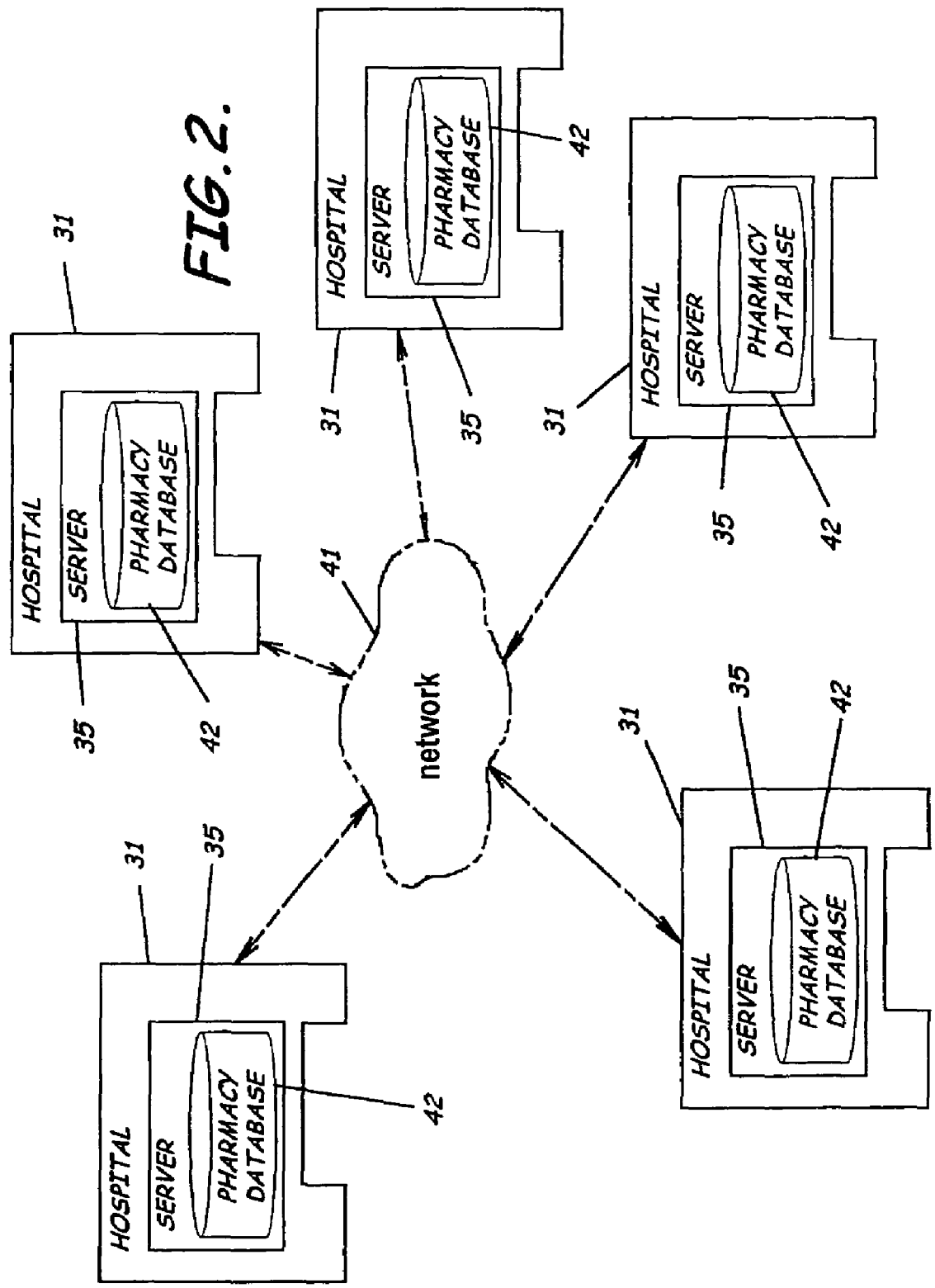
FIG. 2 is a schematic block diagram of a plurality of medical institutions of FIG. 1 according to an embodiment of the present invention.

FIGS. 1-25 illustrate a system 30 of enhanced pharmaceutical order entry and administration by medical personnel, and enhanced pharmaceutical inventory control within a medical institution such as, for example, hospital 31 that, according to an embodiment of the present invention, includes an information processing and management computer including memory 33 to store data therein to thereby define a hospital information management server 35. The system 30 also can include a pharmacy management server 37 (see FIG. 4) including memory 39 in communication with a communication network 41. The hospital information management server 35 is also in communication with the communications network 41, which provides communication between the various network components. According to the preferred embodiment of the present invention, each of the servers 35, 37, is provided access to a database 42 which generally stores various hospital and pharmacy related records including patient medication profile records 43 and a corresponding plurality of electronic medication administration records 45 for each of a respective plurality of patients, patient master data records 46, a hospital drug formulary 47, and a plurality of medication inventory records 49. FIG. 2 illustrates an embodiment including pharmacy management in multiple institutional environments incorporating multiple systems 30.

In the preferred embodiment of the present invention, hospital information management software 51 is stored in the memory 33 of the hospital information management server 35. The software 51 includes or interfaces with a medication administration program product 53 which includes a set of instructions that, when executed by the server 35, cause the server 35 to accept remote input from physicians Ph (see FIG. 3) to access the patient medication profile records 43 to thereby allow display of a selected patient medication profile, and to access the hospital drug formulary 47 to thereby allow search for and/or selection of a desired medication. Note, in the preferred embodiment of the present invention, the medication administration program product 53 is an add-on to hospital information management software, which will be understood by those skilled in the art. An example of such hospital information management software is an industry specific version of SAP® known as MySAP Healthcare including IS-Hospitals software and IS-H* Medicals software, provided by the SAP Aktiengesellschaft Corp., Waldorf, Germany, and partners T-Systems®, Vienna, Austria. The medication administration program product 53, can, however, in an alternate embodiment of the present invention, function as a stand-alone program product that can be stored and executed in either the memory 33 of the hospital information management server 35, the memory 39 of the pharmacy management server 37, distributed between the servers 35, 37, or in a server (not shown) remote from the hospital environment. Note, the hospital information management software 51 and the medication administration program product 53 can be in the form of microcode, programs, routines, and symbolic languages that provide a specific set for sets of ordered operations that control the functioning of the hardware and direct its operation, as known and understood by those skilled in the art.

Figure 4:
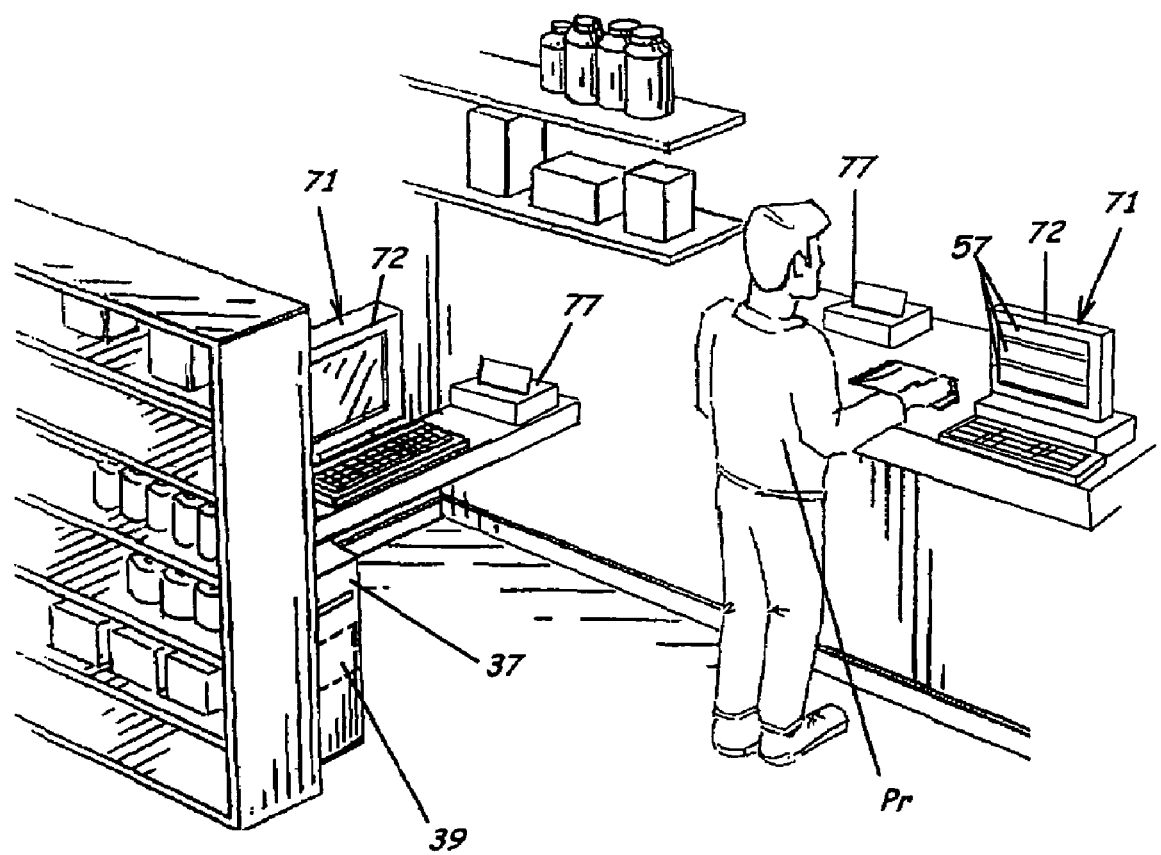
FIG. 4 is an environmental perspective view of a medical institution pharmacy workstation according to an embodiment of the present invention.
Figure 5:
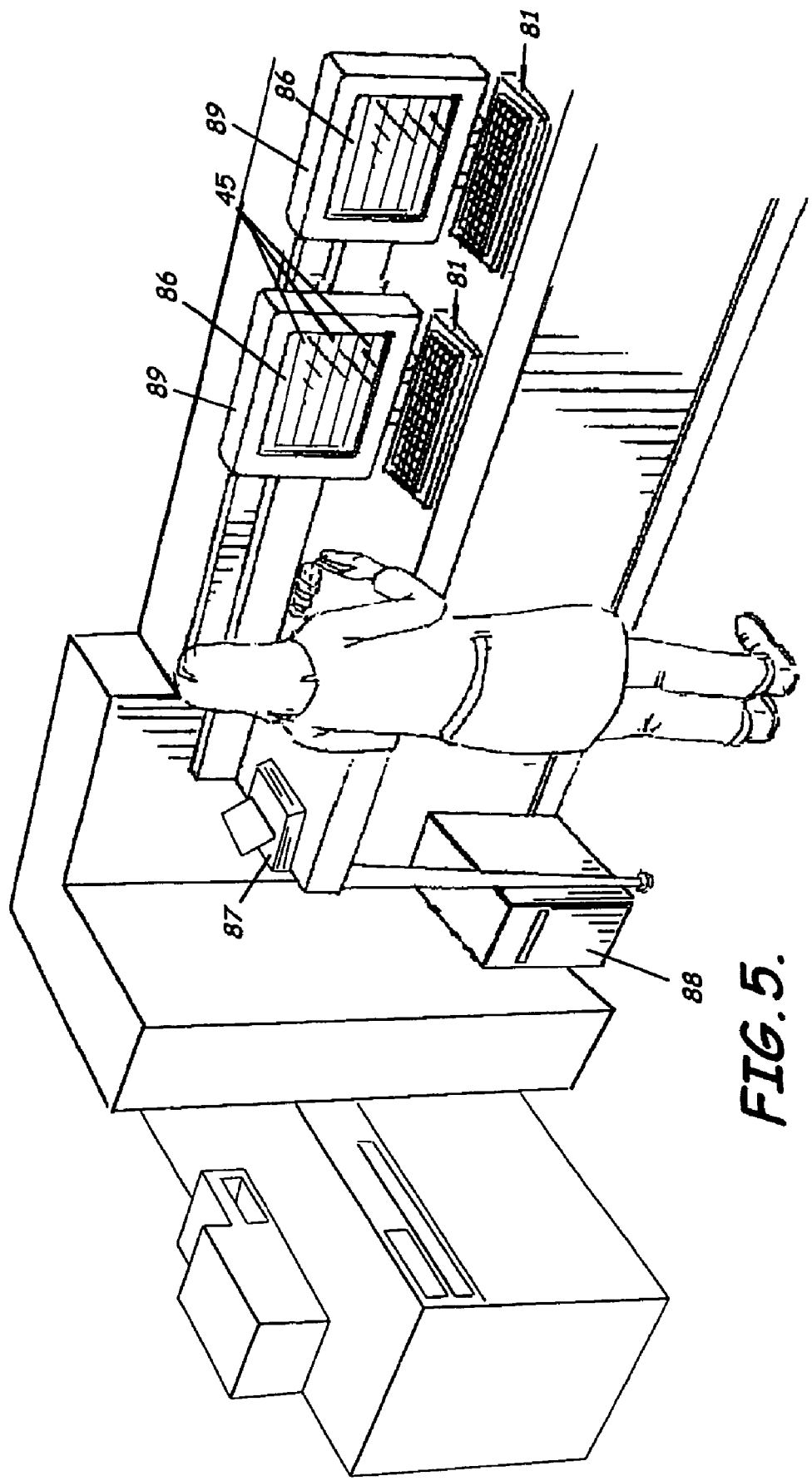
FIG. 5 is an environmental perspective view of a nursing unit workstation according to an embodiment of the present invention.
Figure 6:
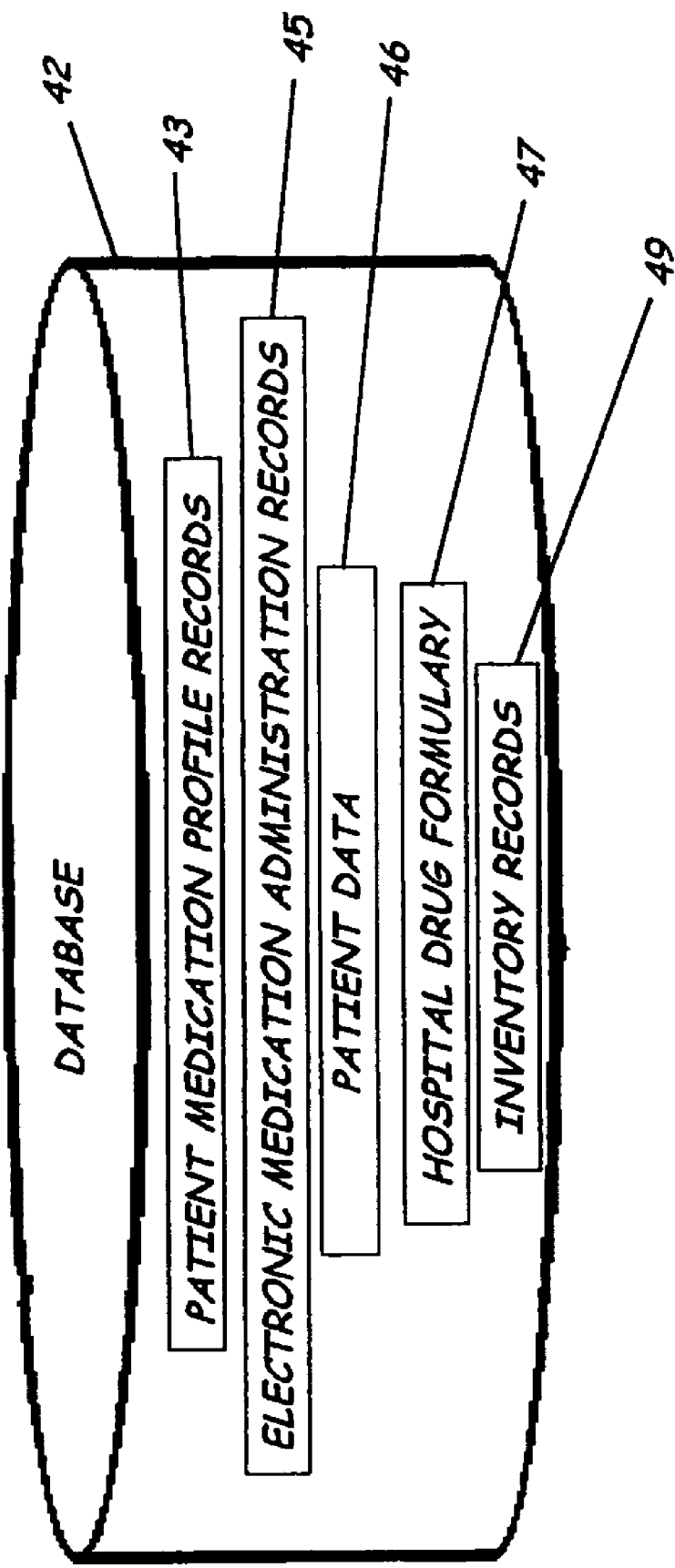
FIG. 6 is a schematic view of a database according to an embodiment of the present invention.

The medication administration program product 53 also includes instructions adapted to produce and allow display of a medication order entry form 55 (see FIGS. 3 and 12) having database record input fields that when accessed and completed provide medication administration data to form an electronic medication order 57 (see FIG. 4) accessible by a pharmacist Pr, and to provide the medication administration data to the electronic medication administration records 45 (see FIGS. 5 and 6). The medication administration program product 53 further includes instructions adapted to interface the electronic medication administration records 45 with the medication inventory records 49 (see FIG. 6), and to interface the electronic medication administration records 45 with hospital nursing member medication scheduling, to thereby provide enhanced management of medication administration in the hospital 31.

In an embodiment of the present invention, the patient medication profile records 43 stored in the database function can form a single consolidated patient medication profile including both inpatient and outpatient prescribed medications (see FIG. 10) for a respective patient. Advantageously, this consolidated medication profile can be displayed through combining both inpatient and outpatient prescribed medications into a single patient medication record 43 or through the extraction of data contained in a separate inpatient and outpatient medication profile records 43 stored for each patient, and through the medication administration program product 53 displaying the patient medication profile in a combined form. Unlike prior systems, this configuration minimizes the requirement for a healthcare practitioner to view multiple profiles in order to determine the actual profile for the patient. Further, each of the plurality of electronic medication administration records 45 can provide a single consolidated patient medication administration profile for a corresponding plurality of patients, the single profile reflecting current medication administration including both inpatient and outpatient prescribed medications. Advantageously, this configuration graphically enhances monitoring medication administration and can help streamline establishing medication administration schedules.

Figure 3:
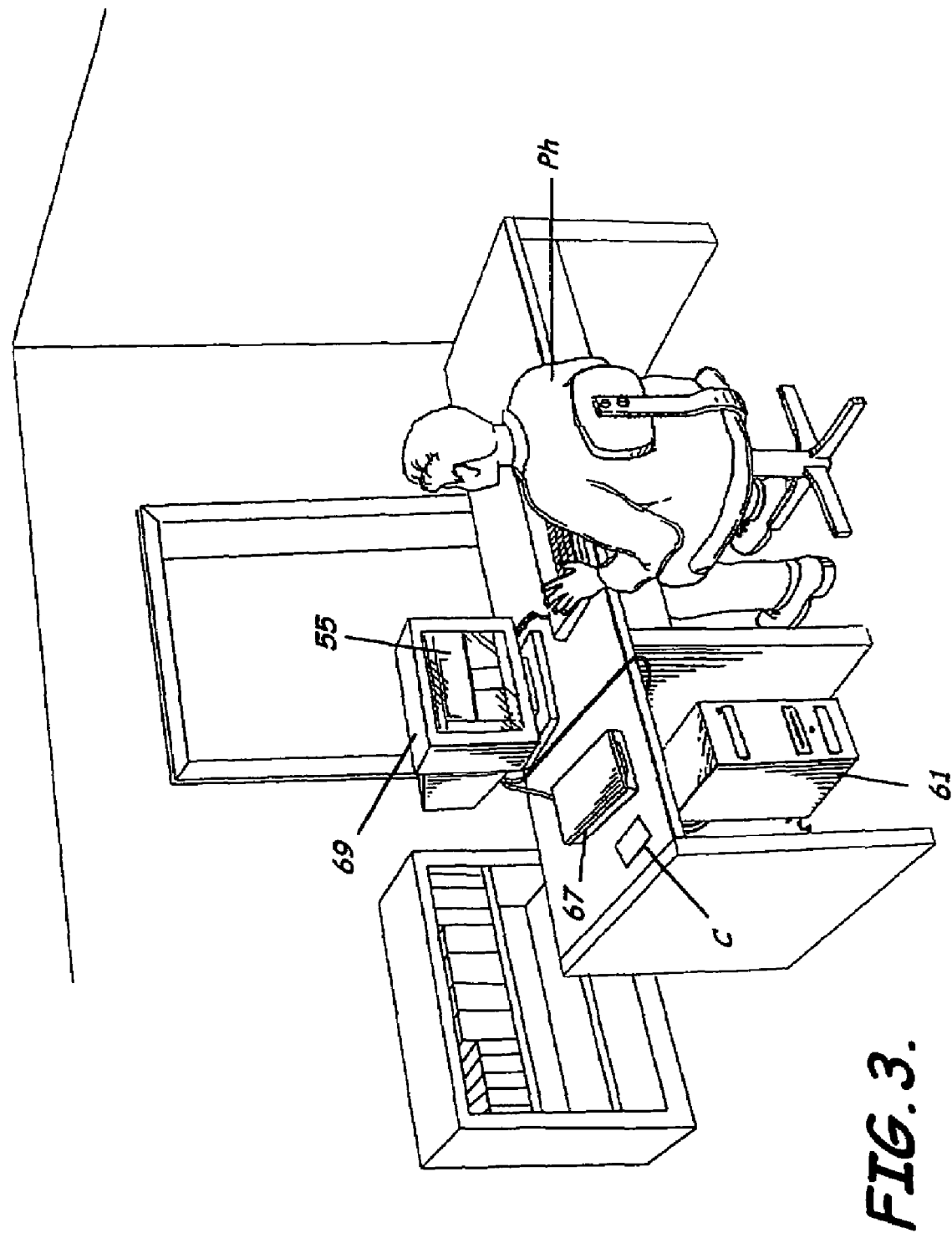
FIG. 3 is an environmental perspective view of a physician clinical workstation according to an embodiment of the present invention.

As perhaps best shown in FIG. 3, in the preferred embodiment of the present invention, the system 30 can include a plurality of hospital physician computers 61 positioned preferably throughout the hospital 31 and remote from the hospital information management server 35. Each computer 61 is positioned in communication with the hospital information management server 35 through the communication network 41 and each includes memory 63 and software 65 stored in the memory adapted to provide access to the medication administration program product 53. Advantageously, this configuration allows the physician Ph to display a patient medication profile for a preselected patient, select a desired medication, and display a medication order entry form 55, so that the physician Ph can create an electronic medication order 57 to provide data to an associated electronic medication administration record 45, defining computerized physician order entry ("CPOE"). In another embodiment of the present invention, the hospital physician computers 61 are connected to the network 41 through a hospital physician server (not shown) or series of servers functionally positioned throughout the hospital 31. Note, the term physician can include both the physician and physician's assistant, or other authorized agent.

Each of a plurality of claim-card printers 67 can be separately connected to a hospital physician computer 61 either directly or through the network 41 to print for outpatients a claim card C indicating a medication entered through computerized physician order entry. Although the claim card C conceptually can function as a substitute for a former written medication order, it is preferably not authorized to be used as a medication order but rather as evidence of the electronic medication order 57 which can be used to expedite claiming medication from the pharmacy. This prevents the patient from claiming medication from one pharmacy based on the electronic medication order 57 and from another pharmacy based on the claim card C.

As perhaps best shown in FIG. 4, the system 30 can include a plurality of hospital pharmacy computers (clinical workstations) 71 including a video display 72 preferably positioned in the hospital 31 and remote from the hospital information management server 35. Each computer 71 is in communication with the hospital information management server 35 through the communication network 41 and each includes memory 73 (see FIG. 1) and software 75 stored in the memory adapted to provide access to the medication administration program product 53. Advantageously, this configuration allows the pharmacist or pharmacists Pr to display queued electronic medication orders 57 awaiting verification by the pharmacist placed through the plurality of hospital physician computers 61, and to allow input from the pharmacist Pr indicating verification of such medication orders 57 in their respective electronic medication administration records 45, so that the pharmacist Pr can document verifying the medication orders 57. The hospital pharmacy computers 71 can function independently, as shown in FIG. 1, or, as shown in FIG. 4, can be in communication with and/for function through the pharmacy management server 37. Either configuration, along with others known to those skilled in the art, are within the scope of the present invention. Note, the term pharmacist can include pharmacists, pharmacy technicians and aides, trainee pharmacists, or other pharmacist authorized agents.

At least one but preferably a plurality of label printers 77 can be connected either to a hospital pharmacy computer 71 either directly or through the network 41 to print a medication label indicating a medication, instructions, and warnings, according to the medication order 57. As will be described later, advantageously, the medication labels can be printed in order to prioritize instructions or warnings and can print in either English or a foreign language, or both.

As perhaps best shown in FIG. 5, in the preferred embodiment of the present invention, the system 30 can include a plurality of hospital nursing unit computers 81 positioned preferably throughout the hospital 31 and at each nursing unit, remote from the hospital information management server 35. Each computer 81 is in communication with the hospital information management server 35 through the communication network 41. Each includes memory 83 (see FIG. 1) and software 85 stored in the memory adapted to provide access to the medication administration program product 53. Advantageously, this configuration also allows computerized physician order entry by nursing unit members NM so that a nursing unit member NM can input a physician's medication order. This configuration also allows the medication administration program product 53 to display scheduled inpatient verified medication orders on an electronic medication administration record display screen 86, so that the nursing unit members NM can review pharmacist and physician notes and special instructions and sign-off the scheduled medication orders 57. Further, this configuration allows the nursing unit members NM direct input to the displayed electronic medication administration records 45 so that the nursing unit members NM can indicate completed administration of the inpatient verified medication orders. Note, the term nursing unit member includes nurses, nurse's aides, ward clerks, and other authorized nursing agents.

In another embodiment of the present invention, the plurality of hospital nursing unit computers 81 are connected to the network 41 through a respective hospital nursing unit server 88 or series of servers assigned to the set of the hospital nursing unit computers 81 preferably grouped to coincide with the physical location of the nursing units.

At least one nursing unit printer 87 for each nursing unit can be connected to a hospital nursing unit computer 81 either directly or through the network 41 to print new or changed orders. This printing function is preferably automatically implemented immediately in response to completion of entry of a new or changed medication order 57 by the physician Ph. Further, at least one associated nursing unit computer 81 can display an alarm generated by the medication administration program product 53 to alert the nursing unit of the new or change order to prevent delivery of an incorrect medication or medication attribute (e.g. amount, time). Alternatively, indication of the new or changed order can be displayed on an associated video display 89 which can flash or sound and alert to indicating the existence of the new or changed order.

Figure 8A:
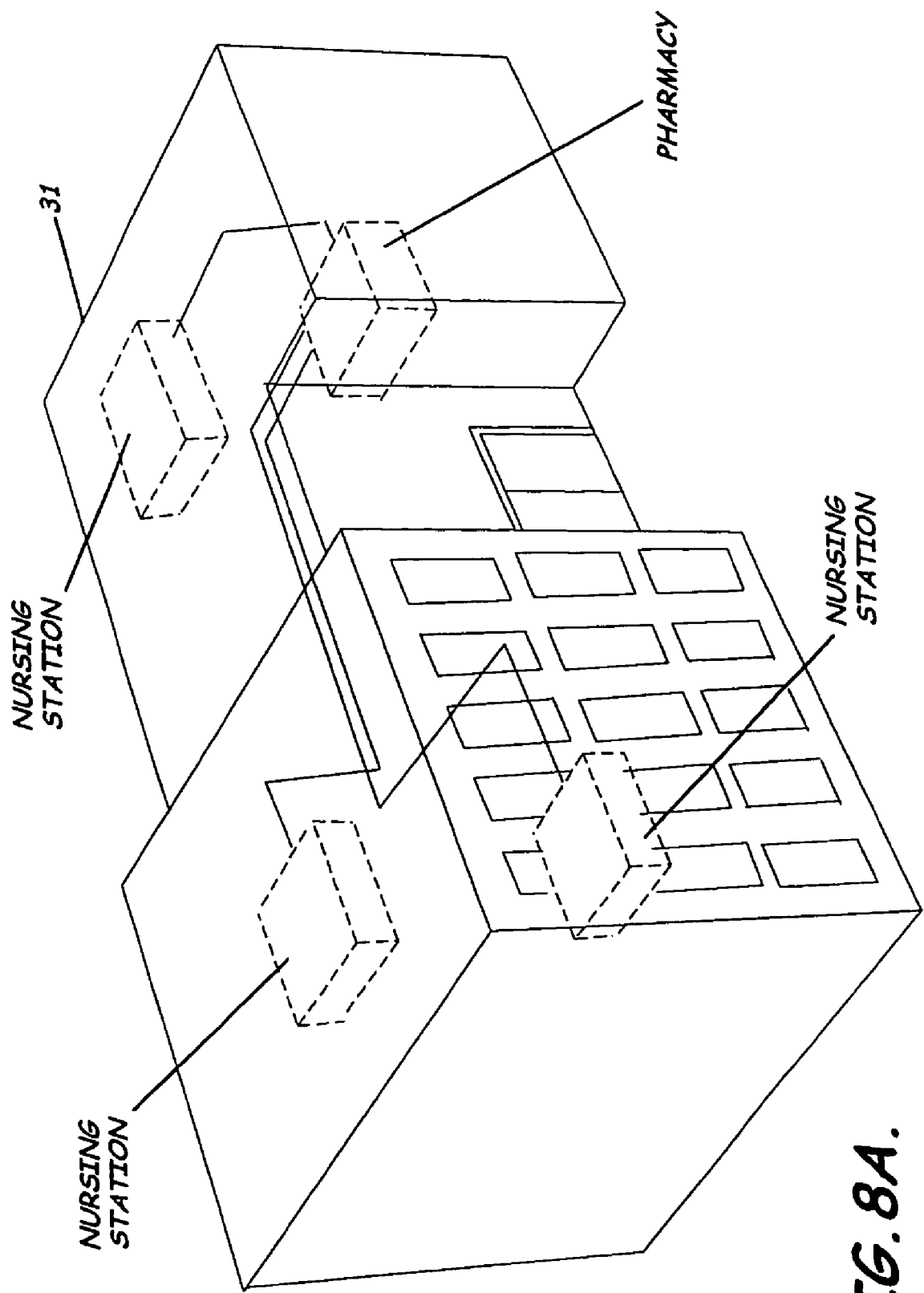
FIG. 8A is a perspective view of a medical institution according to an embodiment of the present invention.
Figure 8B:
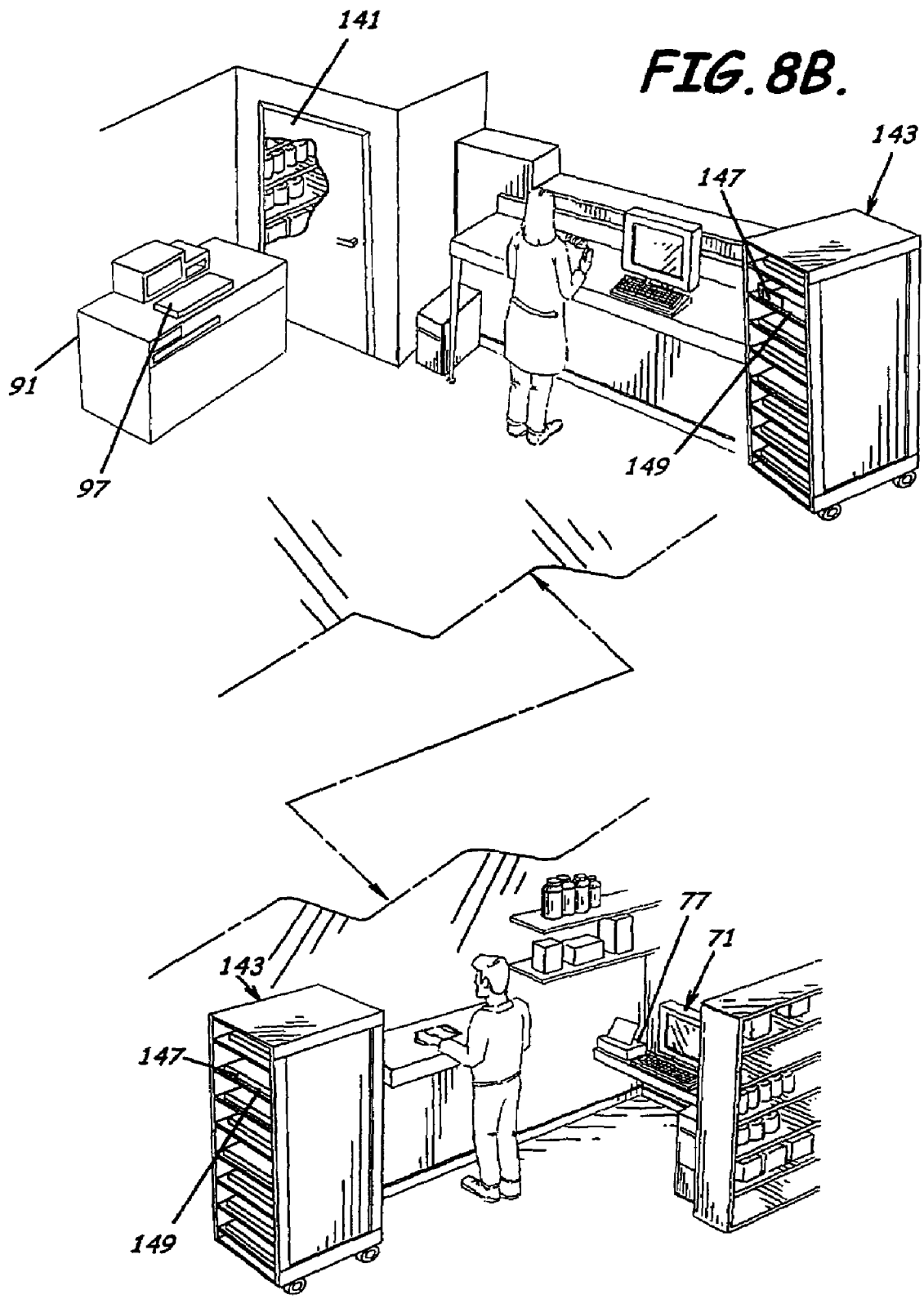
FIG. 8B is an environmental perspective view of a nursing unit workstation and pharmacy workstation including medication storage facilities according to an embodiment of the present invention.
Figure 9A:
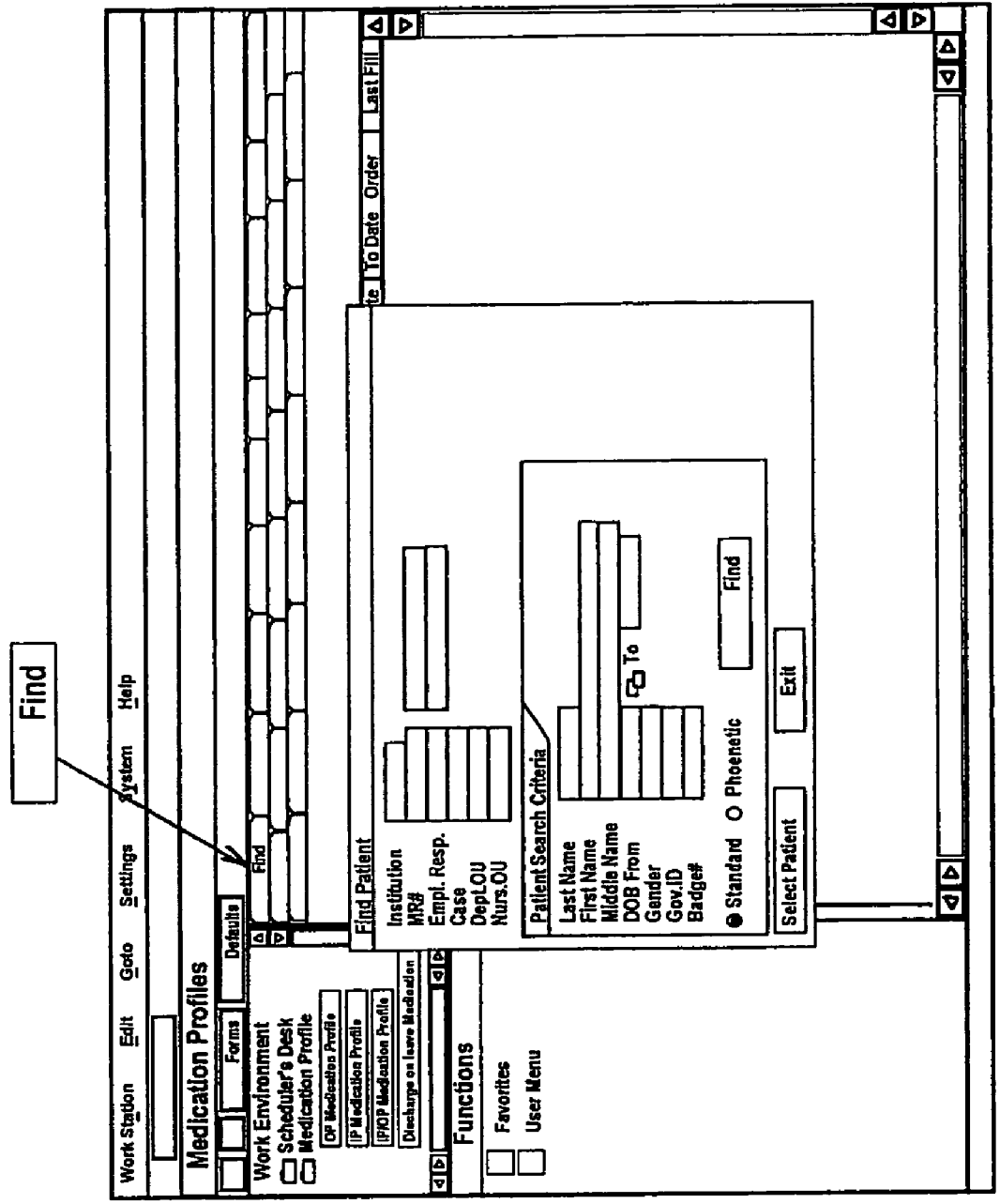
FIG. 9A is a schematic view of a graphical user interface according to an embodiment of the present invention.
Figure 9B:
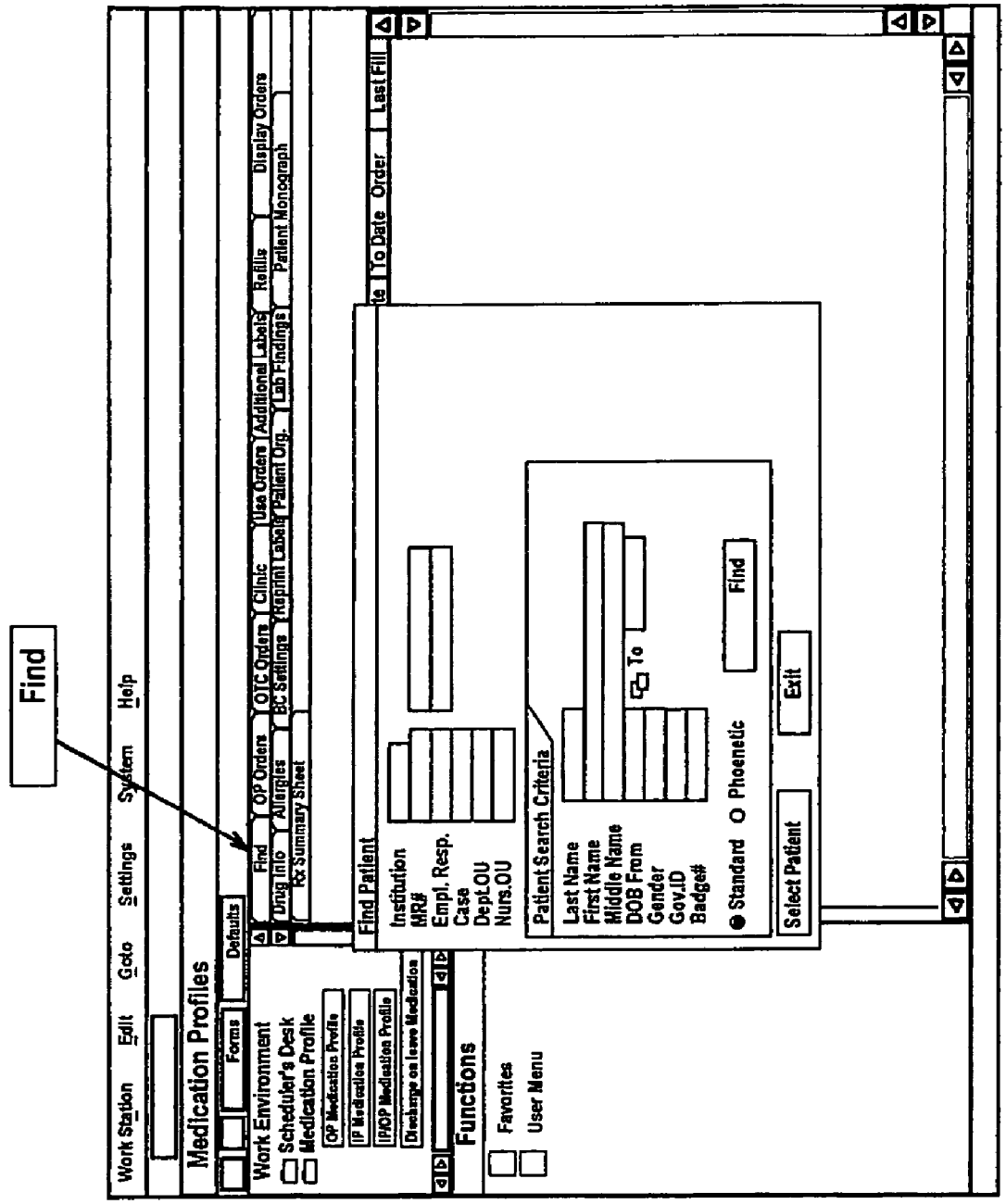
FIG. 9B is a schematic view of a graphical user interface according to an embodiment of the present invention.

As perhaps best shown in FIGS. 1 and 8B, the system 30 can also include a plurality of automated drug (or medication) dispensing devices 91 each positioned in the hospital 31 and in communication with the hospital information management server 35 through the communication network 41 to store a plurality of different pharmaceuticals therein and to dispense the pharmaceuticals to authorized hospital personnel located at the hospital 31. Each automated drug dispensing device 91 includes memory 93 and software 95 stored in the memory 93 to provide access to the medication administration program product 53 to receive electronic medication administration record data and to provide an interface to modify electronic medication administration records 45, to thereby provide hospital personnel a tool for recording medication administered to patients.

Each automated drug dispensing device 91 can store oral solid medications and includes compartments for bulk storage capabilities, and are well known by those skilled in the art. An example of such an automated drug dispensing device 91, as understood by those skilled in the art, is the Pyxis Medstation® by Pyxis Corporation of San Diego, Calif. The Pyxis Medstation®, for example, is a dispensing machine capable of securely storing bulk medication for automated patient-specific dispensing. The Pyxis Medstation® is capable of packaging medications in individual patient-specific envelopes, both on-demand or at a predetermined time interval, and can organize the patient's envelopes into medication carriers. Each envelope can be labeled by the device with standard label information similar to that described previously. The Pyxis Medstation® can store bulk medications in refill cartridges and containers providing an on-site supply of medications.

Advantageously, each automated drug dispensing device 91 can be functionally considered by inventory management to be a separate storage facility. Each automated drug dispensing device 91 maintains an accounting of inventory of medication stored therein, as will be described in more detail later. Each device 91 can also periodically provide the medication administration program product 53 an inventory status usable to allow update of the medication inventory records 49 (see FIG. 6).

The software 95 in the each automatic dispensing device 91 can interface and communicate with the medication administration program product 53 preferably using the Health-Level 7 interface engine. Specifically, each of the plurality of automated drug dispensing devices 91 used in a nursing unit can communicate with the medication administration program product 53 to provide automated posting of medication removal events to a patient associated electronic medication administration record 45. Each of the plurality of automated drug dispensing devices 91 used in a nursing unit can be positioned to perform an automated posting of a time-of-removal of medication from the respective automated drug dispensing device 91 to a patient associated electronic medication administration record 45. Further, each of the plurality of automated drug dispensing devices 91 used in a nursing unit can provide an input device 97 positioned to allow the nursing unit member to post an actual medication administration time to the patient associated electronic medication administration record 45, when so displayed.

Figure 7A:
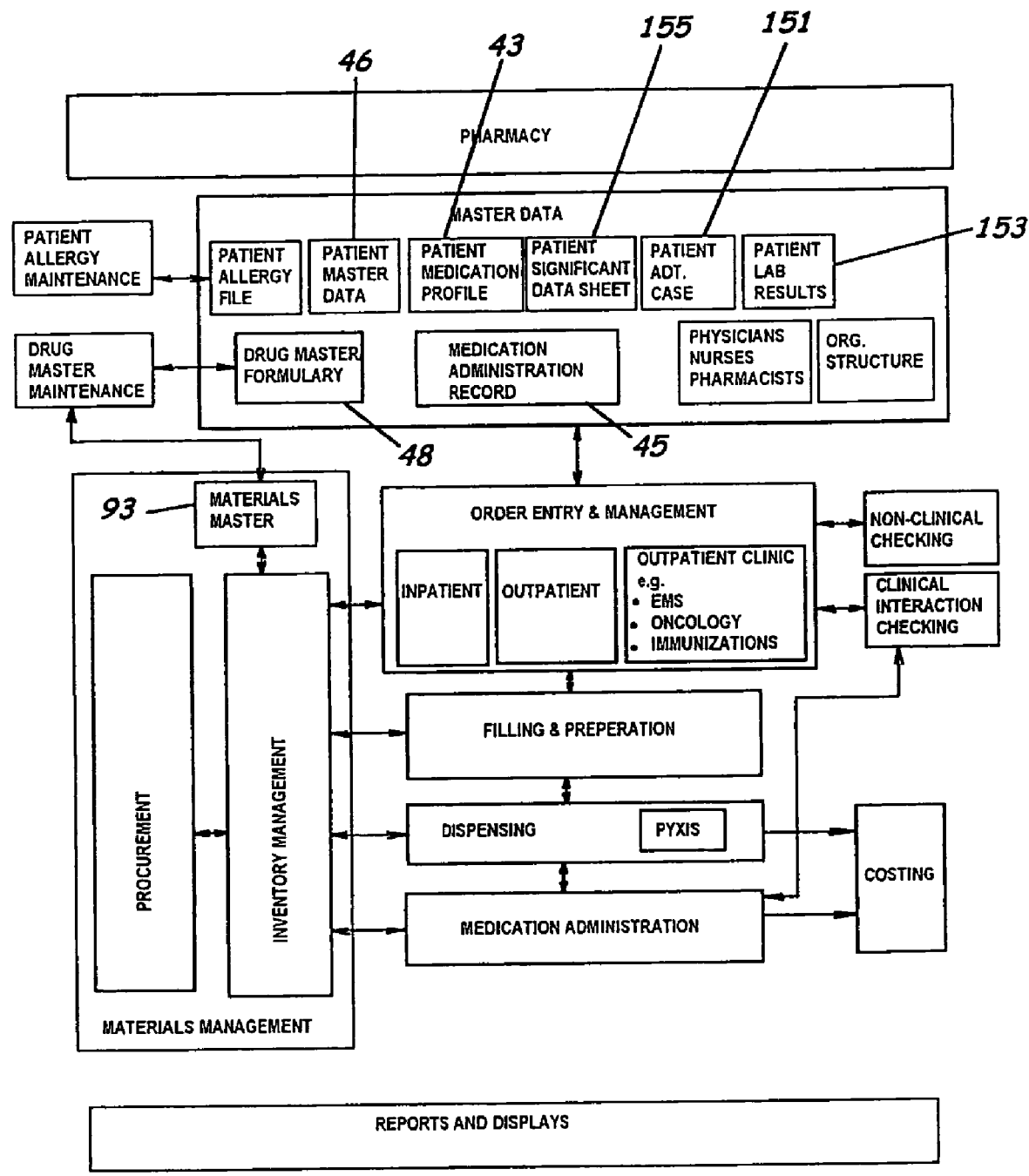
FIG. 7A is a schematic view of a high-level view of a business processes according to an embodiment of the present invention.
Figure 7B:
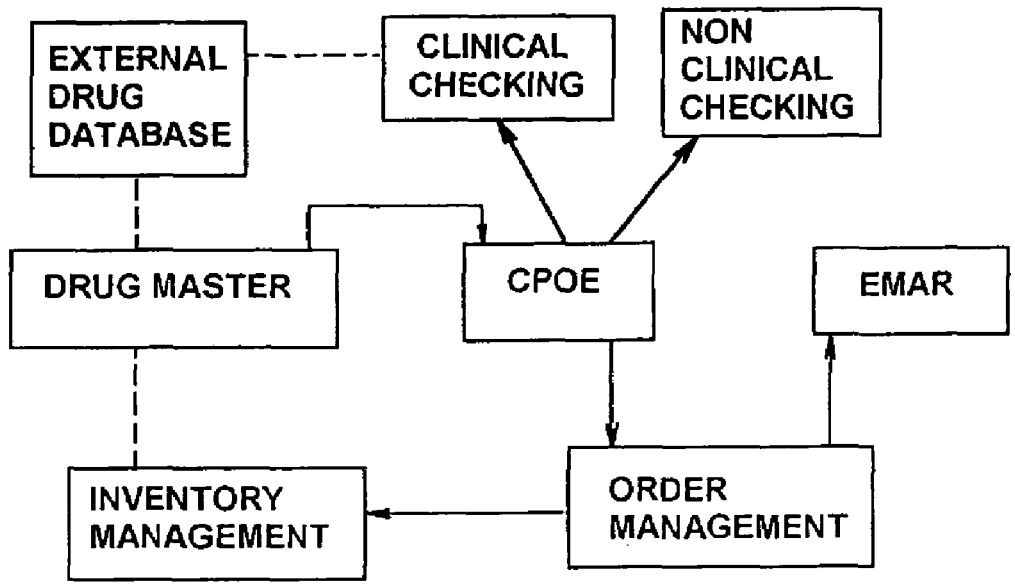
FIG. 7B is a schematic view illustrating an interrelationship of important functional areas of a system according to an embodiment of the present invention.
Figure 7C:
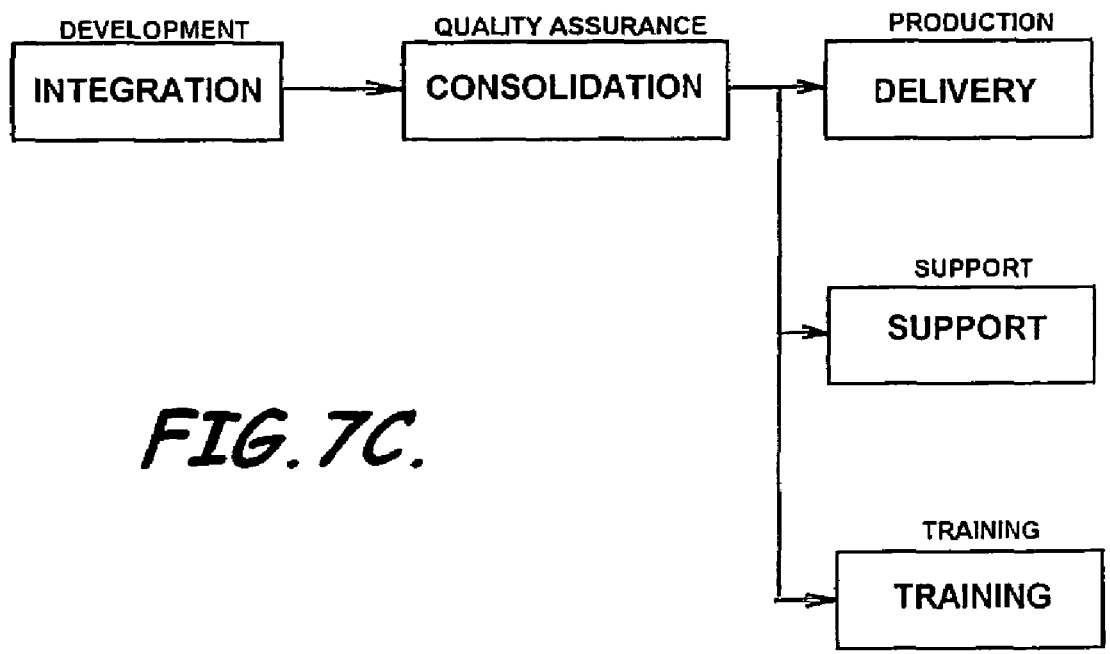
FIG. 7C is a schematic view of a preferred system and medication administration program product implementation methodology according to an embodiment of the present invention.
Figure 7D:
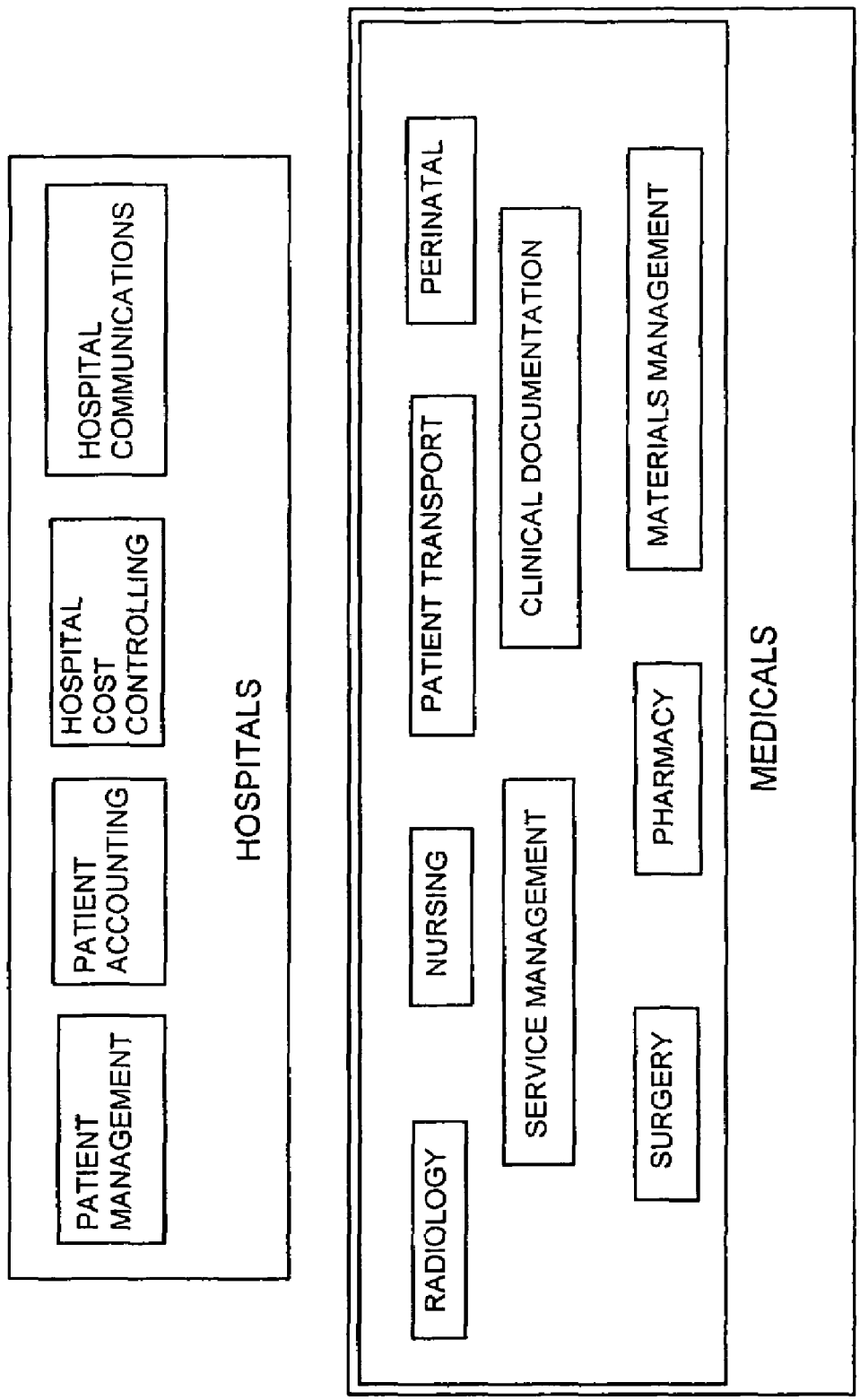
FIG. 7D is a schematic view illustrating major software functional areas after implementation of a medication administration program product according to an embodiment of the present invention.

In order to implement computerized physician order entry, various modifications and business procedures are preferably implemented in order to capitalize on the effectiveness of such form of prescription order entry. FIG. 7A illustrates a high-level view of a business processes including incorporation of various components and/or objects of the medication administration program product 53, methods of performing computerized physician order entry, and implementation methods, application methods including use of electronic medication administration records 45, and business methods capitalizing on the operational and managerial benefits of implementing computerized physician order entry, generally according to the preferred embodiment of the present invention, described in detail, below. FIG. 7B illustrates an interrelationship between some of the most important functional areas, according to an embodiment of the present invention. FIG. 7C illustrates a preferred system and medication administration program product implementation methodology, with FIG. 7D illustrating major software functional areas after implementation, according to embodiment of the present invention.

As shown in FIGS. 1-25, embodiments of the system 30 include a medication administration program product 53 and methods designed to deliver enhanced pharmaceutical services to a large institution (e.g. order entry and administration, and inventory control), such as a hospital 31, in a manner that significantly enhances the synergistic relationships of physicians, pharmacy personnel, and nursing unit members. The system 30 advantageously uses hardware and software to converge in real-time or near real time medication order management with inventory management to provide a significant efficiency increase and cost reduction for providing pharmaceutical services. The following areas are specifically detailed: Formulary and Other Master Data; Order Entry and Management; Clinical Checking, Non-Clinical Checking, and Drug Information; Filling, Preparation, and Dispensing—Inpatient; Filling, Preparation, and Dispensing—Outpatient; Medication Administration; Inventory Management; Costing; Reporting; and Label Printing.

Formulary and Other Master Data

The Formulary and Other Master Data functional area provides functionality to maintain the drug formulary 47 (drug master) which contains details on approved medications and related items. This functional area also includes an external drug reference master (external drug master) provided by a third-party vendor used to capture key information on drugs, their active ingredients and recommended administration routes, frequencies, and doses.

The drug formulary 47 is preferably stored in database 42 and includes medications approved by the institution (e.g. hospital 31) including compound medications, pre-packaged and re-packaged medications, dilutions, non-medication sundry items that are prescribed by physicians when prescribing medications (e.g. oral syringes, chemical ingredients used in compounding), special medications, and patient-own medications. An external drug database (e.g. First DataBank) contains a master list of medications available in USA and can provide expanded functions to perform clinical checks such as, for example, checks for drug interactions and dosage range checks. Other master data includes: patient allergies; patient immunizations; patient, physician and specialty related drug restrictions; medication order sets; IV and chemotherapy templates; recipes for compounded items; institutionally approved standard inpatient medication administration times; and intervention codes and texts.

The database 42 can include a master list of frequencies specifying administration times for various frequencies, a master list of administration routes, a list of administration routes for each medication, a master list of dosage forms, and a list of applicable dosage forms for each medicine. The database 42 can also include a recipe master which contains lists of ingredients, quantities, and preparation instructions for compounded medications, illusions, and extemporaneous preparations.

Each medication in the drug formulary 47 is preferably uniquely identified by a mnemonic. Further, medications in the drug formulary 47 contain information about generic/brand name, search terms, routes of administration, application device, default and min/max dosages, default inpatient and outpatient frequencies, label information, and instructions for preparation, where applicable. Narcotic, controlled, and psychotropic medications are separately categorized.

In an embodiment of the present invention, the drug formulary 47 also includes: drug indications; therapeutic classification; prioritized label warnings; and counseling messages, data available from external sources (e.g., First DataBank). Drug indications identify drug products available to treat a specific condition with emphasis on drugs in the drug formulary 47. Therapeutic classification provides drug classification with various levels to aid in formulary selection including therapeutic substitution.

The drug formulary 47 also identifies medications that are used as "Triggered Drugs," used to treat allergic reactions to drugs. The drug formulary 47 also includes over-the-counter medications which do not require an outpatient prescription but are processed through the outpatient pharmacy window, and which are preferably provided non-order specific labels in order to expedite issuance.

Order Entry and Management

The Order Entry and Management functional area provides functionality to perform: order entry including computerized physician order entry, non-computerized physician order entry, order verification, clinical and non-clinical checks, and intervention logging; and order maintenance including: order changes (e.g., extend, suspend, resume, discontinue, and void), order status management, automatic stop notification, label printing, inventory and billing adjustments, and workload statistics.

The medication administration program product 53 includes instructions to perform operations which support computerized physician order entry (CPOE) which includes order entry by physicians or physician agents. Orders entered by a physician (i.e. via CPOE) are given a conditional status and are reviewed and verified by a pharmacist before being prepared (as needed) and filled. Medication orders 57 entered by physician agents are subject to physician confirmation before pharmacist review. Non-CPOE orders (e.g. traditional written prescription) can be entered by pharmacists simultaneously during order verification. The medications in the drug formulary 47 are preferably linked to the external drug master to provide additional drug information and to perform clinical checks, and are linked to a material master 93 to support inventory management functions.

When verifying an order, advantageously the pharmacist can view all clinical and non-clinical alerts encountered by the physician along with any override reasons posted with the alerts. The verification process can include the clinical and non-clinical checks to alert the pharmacist to any new conflict conditions. The pharmacist will have the ability to post override reasons for new conflicts. Further, the verification process can allow the pharmacist to modify an order and substitute a drug item upon consultation with the prescribing physician.

The medication administration program product 53 supports the varying types of medication orders including: routine inpatient medication orders; oral syringe medication orders; compounded medication orders; titrational (sliding scale) dosing orders; routine outpatient prescription orders; and IV medication orders including large volume (continuous), intermittent (piggyback), syringe, and specialized large volume (TPN) orders. Discharge and "leave of absence" orders can also be supported for inpatients.

The medication administration program product 53 provides various graphical user interface display screens including search data, data entry, and data recall templates, which provide ready access to store data and help provide an intuitive computerized physician order entry procedure. For illustrative purposes only, a computerized physician medication order entry according to the preferred embodiment of the present invention will be described. Note, as will be understood by those skilled in the art, the following graphical user interfaces described in FIGS. 9A-12 are formatted according to but one example. That is, for example, the "buttons" displayed on the GUIs can instead be displayed as "drop-down menus" or "check-boxes" and vice versa.

As medication orders are associated with a patient, the first step in the order process involving a routine order generally includes accessing a patient using a "find patient" search (see FIG. 9A) which provides an option to search various demographic data, or select or highlight the patient from a patient list. Once found, the user can view various patient demographic data, preferably accessed from a patient master data record 46 stored in database 42 (FIG. 6). The user can then view the patient medication profile (see FIG. 10) accessed from the patient medication profile records 43. In the preferred embodiment of the present invention, the user can select from a medication profile screen 100 either an outpatient medication profile 101, inpatient medication profile 103, or an outpatient/inpatient medication profile 105 which advantageously provides a consolidated listing of patient medications, thus providing the user an intuitively complete review of the patient's medication profile.

Generally, the next step can include the user selecting a "create order" button 107. Responsive to such selection, the medication administration program product 53 provides a CPOE search screen 110 (FIG. 11), which provides the user an option to search various medication demographics 111, accessed through use of the "find" button 113. The search is preferably primarily directed to the drug formulary 47. Once the desired medication (drug) is located, the user can select the desired medication through use of the "order" button 115. Responsive to such selection, the medication administration program product 53 provides a CPOE order screen 120 (FIG. 12) which displays the medication order entry form 55, having a patient demographic data section 121, an order header section 123 including detailed ordered drug information, and an order description section 125 including more detailed drug information. The order description section 125 includes tabs 127 which provide order details that depend on the type of drug ordered. If the order is an antibiotic or narcotic, a drop-down menu, reason code selection, or text entry field can be provided to enter a reason for usage. Prior to saving the medication order, the user can be provided a "check" button 129 to verify completeness of the order.

During the computerized physician order entry (FIGS. 9A-12), the user may encounter an alert or warning indicating failure of either a clinical or non-clinical check, described later. Depending upon the type of alert or warning, the user is provided a selection termed an "intervention," described later, to override the alert or warning and is provided a selection menu to enter an intervention code and/or is provided a text entry field to explain the reason.

For most medication orders a single medication is selected from the drug formulary 47. This medication may be supplied by a drug manufacturer or the item may be prepared in the pharmacy using other formulary items. For some orders (e.g. patient's own medications), a free-form text medication description is entered on the order and the ingredients are specified by selecting one or more items from the drug formulary 47. Multiple ingredient IV orders, TPN's and compound medications generally require such selection of multiple formulary items. The formulary item selection can be by generic name, drug description, brand name, mnemonic key, agent, ingredient, drug type, medication group, or therapy class. The mnemonic key is a user preselected unique code assigned to each medication and that uses industry standard abbreviations to combine generic name strength and route to identify formulary items.

By selecting "order template" (FIG. 11), formulary items can be selected by pre-defined sets of orders and recipes. Such templates preferably include: compounded medications which provide predefined sets of ingredients and which can populate a compound building array, IV templates which are predefined IV's and which can populate an IV ingredient array along with the IV type and IV set attributes; and order sets which are predefined sets of orders and which can include most order attributes for each element of the set. When an order set is selected, the physician or pharmacist can select/deselect some or all the medications on the list to formulate the medication order.

Figure 12:
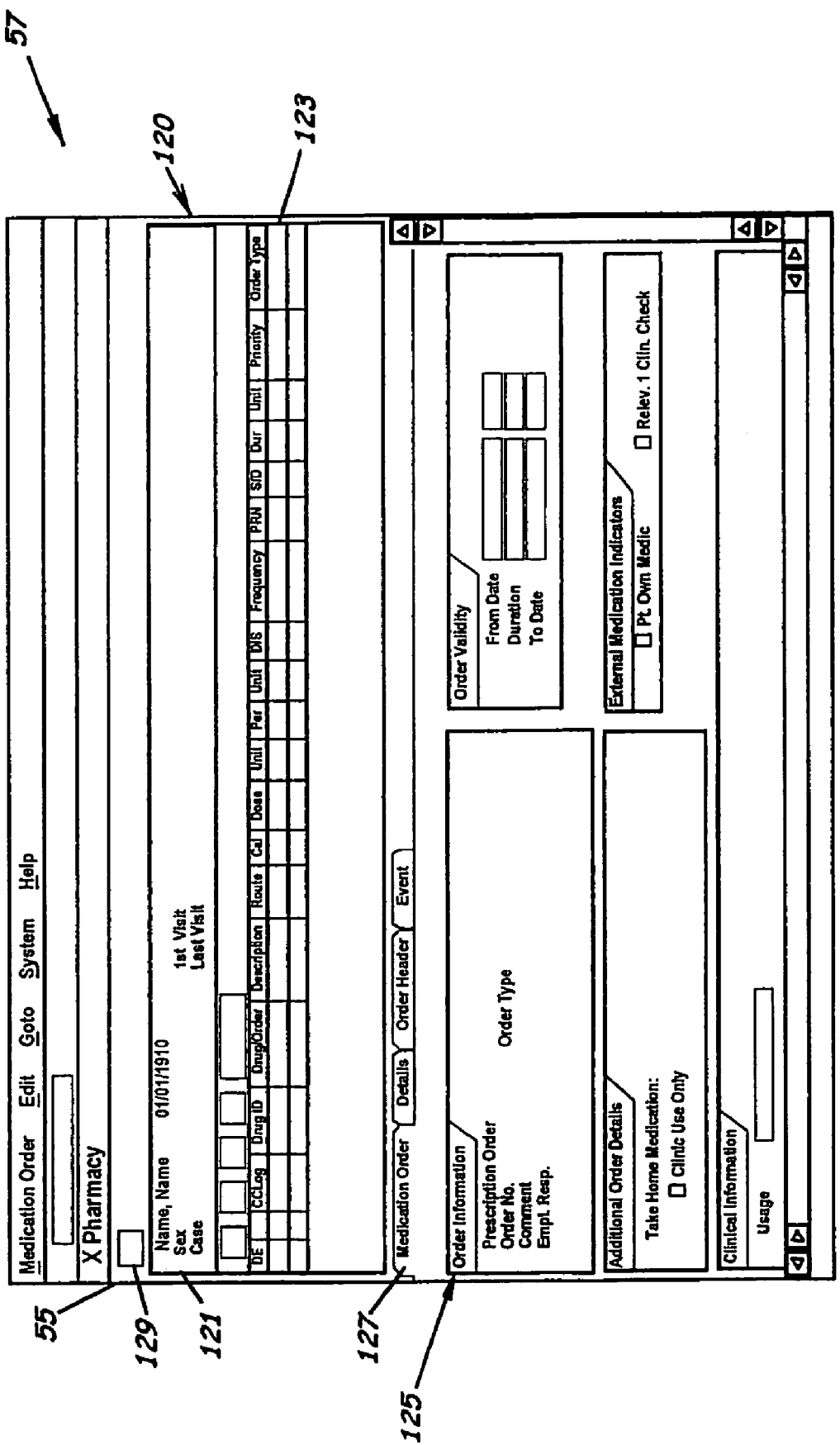
FIG. 12 is a schematic view of a graphical user interface according to an embodiment of the present invention.
Figure 13:
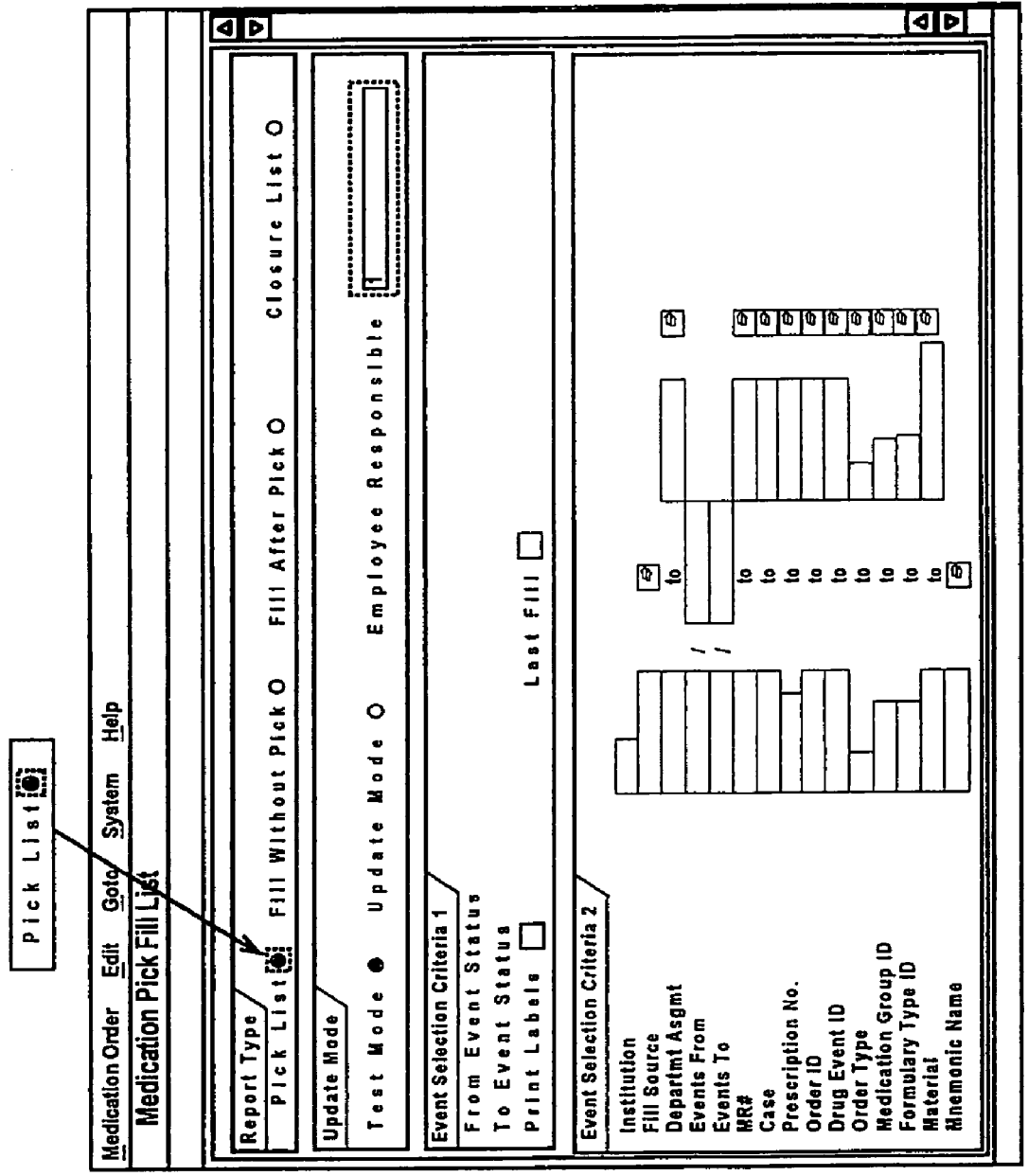
FIG. 13 is a schematic view of a graphical user interface according to an embodiment of the present invention.
Figure 14:
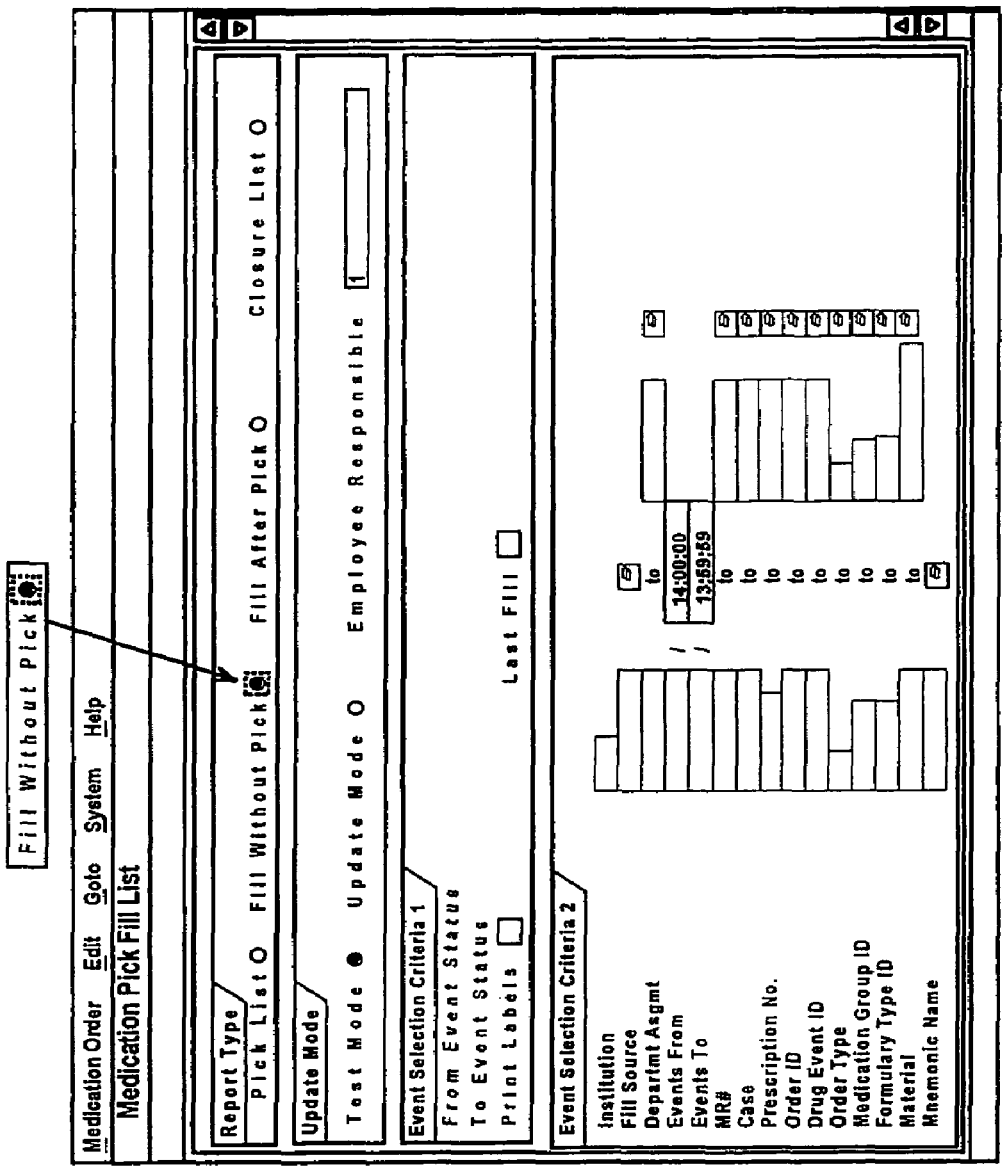
FIG. 14 is a schematic view of a graphical user interface according to an embodiment of the present invention.
Figure 15:
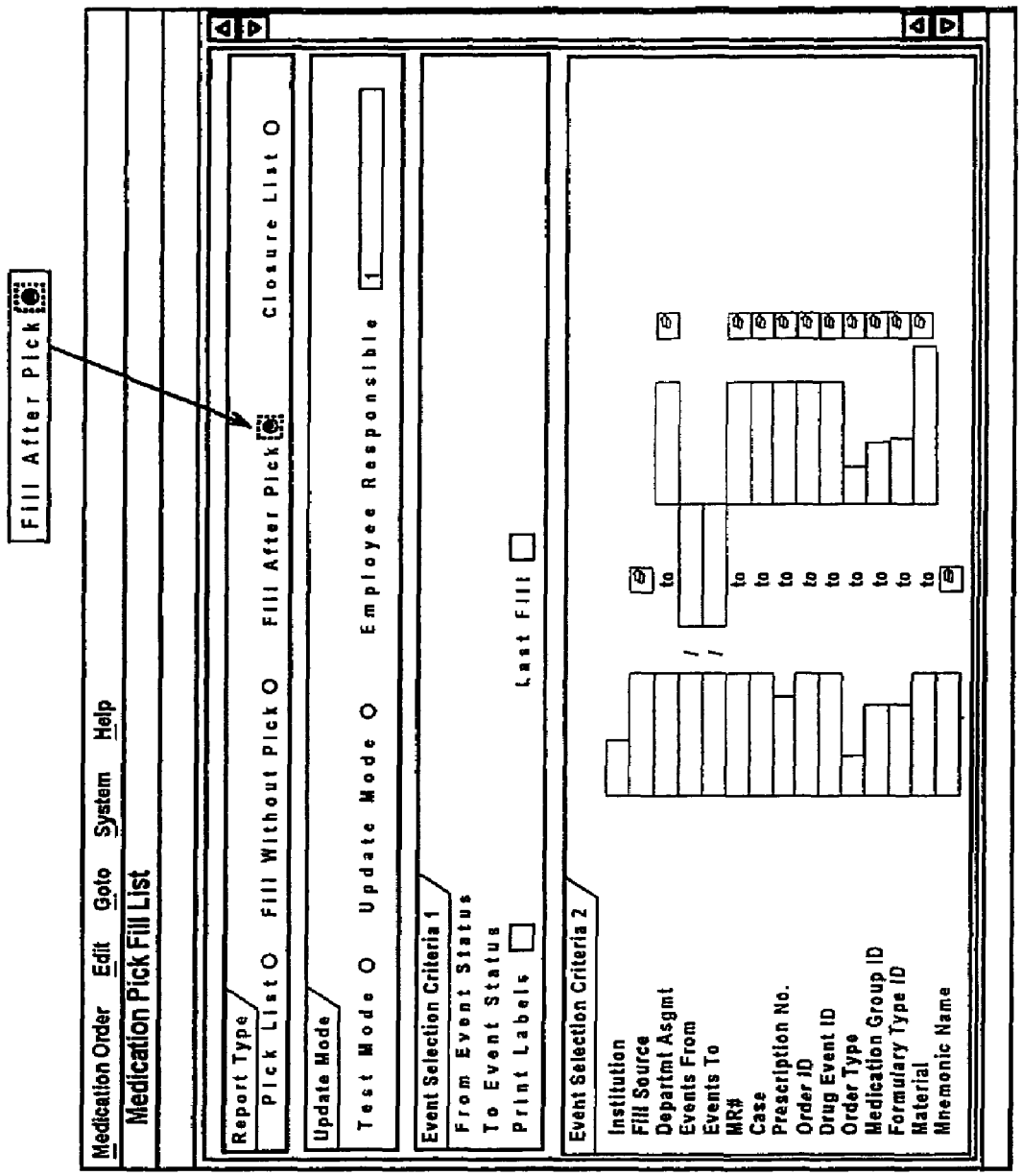
FIG. 15 is a schematic view of a graphical user interface according to an embodiment of the present invention.
Figure 16:
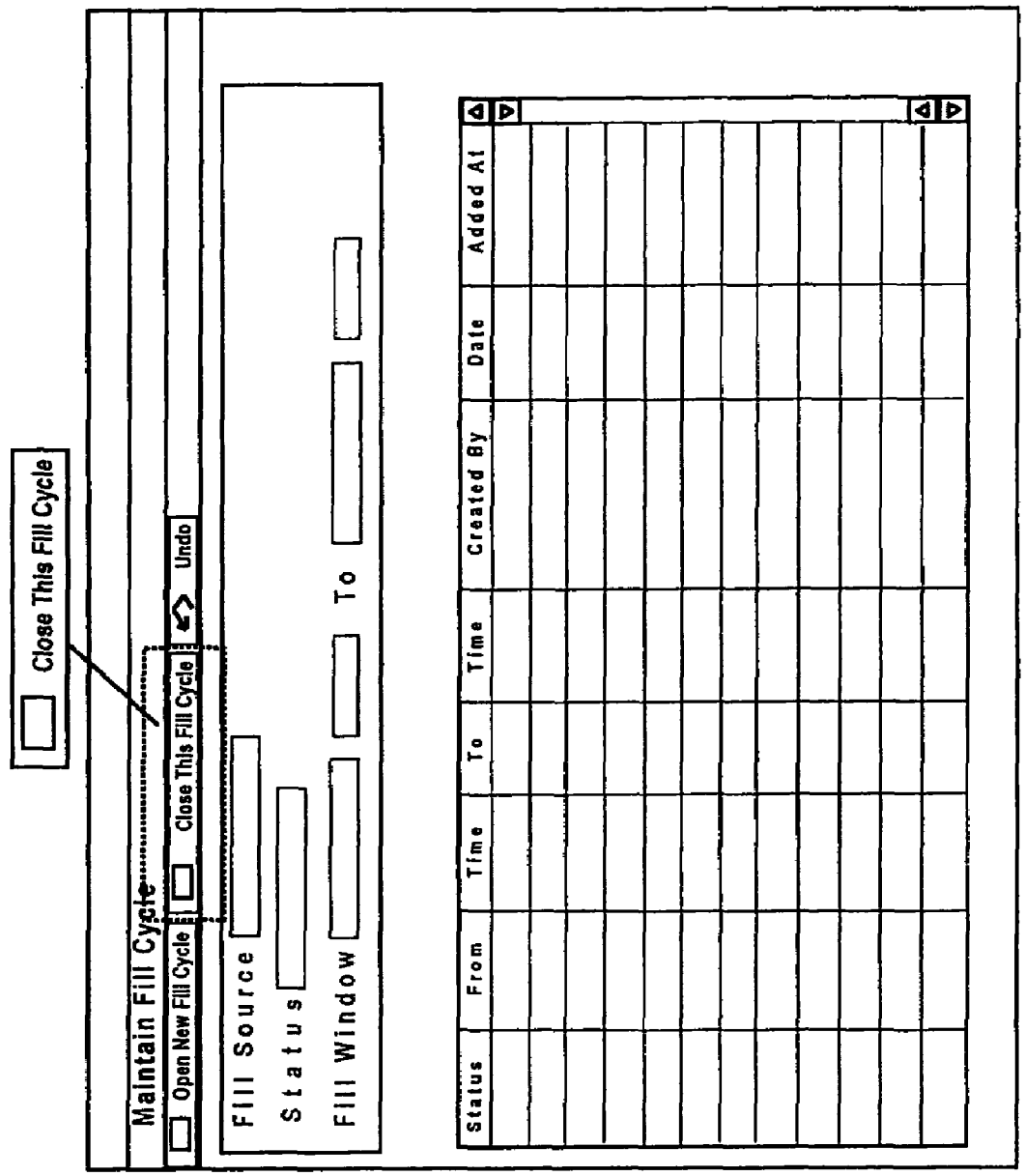
FIG. 16 is a schematic view of a graphical user interface according to an embodiment of the present invention.
Figure 17:
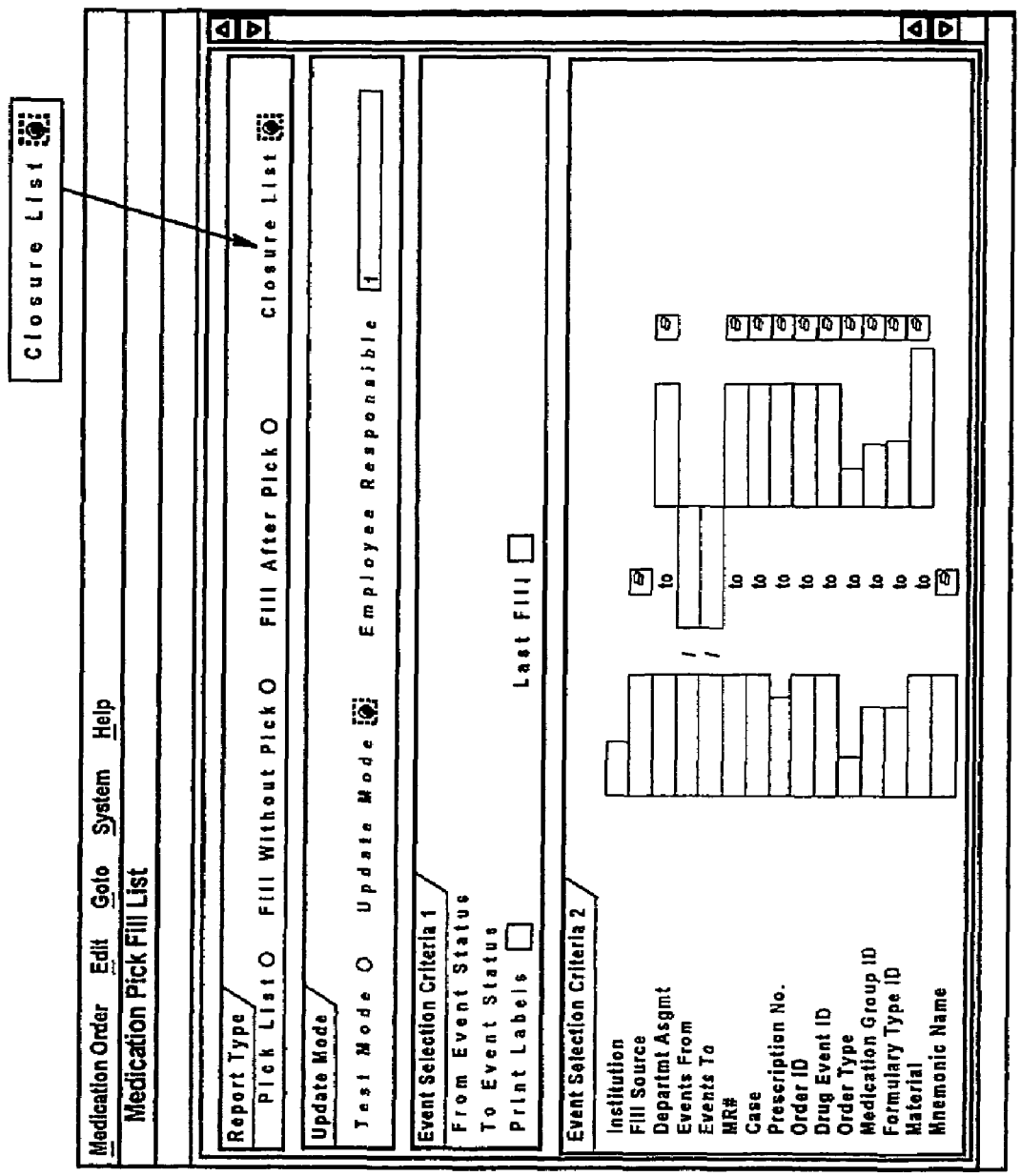
FIG. 17 is a schematic view of a graphical user interface according to an embodiment of the present invention.
Figure 18:
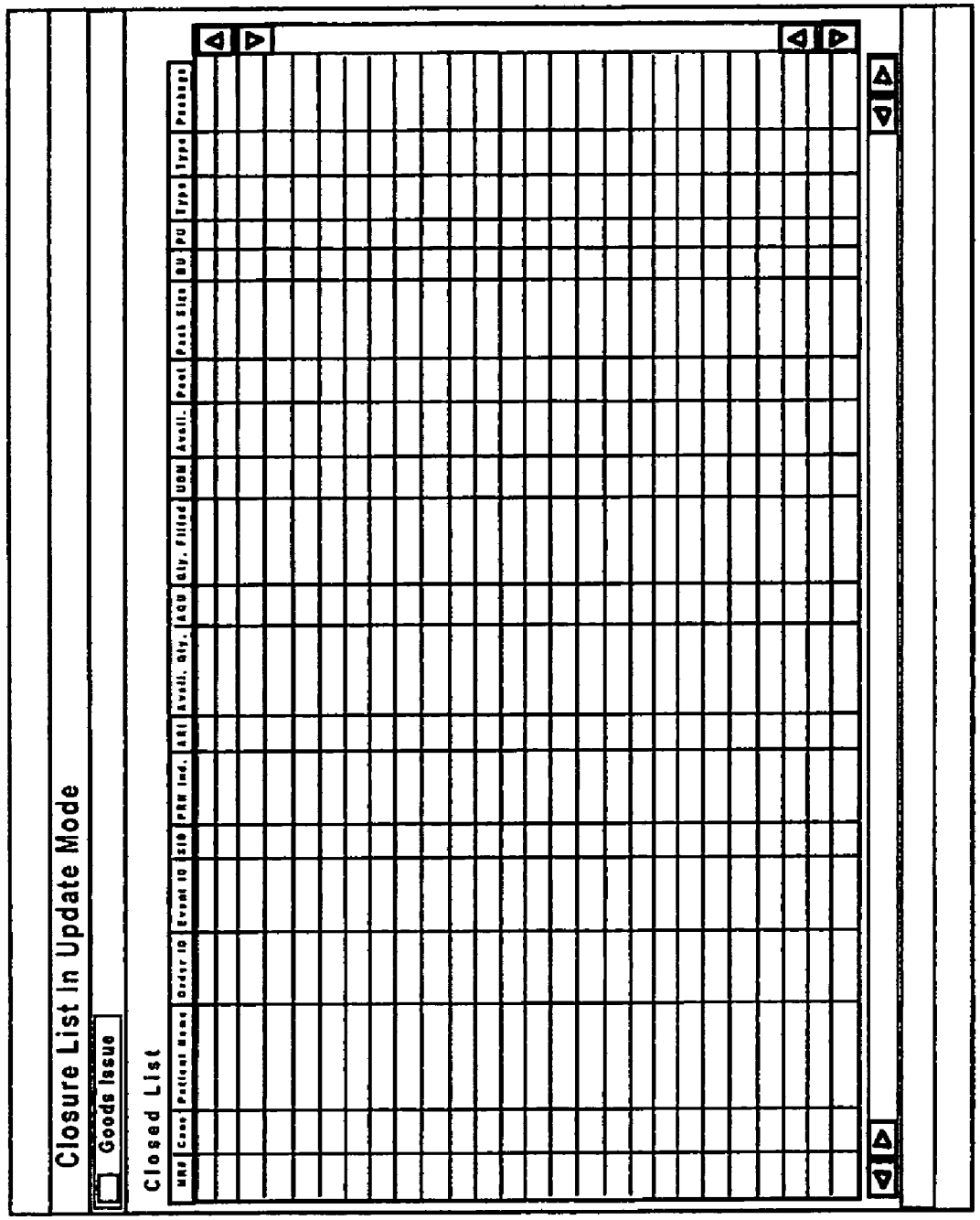
FIG. 18 is a schematic view of a graphical user interface according to an embodiment of the present invention.
Figure 19:
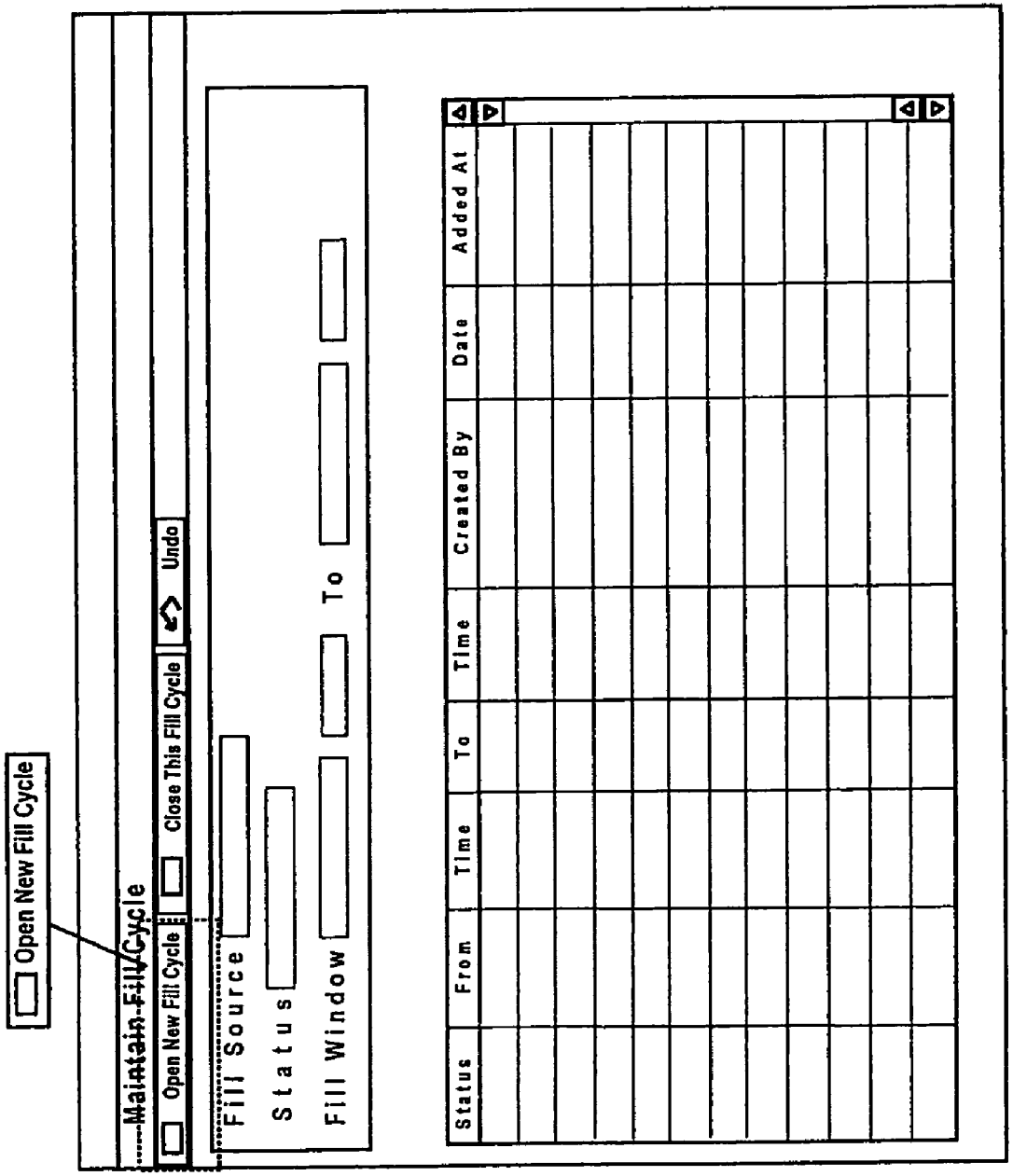
FIG. 19 is a schematic view of a graphical user interface according to an embodiment of the present invention.
Figure 20:
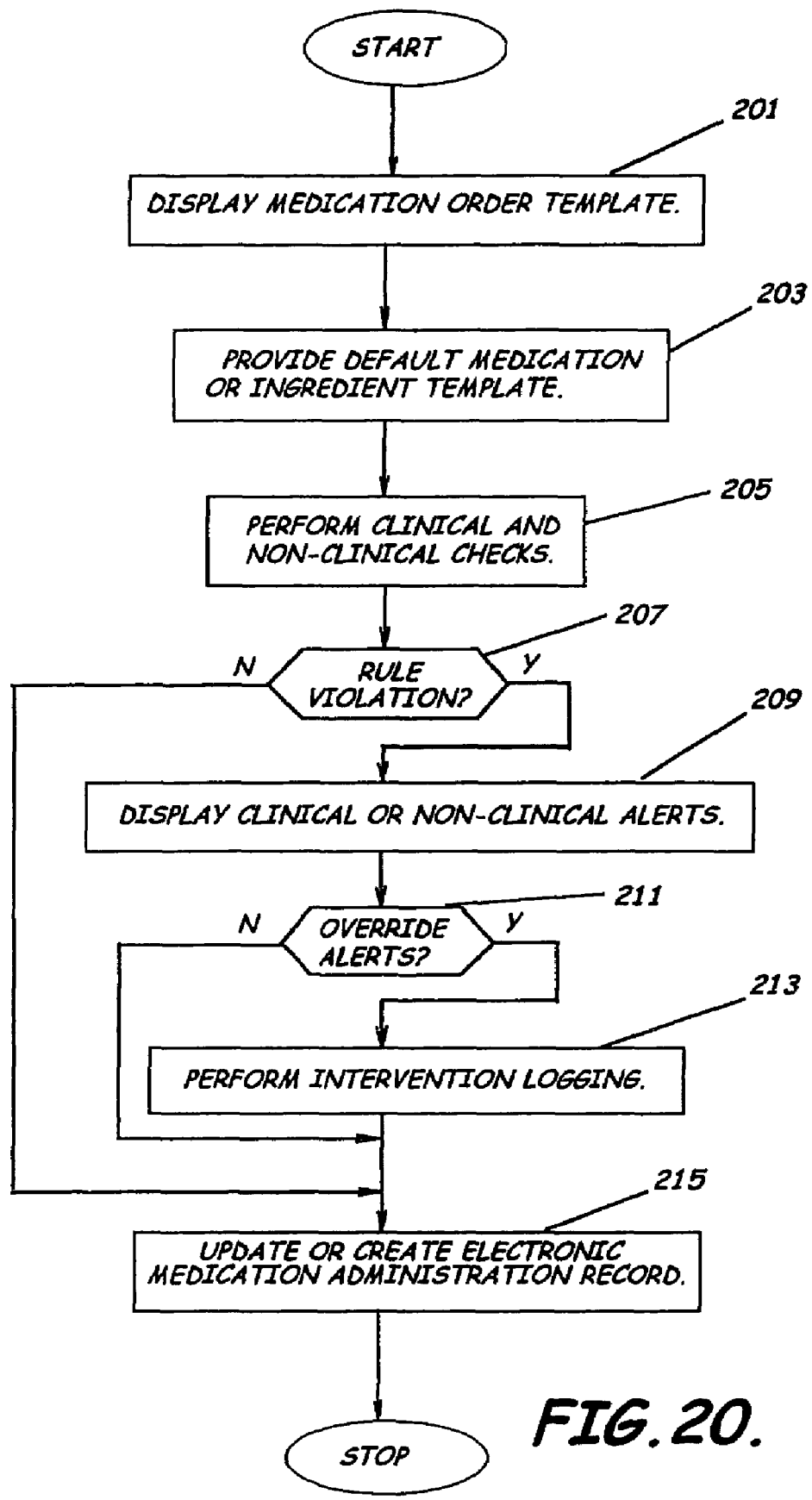
FIG. 20 is a schematic flow diagram of a method to enhance pharmaceutical order entry medical personnel within a medical institution according to an embodiment of the present invention.

The common attributes of a medication order are drug, dose, route, duration, and frequency (see FIG. 12). For each medication, default values for these attributes can be maintained in the drug formulary 47 and assigned automatically to the order when the drug formulary item is selected. Such values can be overridden at the time of order entry. The medication administration program product 53, when integrated appropriately with a third party database, also provides, through the GUI, access to additional dosing recommendations including those for minimum and maximum dose, lifetime cumulative dosing, pediatric dosing, neonatal dosing, and/or geriatric dosing along with access to AHFS Drug Monographs® and, optionally, Enhanced Therapeutic Classification (ETC)® monographs, e.g., from First DataBank, which are integrated and accessible not only during order entry, but during verification, dispensing and medication administration. Note, MedTeach® Patient Education Monographs, easy-to-use written instructions on drug therapy, are also preferably available to help provide detailed patient education information to offer patients. Note also, in the preferred embodiment of the present invention, properly formatted foreign language (e.g. Arabic) monographs could be easily integrated and accessible.

There are some other attributes that are unique for inpatient and outpatient orders, and those that are unique to each order type. For example, for an outpatient order the default frequency need not include specific administration times as might an inpatient order. For an inpatient order, the frequency can be used to calculate a number of doses needed to be sent to a nursing unit to go on an exchange cart 143 already on a nursing unit floor. Also, for example, in an inpatient order, providing an order priority can be beneficial, e.g. STAT, ASAP, NOW, and routine, with routine as default. Other attributes can include a PRN indicator, PRN par level (inpatient only), start date and time, stop date and time, stop after [parameter]—e.g. days or dose), dose now (inpatient only), medication fill source, physician, consulting physician, reason for usage, label type, and number of labels.

A medication may be prescribed for a specific number of doses. By entering a whole number value for "stop after doses" the stop date and time can be automatically calculated by extending the administration schedule out the specified number of doses. A medication can be prescribed for a specific number of days. By entering a whole number value for "stop after days" the stop date can be automatically calculated by adding the "stop after days" to the start date. The stop time will be set to the start time. Depending upon the reason for usage, the automatic stop date for an antibiotic or a narcotic is calculated using a "stop after days" algorithm.

Advantageously, the "doses now" attribute provides the number of doses that the pharmacy must supply to an inpatient ward before the next cart 143 exchange. Correspondingly, the fill source need not be the same for an initial "now" dose. Thus, in this example, two filling sources can be identified at medication order entry, the "now" source and the "subsequent dose" source. The values for these sources can be, for example, "Pharmacy" (the pharmacy); "Satellite" (a satellite pharmacy); "Floor" (floor stock 141 in a nursing unit or clinic); and "ADDS" (automatic dispensing system/device 91 in a nursing unit or clinic).

Other more unique attributes are within the scope of the present invention. For example, narcotic orders require a prescription number as mandated by federal regulations. Also, for example, sliding scale doses (also known as Titrational dosing) allow the physician to prescribe a tapering dose (up or down) over a period of time, e.g., 100 mg for 3 days then 50 mg for 3 days and then 25 mg for 2 days. These medication orders will accept all the standard attributes except that an array is used to enter units per dose, frequency, start and stop times for the individual dosing steps. When building the dosing array the user enters a number of doses or number of days for each step so that the medication administration program product 53 can calculate the stop time of that step and the start time of the next.

Physicians can prescribe medications that require compounding of multiple ingredients. The ingredients of a compounded medication can be automatically entered by selecting a pre-defined recipe or template, or entered on an ad hoc basis by selecting each ingredient from the drug formulary 47. The ingredient array includes the item and the units per dose for the item. Units per dose for each ingredient is generally modifiable whether the compound is assembled from a pre-defined recipe or on an ad hoc basis.

Physicians can also prescribe intravenous medication orders which include three basic classes: continuous infusion (large volume IV); intermittent infusion (piggy back IV); and syringe (injectable IV). According to the preferred embodiment of the present invention, these categories further break the classes down by type. Each type is assigned a class, description and a label. Types could optionally be assigned IV sets and label text fields. The type designations allow the IV's to be grouped by where and when they are filled. All IV types may require multiple ingredients. Ingredients can be selected from the drug formulary 47 one at a time using the same selection process as medications. Alternatively an IV template can be selected and the ingredients will be populated automatically. The dose of each ingredient is modifiable by changing the units per dose or the volume. The medication administration program product 53 includes a dose volume calculator so that the volume of each ingredient is accumulated to determine the total volume of the IV medication order.

IV orders have some additional attributes that are specific to the class: interval (time period over which a single IV preparation is administered); Ml per hour (rate of administration); total volume (total volume of each preparation); bottle (number IV's required based on the administration parameters); infuse over (time period over which each dose is administered); IV set (materials e.g. tubing etc. required to administer the IV); and alternate with [another IV].

Total Parenteral Nutrition (TPN) IV's are a special type of continuous IV that require calculations to balance the dosage of all the active ingredients. They are prepared in a GUI window (not shown) in worksheet fashion from several base ingredients which the ordering physician prescribes.

Chemotherapy IV's are a special type of typically intermittent IV that require special handling because of their toxicity. They are double bagged, and thus, require two sets of labels. The chemotherapy orders have additional order entry requirements. At the time of order entry the prescribing physician determines a treatment regime. It can include other order types. The physician maps the administration schedule that includes the order of administration of the medications in the treatment and the calendar days of administration. The plan also identifies required lab tests and the result value range which will allow administration. On the administration plan, the actual test results are recoded as well as administration data. The schedule is updated whether the treatment is administered or not. Lifetime treatment doses of certain chemotherapy drugs are tracked by a tracking function of the medication administration program product 53.

Alternating IV's are a series of continuous IV's that alternate in sequence. For example, after surgery D5W and D5NACL solutions may be alternated. In the preferred embodiment of the present invention, up to four IV orders can be contained in an alternating set, though a different number is within the scope of the present invention. Each IV in the set can have more than one administration when it occurs in the sequence. For example, the sequence may prescribe as two D5W and the one D5NACL, so the sequence would be D5W, D5W, D5NACL, D5W, D5W, D5NACL, etc.

Figure 10:
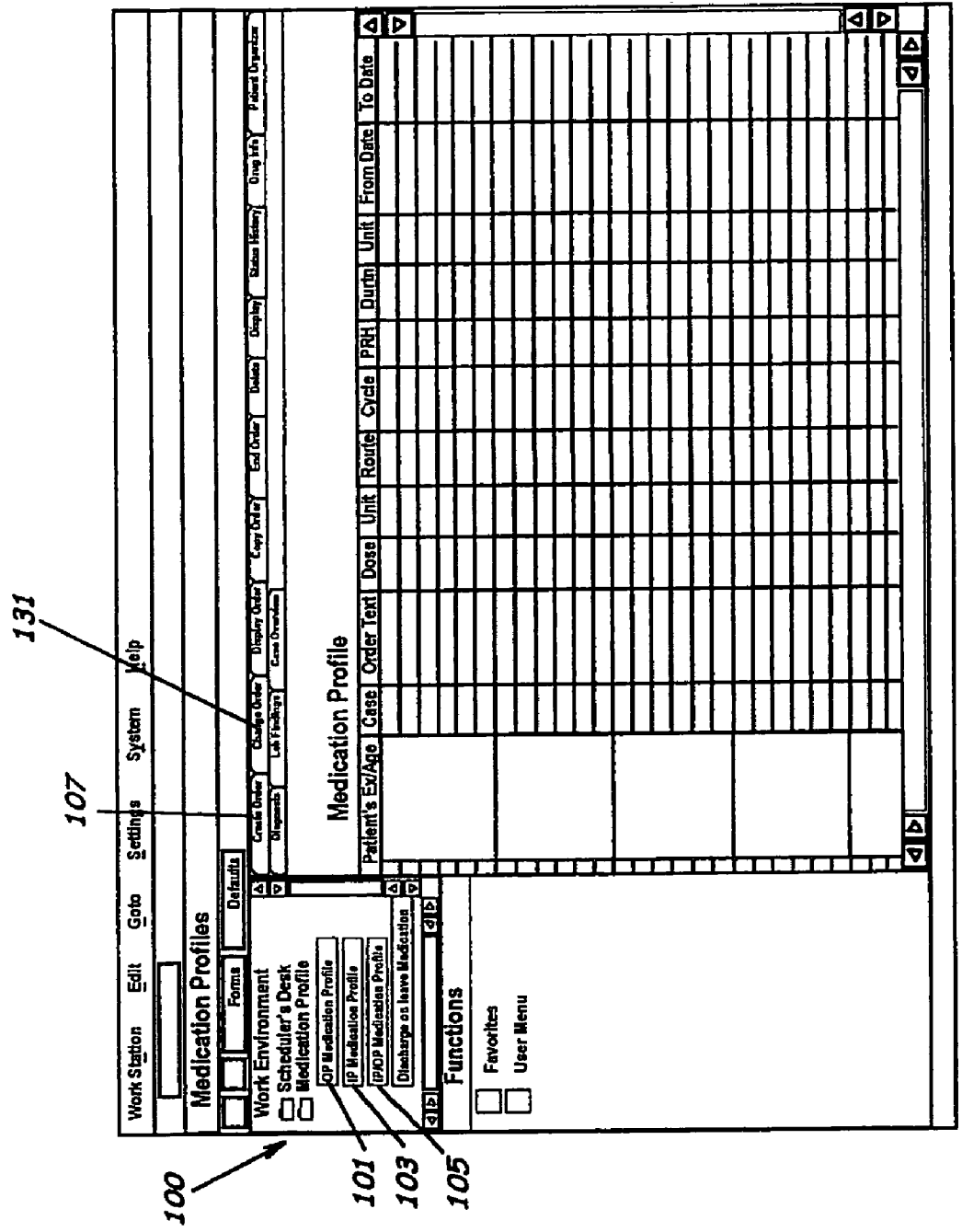
FIG. 10 is a schematic view of a graphical user interface according to an embodiment of the present invention.

Medication order status can be managed by "change order" functions of the medication administration program product 53, described below, selectable through use of the "change order" button 131 (FIG. 10). In the preferred embodiment of the present invention, orders are assigned the following status attributes: active; discontinued (DC'd); canceled; suspended; expired (outpatient only); and conditional (awaiting pharmacist verification). A discontinue (DC) function is provided to discontinue active and suspended orders. When an order is DC'd, the stop date and time is defaulted to the current date and time but can be set to a future time up to a parameter driven limit. E.g. an order can be DC'd one hour from the current time. In the case of alternating IV's when one of the order set is DC's all of the order set should be DC'd. Correspondingly, a cancel function cancels orders which have had no doses dispensed to the patient. When an order is cancelled, a text entry field or reason code drop-down menu is preferably provided so that a reason can be entered. Further, for an outpatient order, an indication is provided as to whether or not the item will be restocked.

A resume function resumes suspended orders. Functionally this changes the order status back to active. When an order is resumed an input field is provided to enter a start time (for resumption). The default is preferably set to that of the next scheduled dose after the system time when the resume function is performed. An extend function is provided to extend orders which are about to reach a stop date. The stop date and time will be changed to a future time. In the preferred embodiment of the present invention, this function is set so that it cannot be implemented on an order having a "hard" stop date. Hard stop dates are generated by "reason for use" criteria for narcotics and antibiotics.

According to the preferred embodiment of the present invention, certain events are established as triggers to cause an order status change, automatically. For example, a patient discharge will act as a trigger to cause: all active orders to be treated as if discontinued at the time of discharge; an "update fill" report to automatically adjust medication cart requirements; the electronic medication administration record 45 for the discharge patient to no longer show scheduled doses; and disabling of all order modification functions except with respect to the discharge order. A patient death has the same effect as a patient discharge. All active orders may have to be discontinued automatically.

An "order modify" function allows active or conditional orders to be modified. In the preferred embodiment of the present invention, changes to dosage will cause the order to be rewritten in order to document the history of the medication order. In general, non-dosage related attributes such as label type or administration time are treated as a simple change. For example, administration times are modifiable without rewriting the medication order as long as the actual frequency is not changed. Future scheduled administration times will reflect changes on "fill" reports and prospective electronic medication administration record data, historical electronic medication administration record data reflecting actually administration times. If the administration time is for an IV, any other IV using the same order "line" will automatically be adjusted. When an order is modified, the medication administration program product 53 preferably provides both an automatic audit trail and either a drop-down menu or text entry field for entering either a free-text explanation or coded reason for the change.

In the preferred embodiment of the present invention, a charge nurse at each nursing unit monitors a nursing unit-level electronic medication administration record 45 for new and changed orders. The medication administration program product 53, preferably as part of the "create order" and "change order" functions, causes the display and automated highlighting of a new and changed orders on the nursing unit-level electronic medication administration record 45 on the hospital nursing unit computers 81, and/or printing on the nursing unit printer 87 of the new or changed order or a report reflecting such order.

The medication administration program product 53 advantageously also includes other order-related functions to improve pharmaceutical service efficiency through use of the computerized physician medication order. For example, it is not unusual for a medication dose or doses to be lost or spilled. Rather than creating an entirely new order to replace the lost or spilled medication, an additional dose function is provided which allows inventory to be decremented, optional billing to the patient, optional label printing, and preferably a text entry field to enter free text or a coded reason explaining the requirement for the additional dose or doses. Also for example, an automated stop notification function is provided to provide a stop order report to either a nursing unit or a prescribing physician identifying inpatient medication orders that are about to expire. The automated stop notification function also provides automated stop notification to a physician responsible for a medication order having stop times falling within a parameter driven number of hours (e.g. 24). In the preferred embodiment of the present invention, an automatic stop notification physician work queue is provided, the items of which can be displayed on the hospital physician computer 61. Advantageously, to prevent inadvertent expiration of a medical order, the work queue provides the physician a preferably mandatory option to either extend the medication order or positively confirm the stop time.

Other medication order-related functions are provided according to embodiments of the present invention. A copy order function is provided to allow a user to effect a modification of a medication order or to produce a copy of a medication order to be used as a template for a new order. Advantageously, the copy order function is a "smart" copy in that if the formulary item has been inactivated since the source order was originally entered, it may not be copied. Preferably, the medication administration program product 53 defaults to notify the user of such occurrence. A reprint label function is provided to allow a user to reprint labels either by computer or terminal where originally initiated, by printer where originally printed, by patient, or by case. A billing adjustment function, closely related with the modify order function, is also provided to allow the number of doses for which a patient discharge to be adjusted. Advantageously, adjustments can be made at the ingredient level. Also, advantageously, when adjustments are made to inventory, the user can be prompted to verify the inventory location affected and to provide a reason for such adjustment. A workload statistics function automatically captures all orders to provide pharmacy management statistical information such as, for example, the number of patients served, the number of orders added by order type, interventions by type, number of doses dispensed, and number of doses returned.

Advantageously, the medication administration program product 53 provides profile-based functions that use existing medication orders on the patient profile as input. For example, an admission function is provided to display inpatient and outpatient medication orders from a previous case or user specified time period which provide a template for new orders. A discharge function displays all current active orders to allow a user to select which orders should be prescribed as take-home medications, the selection of which trigger a standard take-home order entry process. A leave of absence function is similar to the discharge function, except that it further requires a time the patient will enter a "leave of absence."

A pre-op function is provided which displays all active orders with a checkbox for each order indicating which orders should be suspended. In the preferred embodiment of the present invention, all oral medications are automatically checked. The physician reviewing the list can select or deselect orders to be suspended, and can accept the default time or provide the selected time the order should be suspended. Further, in the preferred embodiment of the present invention, the pre-op function is linked to "scheduled surgery" to provide an automated date and time input and automatic cancellation if the scheduled surgery is canceled. Correspondingly, a post-op function displays all orders for oral medications that were suspended in the pre-op process to allow a user to initiate either the resume function, DC function, or modify function, on such suspended orders.

Clinical Checking, Non-Clinical Checking, and Drug Information

Medications orders are subject to a variety of clinical interaction checks and non-clinical institutional-specific checks at the time of order entry, order verification, and/or medication administration. In addition, clinical interaction checks may be invoked at the time of medication administration. Alerts (e.g. error, warning, or info messages) generated during these checks may be overridden by physicians, pharmacists, and nursing unit members identified as having necessary authorizations, with appropriate intervention logging.

In the preferred embodiment of the present invention, the medication administration program product 53 incorporates the following clinical check modules: dosage range check module; min/max dosing check module; neonatal and infant dosage range check module; duplicate therapy module; prescriber order entry module; drug-disease module; drug-drug interaction module; intravenous (IV) compatibility module; drug-lab interference module; drug-lab results module; drug allergy module; drug-alternative therapy module; drug-food interaction module; and prioritized label warnings module.

The dose range check module identifies safe dosage levels and frequency of administration based on patient-specific parameters, and can check a dose against low, high or maximum dosage levels, and recommend a dosage range for a particular drug, specific to patient age and drug indication, if available. The min/max dosing module provides a non-patient specific reference for the most frequently prescribed drugs, and for clinical screening of adult, geriatric and pediatric individual daily doses. The neonatal and infant dosage range check module provides dosage range information for neonates and infants up to one year of age. The duplicate therapy module screens orders against the current patient medication profile to check for potential duplication of drug therapy, drug ingredients, and prescription refills. The prescriber order entry module is used to integrate a common dosage order database of standardized inpatient and outpatient medication orders into the computerized physician order entry to help prevent prescribing errors. A pregnancy and lactation module can flag those identified as, or potentially as, pregnant or lactating.

The drug-disease module is utilized to identify drug products available to treat a specific disease condition and helps assess drug use in patients who have specific diseases or health-related conditions, or who have had certain procedures or diagnostic tests. The drug-drug interaction module is utilized to provide alerts to prevent harmful clinically significant drug-drug interactions. The intravenous compatibility module provides comprehensive data to enable automatic screening of intravenous drug admixtures for physicochemical compatibility or incompatibility. The drug-lab interference module identifies potential adverse effects of drugs on lab test results. The drug-lab results module integrates review of lab results before ordering and administration of medications. The drug-allergy module, accessible from the medication profile or order screens, identifies potential allergic reactions and cross-sensitivities between drugs, specific known patient allergies, and can identify adverse drug events and provide detailed information including documentation history. Allergy status is preferably listed as: active, inactive, rejected, and info only. The drug-alternative therapy interactions module provides alerts for drug interactions with herbal, dietary supplements and other alternative-therapy agents. The drug-food interaction module provides alerts to help prevent harmful, clinically significant drug-food interactions, safe dosage levels, and frequency of administration based on patient-specific parameters. The prioritized label warnings module provides prioritized drug warning labels to minimize adverse drug events. The warning can be viewed during computerized physician order entry, at medication administration time, or during order dispensing.

In the preferred embodiment of the present invention, the medication administration program product 53 provides the following non-clinical checks: patient eligibility check; duplicate medication check; medication availability check; drug restrictions check; and refill restrictions check. The patient eligibility check determines if a patient is a registrant or non-registrant, and whether patient attributes are compatible with predetermined institutional rules to qualify for the medication order. The duplicate medication check examines the current patient medication profile to check for duplication of medications. A duplicate medication situation may occur when two physicians prescribe the same medication for a patient. The medication availability check examines inventory levels for stock-out conditions during order entry and during order refills. For inpatient orders, the check should be set to verify that at least one day's supply is available. For outpatient orders, availability of a full course supply should be checked. In the preferred embodiment of the present invention, the medication order 57 can be saved even when there is a stock-out, as the filling pharmacy may be able to procure medications from other locations depending on availability. Orders with no-stock, however, are placed on a separate pharmacy queue for special handling and inventory management.

Certain medications in the drug formulary 47 may be restricted to certain patients or may only be prescribed by certain physicians and specialties. This data is maintained as part of the formulary master data. According to the preferred embodiment of the present invention, to prevent potential conflicts of interest, a physician may not prescribe medications for himself or a family member. During computerized physician order entry, the order data is checked against the drug restrictions for patient, physician and specialty restrictions. Appropriate alerts will be generated. Under circumstances when no other physician is present, such as, for example, in an emergency situation (EMS), the physician can be allowed to prescribe medications to family members. This is accomplished by overriding the alerts with intervention logging and appropriate privileges.

Advantageously, pharmacy management for the institution (e.g. hospital 31) can prescribe a set of refill prescription rules which generally function to enhance outpatient pharmacy efficiency for refill prescriptions. According to default values established in the preferred embodiment of the present invention, the time period for refill validity is set to either start from last refill date or from the first prescription date. A rule may state a refill can be dispensed up to 7 days before and up to 14 days after the schedule refill date, and a prescription validity period may be set at 14 days for routine medications and two days for narcotics and controlled substances. Patient eligibility is checked (re-checked) during the refill process, along with the other drug restrictions.

Filling, Preparation, and Dispensing—Inpatient

As also shown in FIGS. 8, 9B, and 13-19, the "inpatient filling and dispensing" functional area provides functionality to perform: admissions, discharges and transfers (ADT) activities; provide a fill source; provide floor stock 141; provide for cart 143 fill and exchange; provide for filling and dispensing from the automated drug dispensing device 91; provide for manual filling; provide IV and TPN filling; provide chemotherapy filling; provide for pre-packaging; and provide for medication compounding.

According to the preferred embodiment of the present invention, inpatient medication orders are filled from floor stock 141, automated drug dispensing devices 91, or from medication fill carts 143. Carts 143 are filled in unit doses from the pharmacy on a 24-hour period basis and sent to the nursing units. Additional doses may be sent from the pharmacy for new patients or for new or changed order requirements throughout the day.

When a patient is admitted to an inpatient ward, two sets of cart/bin labels are required and can be printed on the label printer 77 in the assigned area of the pharmacy: one label for the cart/bin in the pharmacy and the other label for the cart/bin at the nursing unit. These labels 147 (see FIG. 8) are affixed to appropriate patient bin 149 of the fill cart 143 in the pharmacy and the patient bin 149 of the exchange cart 143 located in the nursing unit ward. Note, patient admission information will also be passed to the automated drug dispensing device 91 associated with the patient's receiving nursing unit. Note also, according to the preferred embodiment of the present invention, the medication administration program product 53 is integrated with the hospital information management software 51 to provide access to a patient ADT case records 151 (see FIG. 7A).

When a patient is discharged from the nursing unit ward, discharge tags (not shown) are printed in the assigned pharmacy. Medications in the cart 143 are withdrawn and appropriate billing adjustments are made. When a patient is allowed to leave the hospital temporarily on leave of absence, a notification will be sent to the pharmacy regarding the on-pass departure. All medications and labels 147 are then removed from the cart 143 by the pharmacist. When the patient returns from leave of absence departure, the orders can be reactivated (resume function) and medications are placed in the appropriate patient bin 149. When a patient is transferred from one nursing unit to another or when a patient is transferred from one bed to another in a nursing unit, appropriate labels 147 will be printed in the pharmacy. The pharmacist will affix the labels to the appropriate bin 149 in the new location cart 143 and will transfer medications to the new location cart 143.

Inpatient CPOE medication orders will normally be entered by the physician. Non-CPOE orders are normally entered in a patient's chart by the physician and faxed to the pharmacy by a nursing unit member. A nursing unit member can alternatively enter these orders as CPOE agent but these will require physician confirmation. Non-CPOE orders are normally entered by a pharmacist in the pharmacy using screens similar to those shown in FIGS. 10-12, but tailored to the pharmacist. A patient can be located by the pharmacist using a "find patient" search on the pharmacist's GUI (see FIG. 9B). The fill source will normally be identified as emanating from either floor stock 141, an automated drug dispensing device 91, or a cart 143 (see FIG. 8), although other sources, including pharmacy satellites or external sources, are within the scope of the present invention. The fill source will normally depend on whether the medication order is a scheduled order or a STAT/NOW order. For each nursing unit, some medications are maintained as floor stock 141. Most medications are preferably filled from floor stock 141 only for initial doses with follow-on scheduled doses being filled by the pharmacy through the cart fill process or by other means. Note, narcotics and controlled substances are maintained as floor stock 141 in all nursing unit wards, and psychotropic medications are sent via cart exchange from the pharmacy.

The cart fill process entails dispensing medication in patient-specific unit doses to inpatient nursing units on a 24-hour basis. The process will be triggered by initial pick and fill lists (see FIGS. 13-14) run via a scheduled job or on request. Scheduled inpatient medication orders for each nursing unit with fill source of 'CART' will be consolidated on the pick list by medication. The medication requirements for the next 24-hour period per floor can be listed with the total quantity. Correspondingly, the fill list report lists unit-doses needed for each patient for the next 24-hour period by the respective nursing unit. The report also lists PRN medications with PAR levels so that replenishment doses can be determined. The fill list can optionally include floor stock 141 and NCP medications which are not filled by the pharmacy. Further, running the report optionally generates labels for each unit dose, as desired. To account for new medication orders that occur after the pick list is run and before the cart 143 is sent to the nursing unit, catch-up fill lists (see FIG. 15) are run on a 'on request' basis. Catch-up fill lists can also be run mid-cycle to fill unit doses needed for new and changed medication orders. A stop-order list for orders which will end in the next 24-hours are also available in the system 30. This stop-order function will optionally produce alerts to physicians about the expiring orders, as described previously, and can optionally produce reminder labels to be sent to the nursing unit/physician.

Carts 143 are preferably normally exchanged with the nursing units every day in the afternoon. Before the carts 143 are exchanged, a final catch-up fill list can be run. This list will make necessary postings in the system 30 to close the current cycle (see FIGS. 16-18) and start the next cart filling cycle (see FIG. 19). This function can also produce a report listing all the locations and the date and time of each cart exchange. During the cart exchange, the filled carts 143 are sent to the nursing units and used carts 143 from each nursing unit are returned to the pharmacy. The returned exchange carts 143 are checked for any unused and returned medications. For all medications which are returned in the exchange cart 143, the pharmacist will ensure, using electronic medication administration record postings, that an appropriate nursing unit member has documented the reason for non-administered doses. The pharmacist can then either return the medication to stock or discard the medication. Electronic medication administration record posting will normally adjust inventory; however, if necessary inventory adjustments can be made by the pharmacist.

In the preferred embodiment of the present invention, the automated drug dispensing device 91 provides a readily available secure alternative storage unit preferably conveniently located in or adjacent each nursing unit ward. The maintenance of inventory levels, refills, loading, and removal of medications in automated drug dispensing devices 91 are described later in the inventory management functional section.

Manual filling procedures are used to fulfill medication requirements that arise outside the normal cart fill cycle. For example, medication orders received after the cart exchange process is completed may require initial medication doses to be sent to the nursing unit from the pharmacy, depending on the specified fill source for initial dose. Also, STAT or NOW/ASAP orders for medications not on the floor stock 141 or in the automated drug dispensing device 91 may require doses to be sent to the nursing units from the pharmacy.

IV and TPN filling have unique requirements. All IV types may require multiple ingredients. Each IV type is assigned a class, description, and a label. The type designations allow the IVs to be grouped by where and when they are filled. The IV fill process according to the preferred embodiment of the present invention starts by requesting an IV fill report. This report produces a work list and labels for each IV order. The IV fill report will optionally include orders at the following levels: nursing unit (individual or grouped); designation (TPN, Chemo or other); and frequency (continuous, intermittent, or syringe). The IV fill report can provide a batch control list by sorting IVs by primary active ingredient. This will facilitate filling of IVs with the same active ingredient at the same time, thus, reducing wastage of multi-dose vials. The IV labels include the expiration date and time and, if possible, lot number and associated information.

Total Parenteral Nutrition (TPN), as stated previously, is a special type of continuous IV. Multiple ingredients and medications may be included in the preparation of the TPN. TPN orders require special calculations to balance the dosage of all the active ingredients. As stated previously, TPN orders can be prepared in a worksheet fashion from multiple base ingredients. In the preferred embodiment of the present invention, the medication administration program product 53 includes instructions to perform the operation of linking standing lab orders to the TPN order for physician review. At the time of TPN order entry and preparation, the medication administration program product 53 can perform the following checks preferably using the external drug database: IV incompatibility check; and IV tubing and IV container incompatibility check.

Chemotherapy IVs are a typically intermittent IV that requires special handling because of their toxicity. Chemotherapy IVs are ordered by the physician using CPOE, however, according to the preferred process, filling the medication order 57 is not initiated by the pharmacist until after the patient undergoes blood tests (e.g. white blood count test) on the day of therapy, normally in the Oncology Treatment Center (OTC) ward of the hospital 31 and after a satisfactory review by a physician of the lab results (records 153), both of which are linked to the respective patient's electronic medication administration record 45, for review by the pharmacist. The chemotherapy preparation room pharmacist schedules the preparation of the IV based on the scheduled administration time of therapy according to the medication order 57. The pharmacist uses the order worksheet to balance the ingredient dosages (e.g. calculate amounts, diluents, etc.). Required labels are then printed on label printer 77 and affixed to both the IV bags/bottle and to the delivery bag. The IV preparation is then verified by a second pharmacist against the chemotherapy medication order 57 for ingredients, labels, expiration dates, and other parameters, and documented in the electronic medication administration record 45. Once verified by a second pharmacist, the IV preparation is sent to the OTC ward for administration.

In order to help streamline pharmacy operations, prepackaging and compounding of medications can be accomplished both in batch and on an ad hoc basis. Batch prepackaging is normally accomplished for stocked formulary items which are procured in bulk packaging. Such bulk packaged medications are re-packaged into smaller, dispensable packages in the pharmacy when low-stock conditions occur. Prepackaging requires generation of labels with expiry date and manufacturer lot number. The inventory management function of the medication administration program product 53, described later, provides the necessary functionality. Batch compounding also requires generation of labels with expiration date and lot number. Ad hoc prepackaging and compounding will occur for stocked and non-stocked medications is also supported by the inventory management function of the medication administration program product 53.

Filling Preparation and Dispensing—Outpatient

Outpatient fill process is triggered when a physician creates an outpatient medication order in the pharmacy system (CPOE) or when a pharmacist creates a medication order in the system 30 after a patient brings a paper prescription to the pharmacy (non-CPOE).

When a physician enters a medication order 57 in the system 30 via the CPOE order screen 120 (FIG. 12), several clinical and non-clinical checks are performed. As described previously, the physician may override the alerts generated by these checks with appropriate intervention codes. In case of stock-out situations, the medication administration program product 53 of the system 30 can notify the physician and provide a prompt to suggest a therapeutic substitution for the stock-out medication. After the physician completes entry of the medication order 57, a prescription claim card will be printed in the physician's office and given to the patient for picking up medications from the pharmacy. The CPOE entered medication order then appears on a pharmacy work queue for verification by pharmacist.

In some cases, a physician may issue a hand-written paper prescription to the patient. In such cases, the patient will present the prescription at the pharmacy window. The pharmacist will access the order screen 120 (FIG. 12) and enter the prescription as a medication order 57. Clinical and non-clinical checks will be performed at this time and the pharmacist may override the alerts generated by logging appropriate intervention codes. The current patient medical profile (see FIG. 10) is used in performing some of the clinical checks. In an outpatient setting, the most important clinical checks are the drug-drug interaction check and the drug-food interaction check, described previously. The most important non-clinical checks include the eligibility check, stock availability check, medication restrictions check (physician, specialty or patient), and a refill availability check for each medication on the medication order 57.

The outpatient fill process is different than that of the inpatient fill process, described above. The outpatient fill process generally starts when a medication order 57 is verified and confirmed by the pharmacist. This will cause the following labels/forms to be printed which include: a bilingual fill label with patient, medication, and dosage information; a patient monographs in the patient's native language; a refill claim card, if required; and a medication order ($R_x$) summary sheet or card, if required.

According to the preferred embodiment of the present invention, the fill label is used by filling pharmacist to fill the medication from floor stock and is affixed to a medication container. The medication container or containers are then consolidated in a medication bin. The contents of the medication bin are verified by another pharmacist before the medication bin is passed to the dispensing window. The window pharmacist will check the contents of medication bin against the medication order 57, print a medication order ($R_x$) summary card and a refill claim card, if required, and dispense the medications to the outpatient.

To enhance efficiency of the outpatient filling and dispensing process, the medication administration program product 53 provides various work queues that can be accessed from clinical work station. The following is a sample list of queues: a CPOE order queue; a pharmacist verification work queue; a pharmacist fill queue; and a separate compound medication order queue for filling compound medication orders. Also, to further enhance efficiency, CPOE allows advance-filling (pre-filling) the CPOE medication orders 57. After a physician enters a medication order 57, depending on the medication, location and time of day, the pharmacist can review the medication order 57 before a patient presents the claim card C at the pharmacy window. After verifying the medication order 57, the pharmacist may start the fill process by printing appropriate labels and forms. Advantageously, this advance-filling process can reduce the waiting time for patients at the pharmacy. Advance filling may be carried out at pharmacy's option, however, the medication administration program product 53 can incorporate rules that restrict advance filling to certain medication orders 57. Still further, to enhance efficiency, the medication administration program product 53 can receive refill requests from outpatients via the communications network 41. The medication administration program product 53 can also incorporate rules providing refill request restrictions based on medication, location, and/or time.

Advantageously, in order to assess pharmacy productivity, the medication administration program product 53 can include instructions to perform the operations of capturing filling-process data including key fill-related times: date/time medication order was entered; date/time the patient shows up at the pharmacy window for medication pick-up; date/time the medication order was verified and fill labels were printed by pharmacist; date/time the medication in the medication bin is verified; and the date/time medications are dispensed to the patient, evidenced by printing the medication order ($R_x$) summary card.

Medication Administration

Medication Administration is implemented using electronic medication administration record (EMAR) functionality, which is tightly integrated with inventory management. Electronic medication administration record functionality advantageously provides enhanced point-of-care administration and documentation. The electronic recording of administration can be implemented either directly or, if the medication administration program product 53 is positioned as an add-on to hospital information management software 51, through or using the hospital information management software 51 care documentation (Care Docs).

According to the preferred embodiment of the present invention, as described previously, the electronic medication administration record functionality provides nursing unit members, and to some extent, outpatient clinics, the ability to: view scheduled and verified medication orders for nursing sign-off and acceptance; record administration of verified and signed-off orders; change scheduled administration time of PRN 'as needed' orders; change a scheduled administration time of non-PRN order for clinical reasons with intervention logging; record appropriate interventions and notes during recording of medication administration; and record unscheduled administration of medications for STAT or NOW/ASAP received as telephone and verbal orders (TO/VO). Also provided are alerts to nursing units for new and changed medication orders, described previously.

When one or more automated drug dispensing device 91 is used in the nursing unit, the electronic medication administration record functionality provides the ability to: post medication removals events to the respective patient electronic medication administration record 45; post medication administrations to the respective patient electronic medication administration record 45 for the associated medication removals; and ability to update the automated drug dispensing device with data provided in the electronic medication administration record 45.

The electronic medication administration record functionality also supports emergency medical services (EMS), rapid episodic care to unanticipated acute conditions with short patient interactions. This functionality includes the ability to: post to electronic medication administration records 45, administration of medications for medication orders that have not been previously created in the system 30. This includes verbal orders from physicians that are subsequently approved. Medications can be administered from EMS floor stock 141. When the administration is posted at one of the hospital nursing unit computers 81, the medication administration program product 53 of system 30 automatically creates the medication order 57 with optional physician confirmation within a specified time (configurable by organizational unit). Such medication orders can be placed and/or displayed in a special queue for pharmacist review. Further, when the medication order 57 is automatically created, displayed is a menu or text entry field provided to record appropriate interventions and notes. Correspondingly, when the emergency medication is removed from one of the automated drug dispensing devices 91, a medication administration (record) is automatically posted to the respective patient's electronic medication administration record 45.

The electronic medication administration record functionality also supports immunization administrations. Similar to EMS postings, immunization administrations can be posted for orders that have not been created in the system 30. When an immunization is posted in the electronic medication administration record 45, the medication administration program product 53 of system 30 automatically creates the medication order 57 with optional physician confirmation within a specified time (configurable by organizational unit), and places and/or displays the medication in a special queue for pharmacist review. Further, if the hospital information management software 51 incorporates Immunization Care Docs, the immunization medication administration can also be posted substantially simultaneously to such related Immunization Care Doc.

The electronic medication administration record functionality includes display functionality to enhance medication administrations. For example, according to the preferred embodiment of the present invention, the medication administration program product 53 is integrated with the hospital information management software 51 to provide access to patient significant data sheets (SDS) 155 (FIG. 7A), case information 151, and patient location from the patient master data 46 and patient medication profile 43. The electronic medication administration record display functionality provides an electronic medication administration record display screen 86 (FIG. 5) to display scheduled medication administrations for signed-off of orders for a specified default time window which can be changed to show recent and past medication administrations. For each scheduled administration, the medication order details consisting of medication name, dose, strength, frequency and scheduled administration times can be displayed. For each IV order, the type of IV, infusion rate, interval, bag number and a list of ingredients can be displayed. PRN orders have a frequency of administration but do not have set administration times, and thus, are administered on an as needed basis. The electronic medication administration record display screen 86 shows administration times calculated using the prescribed frequency and using an adjustable default administration schedule. The electronic medication administration record display screen 86 also preferably includes a configurable auto-refresh function. The nursing unit members NM can set an auto-refresh time, for example every 15 minutes, in order to view preferably highlighted changes (e.g. new or change orders) and allow screen movement automatically along the medication administration timeline.

The electronic medication administration record functionality also includes functionality to allow ad hoc printing of a "medications due list" report. The report lists scheduled medication administrations and includes options to list all patients in a specific nursing unit, patients assigned to specific nurses, a single or a group of patients, and an administration window. The report can show all scheduled orders: verified and signed-off orders, non-verified but signed-off orders, and non-verified and non-signed-off orders. The report can identify the medication order type (scheduled, STAT, NOW/ASAP or PRN), and indicate administration times for the window selected along with medication information. A "historical medications due list" report can also be printed. The report lists medication administration history for a specified time window, with options similar to that of the medications due list report.

In the preferred embodiment of the present invention, the electronic medication administration record functionality includes various posting rules. For example, all new and changed medication orders can be displayed on the electronic medication administration record display screen 86 and can be placed under two groups: verified and non-verified. Order verification is accomplished by the pharmacist. A nursing unit member NM can sign-off pharmacy verified orders. In addition, non-verified STAT or NOW/ASAP orders can be signed off by nursing unit members NM for immediate administration. These orders can be placed in a special pharmacy queue for review. Note, the electronic medication administration record posting rules are preferably set so that postings can only be accomplished on orders which are signed-off by a nursing unit member NM.

For scheduled and verified orders, medications administered from floor stock 141 or cart 143, a nursing unit member NM can post the administration information on the electronic medication administration record display screen 86. For IVs, nurse can record details of fluid volumes and infusion times. This may require several entries over a period of time. Nursing unit members NM can post interventions and notes in case of exceptions or if additional information is required in response to physician instructions.

STAT or NOW/ASAP medication orders sent to the pharmacy via telephone or fax can be created in the system 30 as non-CPOE orders in the pharmacy and medications can be rushed to the nursing unit on an expedited basis. These orders can then appear as scheduled orders on electronic medication administration record display screen 86 and can be signed-off by nursing unit members NM usually before administration and electronic medication administration record posting.

If the medications are instead administered from an automated drug dispensing device 91, electronic medication administration record display screen posting are not required. When the medications are removed from automated drug dispensing device 91, the time of removal and other administration data is automatically posted on the electronic medication administration record 45. Nursing unit members NM can later post the actual administration time on the electronic medication administration record 45. This updated information is then reflected in the automated drug dispensing device 91.

A medication order can be scheduled and non-verified. This situation may occur when a physician enters a STAT or NOW/ASAP medication order 57 using CPOE and the medication order 57 is not yet verified by the pharmacist, and the medication is available for administration from either floor stock 141 or an automated drug dispensing device 91. The medication order 57 can appear on the electronic medication administration record display screen 86 as scheduled even though the pharmacist has not verified the medication order 57. A nursing unit members NM can post the administration information if the medication is sourced from floor stock 141. Administration information is posted automatically if sourced from an automated drug dispensing device 91.

A medication order can be unscheduled and non-verified. This situation can occur in an emergency medical situation, and in outpatient clinics, operating rooms, PACU, outpatient treatment rooms, immunization clinics, and in inpatient nursing units when a STAT/ASAP medication order is administered from floor stock 141 or from an automated drug dispensing device 91. Such a medication order is not available in the system 30 to record administrations. As a result, the order does not appear on the electronic medication administration record display screen 86.

If the medication is administered from floor stock 141, a nursing unit members NM can use special electronic medication administration record display screen functionality to post administration information. Posting of administration information automatically creates the medication order 57 in the system 30 with optional physician confirmation within a specified configurable time. The medication order 57 is then displayed in a special queue for pharmacist review. As with normal computerized physician order entry, nursing unit members NM can have access to drug information monographs and prioritized warnings on medications. Nursing unit members NM can also have the option to perform clinical interaction checking against the patient medication profile 43 prior to administration of STAT or ASAP/NOW verbal or telephone orders.

If the medication is administered from an automated drug dispensing device 91, the nursing unit members NM can use an override function to remove the medication from the automated drug dispensing device 91 by entering patient identification data (e.g. medical record number). The automated drug dispensing device 91 sends the necessary information to the medication administration program product 53 to automatically create a medication order 57 and automatically post the time-of-removal and other administration information on the electronic medication administration record 45. Nursing unit members NM can then post the actual administration time on the electronic medication administration record 45 and this updated information will be reflected in the automated drug-dispensing device 91.

For scheduled medication orders 57, nursing unit members NM can be provided appropriate permissions to be allowed to change the scheduled administration times to meet clinical needs. Nursing unit members NM can change the administration time to a future value or mark the administration of the dose as "skipped." Intervention logging and notes, as described previously, are normally required.

A medication order can be listed as PRN. With PRN medication orders, nursing unit members NM can be provided appropriate permissions to change the proposed administration times for clinical needs. Similar to that of scheduled orders, nursing unit members NM can change the administration time to a future value or mark the administration of the dose as "skipped." The other posting rules are preferably the same as for scheduled orders.

Whenever new orders are created or existing orders are modified, it is important that the nursing unit members NM are alerted to the changes. According to the preferred embodiment of the present invention, the following options will be available to alert the nursing unit: For CPOE and non-CPOE non-agent orders, a listing of new and changed orders will be printed in the nursing unit on a nursing unit printer 87 as and when a physician or agent completes the medication order entry. The information provided to the affected nursing unit includes medications and other non-medication orders and instructions. The listing alerts the nursing unit to changes in the medication order, if any. All new and changed medication orders (CPOE and non-CPOE) are displayed on the electronic medication administration record display screen 86 and new orders and changes can be highlighted to provide the nursing unit members NM clear recognition of the changes. A nursing unit member NM is assigned to review to the electronic medication administration record display screen 86, frequently. The electronic medication administration record display screen 86 can be auto-refreshed based on optional settings to continuously identify required administrations as they become due. Note, a charge nurse is normally assigned the task of monitoring the organizational unit-level electronic medication administration record display screen 86 for new and changed orders.

The electronic medication administration record functionality also includes provisions for wasted doses and returned doses. A dose can be wasted for various reasons. For example, a dose can be spilled, thrown up by the patient during administration, or discarded for other reasons (but not returned to stock). The dose can be for a scheduled order, PRN, or from an unscheduled order (STAT/ASAP). The fill source could be from floor stock 141, a cart 143, or from an automated drug dispensing device 91. The nursing unit members NM will record the non-administration of the dose on the electronic medication administration record 45 with preferably notes and a reason code, and the quantity administered should be recorded as "zero." The medication dose will deplete inventory when the fill source is from floor stock 141 or a cart 143 but will not be charged to the patient (default). If a wasted dose requires re-administration, a nursing unit member NM will order an additional dose either from pharmacy to be added to the next exchange cart 143, acquire it from floor stock 141, or acquire it from an automated drug-dispensing device 91. The additional medication dose will deplete inventory and will be charged to the patient, automatically.

Regarding returned doses, scheduled non-PRN doses which are not administered may be returned to stock. The patient will not be charged for returned doses and the medication administration program product 53 includes functionality to reverse charges for the returned medication. For cart returns, the pharmacist will utilize a "materials management returns and adjustments" functionality of the hospital information management software 51 to adjust inventory to reflect restocking or discard. For returns from doses dispensed from an automated drug dispensing device 91, a nursing unit members NM can utilize the automated drug dispensing device 91 "credit" or "waste" functionality to adjust inventory to reflect restocking or discard.

Inventory Management

The inventory management function provides functionality to the extent that, according to the preferred embodiment of the present invention, any material that is used by the pharmacy, be it drugs or supplementary materials, such as, for example, intravenous bags, tubing or, containers, will be maintained as a unique number in the hospital information management software 51. Furthermore, material locations and inventory balances in Material Management-managed locations throughout the hospital 31 can be represented on-line and in real-time. The inventory management functionality can initiate replenishment from external suppliers, and manage the subsequent internal distribution of material to the point of use within the hospital facilities. Orders placed for drugs, for both inpatients and outpatients, will trigger inventory management transactions which will issue materials from stock, consequently depleting inventory, hence automatically triggering replenishment requirements once more. In addition to the more traditional inventory management functions, such as receiving and issuing materials, tracking inventory levels, and transferring materials from location to location; the inventory management functionality also can address the more unconventional business processes unique to a pharmacy. These include managing narcotics and control drugs, compounding substances, re-packing bulk items into smaller doses, and chemo and intravenous drug preparations.

Finally, apart from integrating with the overall hospital information management software solutions, the inventory management solution for pharmacy management operations integrates seamlessly with other elements of the total pharmacy solution. These include the Drug Master file (drug formulary 47), the use of automated drug dispensing devices 91, and the electronic medication administration record 45 as a tool for recording the drugs administered to patients.

According to the preferred embodiment of the present invention, every material used by the pharmacy is assigned a unique number used to access material data from a material master 93 which carries such data as: description; unit of measure; whether or not the material is batch-managed; min/max stock levels per location; general storage information; bin number per location; shelf-life expiration; temperature conditions; and material price. The materials are separated into two distinct types with different number ranges and data fields. Pharmaceuticals utilize an externally dictated number range selected to match the drug formulary 47 and external drug databases, and carry additional data such as: mnemonic; therapeutic class; classification code (ATC-code); ingredients; and substitute material. Operating supplies are assigned an internal number range.

With respect to external replenishment, when inventory levels drop below predefined reorder points, consumption-based planning functionality in the hospital information management software 51 will automatically trigger a replenishment requirement. Note, if purchasing functions are located in a separate module of the hospital information management software 51, or in a completely external software package, an interface communication link is provided to bridge the gap between the differing modules or packages, to prevent the need for double data entry.

Internal replenishment is the replenishment of distributed stock (for example floor stock 141) from a central pharmacy storage location after floor stock levels have been depleted. Functionality developed within the medication administration program product 53 or through interface with the hospital information management software 51, establishes various internal replenishment triggers. For example, consumption-based planning functionality inherent in the hospital information management software 51 can automatically generate requirements based on material depletion from floor stock 141, with respect to pharmaceutical material, only. Further, operating supplies (e.g. bandages) will be re-stocked on the ward from central storage locations using standard manually created material requisitions. These requisitions can be implemented to trigger an issue of a daily supply, for example, from a central location. Once issued to floor stock 141, this material is preferably not tracked, but used as and when required. The advantages of using such a requisition procedure is that a user does not need to perform a system transaction every time such a material is used.

For materials issued from the automated drug-dispensing device 91, the device 91 will communicate with either the medication administration program product 53 or hospital information management software 51 to align inventory levels. The automated drug-dispensing device 91 can manage its own stock levels and reordering.

For medications requiring ingredients, such as, for example, compounds, the user can enter the ingredients and the product in the correct units of measure, incorporating such information as material cost, batch characteristics, and shelf-life data. When formulation of the medication is complete, saving the medication results in the ingredients being depleted from stock and the newly formed medication being added to stock. This inventory transaction allows the user to indicate how much of the ingredients and product are to be issued there and then (and to whom), and how much is to be put back into storage. For example, an order may be placed for a compounded item, but the user makes a much larger quantity than is required for the order, so there is no wish to issue all of the ingredients to the patient, but only a percentage. Advantageously, the transaction allows consumption postings at the time of compounding, to be selected either to the case (or multiple cases), or the user department cost center. The formulated compound "inherits" the batch information from the ingredients, including material cost.

The inventory management functionality provides for different types of physical inventory methods including: continuous inventory during stock placement; continuous inventory on zero stock check; annual inventory (also called periodic inventory); inventory sampling; manual counting; and cycle counting. The preferred embodiment of the present invention implements cycle counting. Cycle counting provides automatic creation of the physical inventory documents. Cycle counting negates the need to count every item and allows a breakdown of items by stratification. Cycle counting applies a prioritization whereby fast moving high value items are counted before slow moving, inexpensive items. The hospital information management software 51 can track which items have been counted and when, and alert inventory managers of which items are due for counting.

The inventory management functionality also provides a source storage location table that, depending on the material and requesting storage location, will assign a source location to a requesting location for internal replenishment. A reservation user exit routine reads the table and updates the source storage location in the transfer reservation and updates the source storage location in the issue reservation for non-managed storage locations.

Costing

Material costing is an integral component of the pharmacy management. Costing of materials incorporates the following application areas: purchasing; inventory management; and logistics invoice verification. Material Costing determines or records the stock value of a material. The stock value is calculated using the formula:

Stock value=stock quantity×material price.

Thus, if the stock quantity or the material price changes, the stock value changes. According to the preferred embodiment of the present invention, every material in inventory carries a cost. Advantageously, providing such functionality allows for diverse inventory valuation methodologies, known to those skilled in the art. Further, such functionality allows cost center managers to track the value of materials issued to operational units, patient cases, and even materials issued due to wastage.

Reporting

Reporting functionality includes operational reporting requirements and analytical reporting. According to the preferred embodiment of the present invention, there are four general types of reports: processing and operational reports which are static report designs (canned) required for day-to-day use; listings which are file listings for master data tables and other listings; analytical queries which are specific queries against the database; and ad hoc reports.

Process reports can be scheduled or requested and are configurable according to typical report parameters. Most process reports, described below, have the option of being run for a single or multiple organizational units. Groups of organizational units are maintained so that only the group need be selected, not each of the operational units in the group.

Advantageously, computerized physician order entry allows for enhanced process reporting. Several of the more important reports according to the preferred embodiment of the present invention are described as follows: A Pick List report, run on a daily basis, prints a consolidated list of medications, ingredients and required quantities that are needed for patients in a specific organizational units (i.e. what has to go on the cart 143 for the organizational unit). A Medication Fill report, run on a daily basis, is part of the cart exchange cycle and is used to report what medications should be on the cart 143. A Catch-Up Fill (Update Fill) report is a version of the Medication Fill report which lists only what has changed since the original fill run. It indicates which medications have to come off the cart 143 and what new items have to go on the cart 143. An IV Fill report prints labels for all IV's which must be prepared in the current cycle. The report is a control report and should be able to be run by IV type to balance workload by type. A Close report is a report that "closes" each location (organizational unit) it is run for. Closing a location sets it so that the next Fill Report will be an initial run for the next day. A Stop Order report (and accompanying labels) lists inpatient orders that are about to stop (discontinue) in the next 24 hours. This report may be discontinued and the information displayed via special work queues for physician action and nursing and pharmacy review. A Food Drug Interaction report, run daily for inpatients only, lists foods which may interact or interfere with patient medications, and is forwarded to the Dietary unit of hospital 31 to assist the dietician in preparing patient menus. A Conflict Intervention Log report, printed daily, lists all conflicts and interventions recorded from the previous day. A Conflict Intervention report (batch), lists summary information by clinic and system-wide totals: daily, monthly and yearly. A Conflict Intervention report (requested) is requested for a user specified period of time, for one or more clinics, and all or some of the conflicts and interventions, and reports details of conflicts and interventions and is preferably summarized by reason code. A Workload report, run in batch, lists summary statistical information for functions performed, conflict encountered and interventions: daily, monthly, and yearly. A Narcotic Quarterly report lists the usage of inpatient and outpatient psychotropic and narcotic medications.

File Listings are reports that aid users in maintaining the system 30. Hard copy listings provide an easy way to look up table values for new users or for seldom used tables (cheat sheets). According to the preferred embodiment of the present invention, each user maintainable table (e.g. formulary, reason codes, frequency, etc.) has a formatted listing which can be viewed or printed. File listings have optional sorts where tables have more than one key or other sortable field. Inclusion of soft deleted items is also an option. A patient's medication profile is a form of listing which can print all orders in a consolidated report with a number of inclusion and sort options. The inclusion options can include printing: active orders only, specific order types, or period of time. The sort options can include: order number (ascending/descending), order type, date (ascending/descending), and medication with multiple ingredient orders such as compounds and IVs displaying each ingredient, optionally.

Ad hoc reports include analytical queries. According to the preferred embodiment of the present invention, analytical queries are set up as report templates using standard hospital information management software utilities. These reports allow the user to identify selection criteria and some output options. Specific studies (template combined with specific criteria) can be saved for re-running. Specific studies can also be scheduled for recurring runs (e.g. weekly, monthly, etc.). Templates are preferably provided for: medications "due/duration" by prescribing physician, by drug class, and by formulary item(s); trigger drugs analysis; and drug abuser activity. When the medication administration program product 53 is implemented as an add-on to MySAP Healthcare hospital information management software, the ad hoc reports can be fulfilled using "Crystal" (third party) reports which provide real-time reporting, and SAP's Business Data Warehouse which provides for most near-real-time, analytical, decision support, historicals and ad hoc reporting.

Label Printing

Labels are an integral part of improving pharmaceutical services and in achieving the objective of delivering the right medication to the right patient in the right dose at the right time. As previously described, labels are generated during various on-line functions like medication order entry, medication order verification, ADT, and by batch processes like pick list and fill list printing. Labels are used to provide administration instructions to patients and nursing unit members. Filling and dispensing processes also rely heavily on labels.

According to the preferred embodiment of the present invention, label templates will be created for the following order types and special requirements: routine medication (inpatient); routine prescription (outpatient); sliding scale dose; compound; oral syringe; IVs (continuous, intermittent, injectable, and TPN); bin labels; and inventory items (for pre-packing and compounding). The label content is maintained by the end users using standard texts and process variables. Order and inventory related data is available as process variables for inclusion in standard texts. At runtime, the labels are generated based on the label template and associated standard texts with variable substitution. Advantageously, materials management data including expiry date, and batch identifiers, is accessible to the medication administration program product 53, and batch control is implemented with materials management to ensure the data is meaningful.

For inpatient medications, the labels are preferably in English and may include technical abbreviations and codes which are meaningful to health care professionals. The abbreviations and codes allow for more information to be printed on a label of limited size. For scheduled medications, two copies will usually be printed, one for each of the two exchange carts. For single dose medications, such as STAT orders, only one label is needed. These labels are set to print at the time an order is verified. An auxiliary label can be requested to print as well. Auxiliary labels contain additional instructions and can include standard texts or free-form instructions.

For syringes (oral and injectable), which may have more than one ingredient, a multi-ingredient format can be used with the active ingredients shown first. Labels for injectables are affixed to each syringe. At the time an order is verified a label should print for each "now" dose (doses to be filled and sent to the floor). When the pick list or fill report is run a label should print for each syringe to be filled during the current cycle.

For IVs, IV labels list each ingredient, the units per dose in the strength measure of the ingredient, the volume of each ingredient, and the total volume. Depending on the type of IV, the label also includes the rate of infusion (including the rate unit), interval of administration, and bottle sequence number.

An IV label is produced for each IV dispensed. In some cases, two labels may be required for each dose (e.g., chemotherapy IVs require a label on the outer bag as well as the IV itself). Labels for scheduled administrations are set to be produced by the IV Fill report.

Outpatient labels provide medication administration instructions for ambulatory patients. The labels provide specific instructions at a non-technical level, and are preferably printed in both English and in the native language of the patient. Outpatient labels are set to be printed after an order is verified. The label is used as part of the outpatient fill process.

Freeform labels are provided to support special situations where standard labels do not meet the user requirements. Instead of using standard label templates and standard texts, free-form text created by the users can be used for the content of the label. The free-form texts can advantageously be saved for future use.

Labels (inventory tags) need to be produced when batch prepackaging, repackaging, and compounding are performed. These labels identify the manufactured or repacked items that are then stocked as inventory items. Drug mnemonic, description, strength, batch identifier, and expiry date are printed on these labels.

Labels are routed using a print location concept. Print locations are preferably associated with computer location and label. Print routing records provide instructions to direct labels to a printer. This routing system provides special handling for bin (tag) labels produced in the background by Admissions Discharge and Transfer (ADT) functions, and for labels produced in batch by reports such as the Pick List and Fill List.

Advantageously, the medication administration program product 53 provides the ability to re-print labels from orders and other on-line transactions. For batch processes which generate labels, like Pick List and Fill List, probations are also available for reprinting labels from the batch jobs.

Organizational Change Management

According to the preferred embodiment of the present invention, enhanced pharmaceutical order entry and administration by medical personnel and enhanced pharmaceutical inventory control within a medical institution is obtained through implementation of the medication administration program product 53 and corresponding organizational changes designed to maximize the benefits of such implementation. The change management strategy focuses on communication and should include: identifying and communicating implementation issues to change managers and affected pharmacy personnel; development and implementation of solutions; tracking and reporting of progress; escalating unresolved issues according to clearly-defined procedures; and maximizing use of organizational websites and other available communications media to communicate to, and inform/educate users.

According to the preferred embodiment of the present invention, existing data is converted/formatted, as necessary, and policies and procedures are revised for issues commensurate with the implementation. FIG. 25 illustrates typical change management focus areas and their associated functional area categories. Solutions are primarily education and training of the affected personnel, especially clinicians and nursing unit members, in the process changes.

End-User Education and Training

According to the preferred embodiment of the present invention, a pharmacy training team is established to implement and streamline the end-user training process. The training team focus includes: the design, development, and implementation of role-based training courses; the conducting of end-user training; extraction of continuous feedback (ad hoc and through evaluation of end-user learning); delivery of on-line user documentation and help systems; and implementation of computer-based supplemental training. The role-based and process driven training methodology has been found to be the preferred methodology. Exercises and training scenarios, preferably implemented just-in-time, are used to replicate everyday scenarios that pharmacy end-users will need to carry out.

Various designed courses include: Pharmacy Orders for Inpatient Clinicians and Nursing Unit Members; Pharmacy Orders for Outpatient Clinicians and Nursing Unit Members; Pharmacy Orders for Pharmacists; Chemo and IV Room Pharmacist; Computer Support Pharmacist; Pharmacy Reporting; Drug Information Pharmacist; Compounding a User Unit Pharmacist; and Inventory Management and Costing. Additional courses include: Process Flow Diagrams; Responsibility Matrix Forms; and Business Documentation Deliverables.

The Pharmacy Orders for Inpatient Clinicians and Nursing Unit Members course, primarily directed to inpatient physicians, nurses, and support staff, covers transactions needed to create and view orders for inpatient drug prescriptions, immunization related functionality, and electronic medication administration record functionality. The Pharmacy Orders for Outpatient Clinicians and Nursing Unit Members course, primarily directed to outpatient physicians, nurses, and support staff, covers transactions needed to create and view orders for outpatient drug prescriptions and immunization related functionality.

The Pharmacy Orders for Pharmacists course, primarily directed to pharmacists and pharmacy technicians, covers creation and viewing of pharmacy orders for pharmacists; management of work lists, queues and orders; immunization related functionality; filling and dispensing (outpatient and inpatient); and reporting. The Chemo and IV Room Pharmacist course, primarily directed to the Chemo and IV pharmacists, covers the transactions required by the Chemo and IV room pharmacist to create orders, use order worksheets, and dispense IV and Chemo medications. The Computer Support Pharmacist course, primarily directed to CSLs and Computer Support Pharmacists, covers CSL related duties required to be performed by the computer support pharmacist. The course also covers label administration and external database administration. The Pharmacy Reporting course, primarily directed to physicians, nurses, pharmacists, and support staff, covers reporting functionality required to maintain and forecast supply and demand.

The Drug Information Pharmacist course, primarily directed to drug information pharmacists, covers transactions used by the drug information pharmacists to: add/delete medications to/from the formulary; use order sets and IV templates; identify medication and patient restrictions; update of patient allergy files; investigate information about drugs; and use of clinical and non clinical checking. The Compounding and User Unit Pharmacist course, primarily directed to compounding and user unit pharmacists, covers the transactions required by the compounding and user unit pharmacist to mix substances for a certain medication as well as to provide those medications stocked at the different medical institution units.

The Inventory Management and Costing course, primarily directed to supply pharmacists, covers transactions that a supply pharmacist utilizes to create requisitions, view MRP, track floor stock, and handle replenishment and all other external procurement related activities.

As perhaps best shown in FIGS. 20-24, embodiments of the present invention include methods to enhance provision of pharmacy services to medical personnel within a medical institution including enhanced pharmaceutical medication order entry and administration and pharmaceutical inventory control. For example, as perhaps best shown in FIG. 20, in an embodiment of the present invention, a method to enhance pharmaceutical order entry by medical personnel within a medical institution includes displaying on a physician video display device 69 a graphical user interface including a medication order template or form 55 (block 201) having database entry fields to allow an electronic medication order 57 entry by a physician, and populating the medication order template or form 35 with default values or applying a medication order ingredient template (block 203). The default values can be for medication route, dose, frequency, duration, or any other medication attribute. The medication order template or form 55 can also include tools to provide access to dosing recommendations including minimum and maximum dose, lifetime cumulative dosing, pediatric dosing, neonatal dosing, and geriatric dosing. The medication order template or form can include tools to provide access to standard medication order sets, IV templates, and chemotherapy templates.

The medication order template or form 55 also includes provisions for performing clinical and non-clinical checks (block 205). Clinical checking is performed to verify the medication order does not exceed various normal parameters, such as, for example, a normally prescribed dose range, interact negatively with other currently prescribed medications, or duplicate another currently active medication order. Non-clinical checking of the medication order is performed to verify the medication order does not violate various preselected medical institution requirements. For example, a user can verify that the medication order does not duplicate medication against a current medication profile at an ingredient level or at a therapeutic level. Verification can be made that the patient is eligible to receive items listed in the medication order, the physician is authorized to prescribe items listed in the medication order to the specific patient, and that the medication order does not include items having a quantity or duration exceeding preselected institutional limits. If a medication order parameter entered in the template or form 55 violates a preselected rule (block 207), a respected clinical or non-clinical alert is displayed (block 209).

The graphical user interface can display an entry field providing the physician an ability to override the clinical or non-clinical alert (block 211). If the alert is overridden, intervention logging is automatically performed (block 213) to document the occurrence and to provide the physician the ability to document the reason. An electronic medication administration record 45 is then created or updated (block 215).

Figure 21:
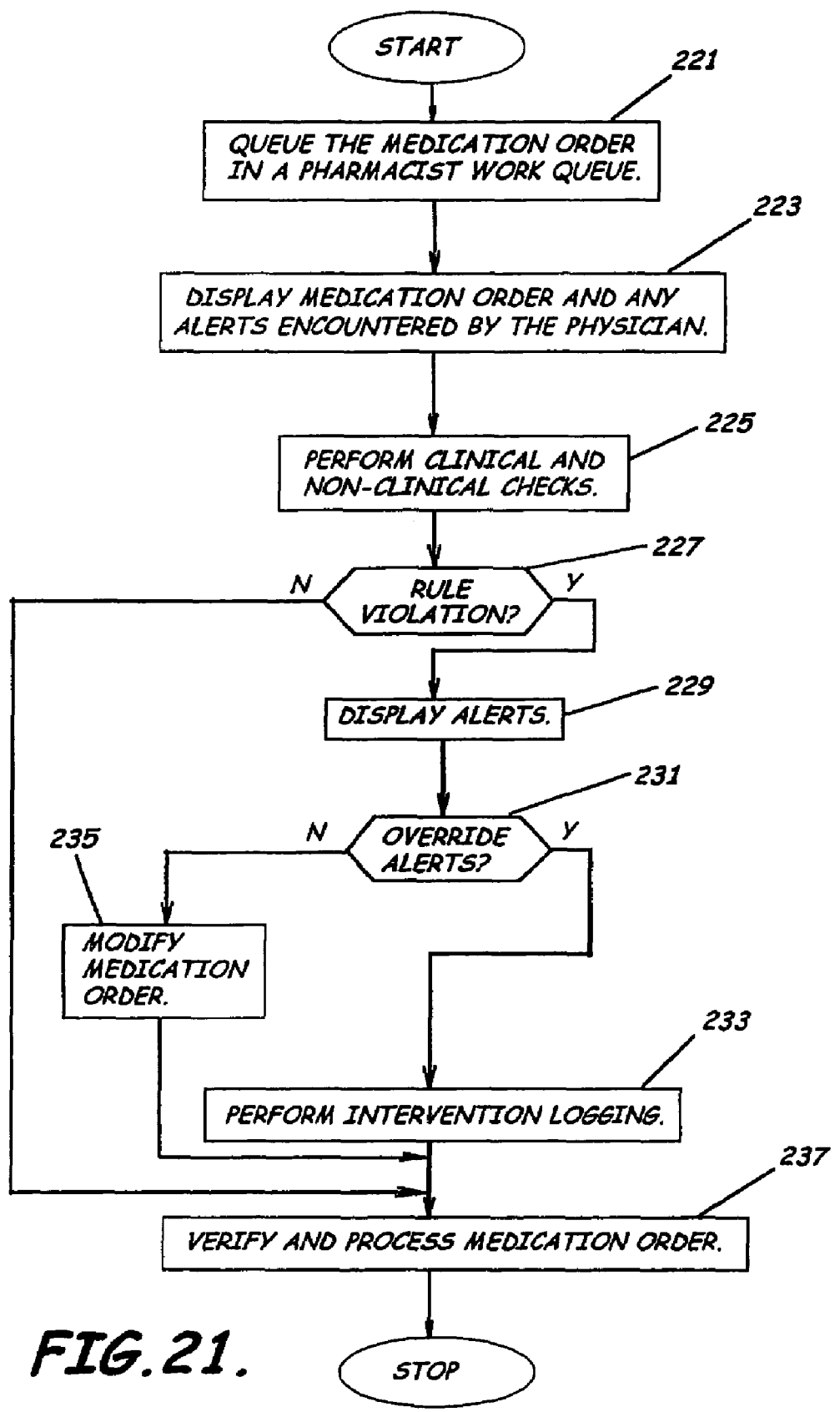
FIG. 21 is a schematic flow diagram of a method to enhance pharmaceutical order entry by medical personnel within a medical institution according to an embodiment of the present invention.

Also for example, as perhaps best shown in FIG. 21, in an embodiment of the present invention, a method to enhance pharmaceutical order entry by medical personnel within a medical institution includes queuing in a pharmacist working queue the electronic medication order 57 entered by the authorized physician (block 221). The medication order 57 entered by the physician and any clinical and non-clinical alerts encountered by the physician along with overriding reasons, posted by the physician, are displayed on a pharmacy clinical workstation video display device 72 (block 223). The pharmacist can perform clinical and non-clinical checks (block 225). If a rule violation is determined (block 227), alerts are displayed (block 229). As with the physician's review, the pharmacist can override the clinical or non-clinical alerts encountered during medication order review and verification (block 231) if provided appropriate permissions, and can input in an entry field, an override reason. If the alert is overridden, intervention logging is automatically performed (block 233) to document the occurrence and to provide the pharmacist the ability to document the reason. Alternatively, the pharmacist can modify the electronic medication order 57 (block 235) or substitute a drug item upon consultation with the prescribing physician. The pharmacist then continues the review and verification process to thereby process the electronic medication order 57 (block 237).

Figure 22:
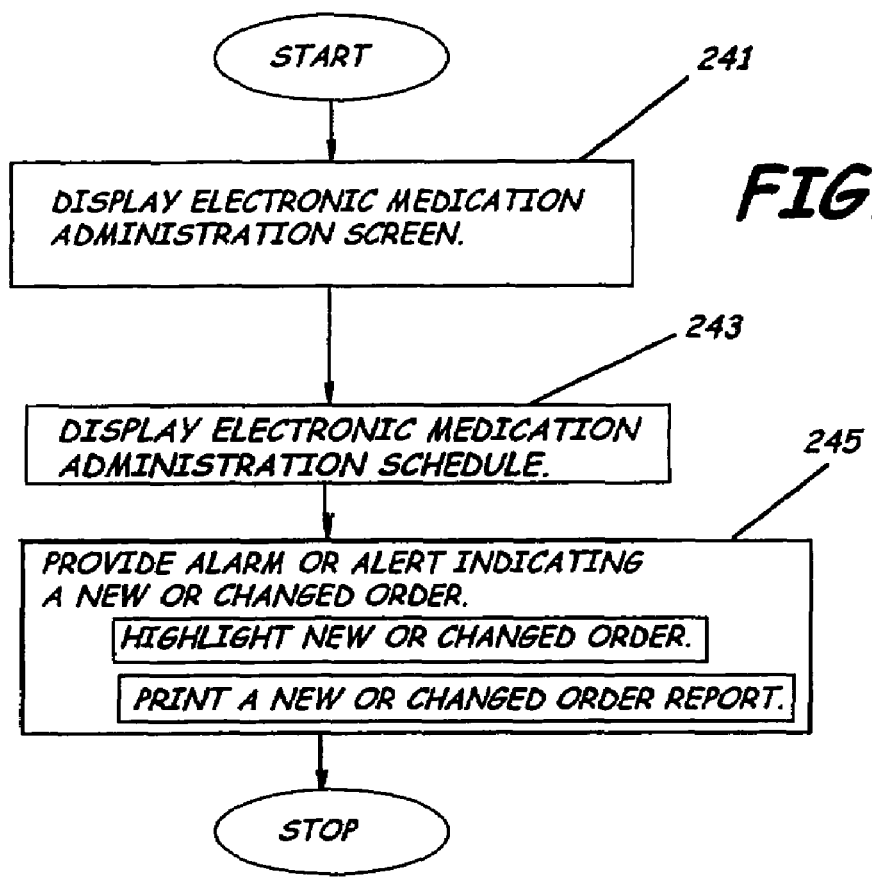
FIG. 22 is a schematic flow diagram of a method to enhance pharmaceutical administration by medical personnel within a medical institution according to an embodiment of the present invention.

In an embodiment of the present invention, as perhaps best shown in FIG. 22, a method to enhance pharmaceutical administration by medical personnel within a medical institution includes displaying on a video display device 89 (block 241), positioned at a nursing unit located remote from the pharmacy, a graphical user interface including a nursing unit-level electronic medication administration screen 86 having electronic medication administration record 45 data forming a medication administration schedule. Advantageously, the electronic medication administration schedule is provided (block 243) to help nursing unit members visualize their work requirements and to allow medication administration entry by an authorized nursing unit member. In the preferred configuration, the screen 86 is auto-refreshed at a preselected time interval to allow automated screen shifting along the nursing unit's medication administration work timeline. The refresh rate is preferably adjustable to accommodate user preference. The method also includes a step of providing an alarm or alert indicating a new or changed (modified) condition (block 245). This helps prevent administering an old medication order or missing a new order entered after a nursing unit member initiated the medication administration process. In the preferred configuration, the medication administration program product 53 provides automated highlighting of the new and changed orders on the medication administration screen 86 in response to entry of a new or changed order. Further, the medication administration program product 53 can provide for automated printing of new and changed orders on the nursing unit printer 87, either periodically, or in response to entry of a new or changed order, or both.

Also in the preferred configuration, for a normal inpatient scheduled medication administration, the electronic medication administration record 45 data provides the nursing unit members a location to obtain the medication to be administered. As perhaps best shown in FIG. 8B, the medication location can include: floor stock 141, the cart 143; or the automated drug dispensing device 91, or in rare occasions, other medical institution affiliated locations.

For unscheduled medication administrations, such as, for example, emergency medical services or immunization services, a nursing unit member can either contact the pharmacy for medication or, if provided appropriate permissions, can extract the medication directly from floor stock 141 or the automated drug dispensing device 91 (see FIG. 8B). Extraction from the automated drug dispensing device 91 is, however, preferred due to its automated posting of medication removal events.

Figure 23:
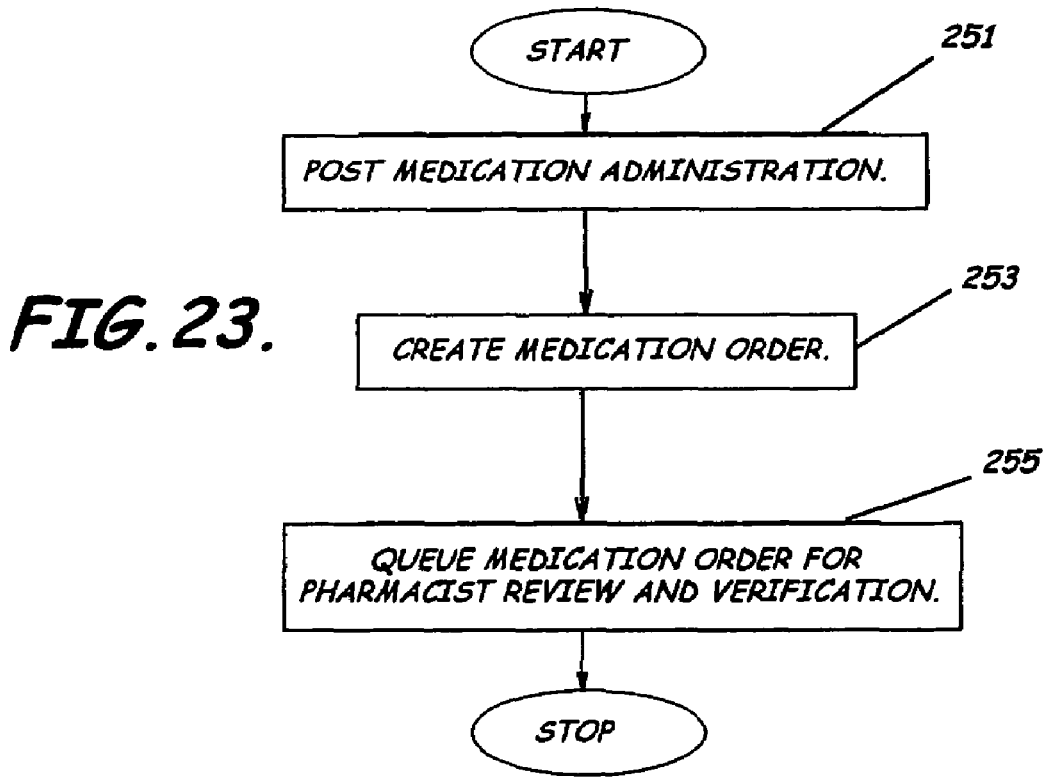
FIG. 23 is a schematic flow diagram of a method to enhance pharmaceutical order entry by medical personnel within a medical institution according to an embodiment of the present invention.

As perhaps best shown in FIG. 23, a method is provided for automated creation of an electronic medication order 57 resulting from an unscheduled administration of medication pursuant to a non-electronic medication order. A nursing unit member obtains the medication, as described above, and administers the medication to the patient. Either prior to or after medication administration, the nursing unit member posts the medication administration (block 251). The medication administration program product 53 includes functionality to perform an automated medication order creation (block 253). The daily created electronic medication order 57 is queued in a special pharmacy working queue for review and verification.

Figure 24:
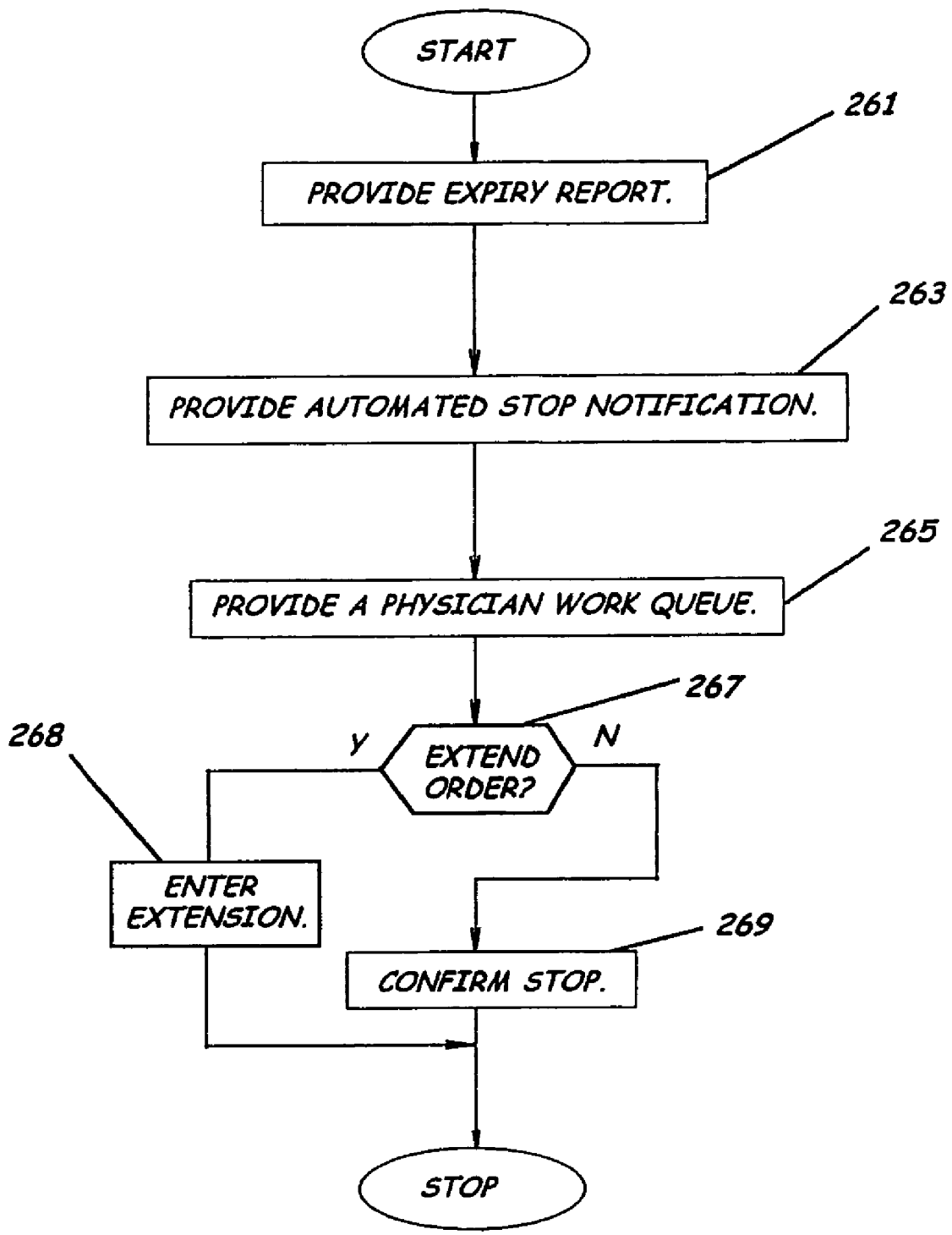
FIG. 24 is a schematic flow diagram of a method to enhance patient medication management by medical personnel within a medical institution according to an embodiment of the present invention.

In an embodiment of the present invention, as perhaps best shown in FIG. 24, a method to enhance patient medication management by medical personnel within a medical institution includes providing an expiry report (block 261) organized by either nursing unit or prescribing physician and listing medication orders for inpatient residents at the medical institution that are about to expire. Further, automated stop notification indicating a medication order that is about to expire can be automatically provided (block 263) to the physician responsible for the medication order scheduled to expire within a preselected time period. The medication administration program product 53 can provide a physician work queue (block 265) requiring the notified physician to positively decide (block 267) to either extend the order (block 268) or confirm the stop (block 269).

It is important to note that while embodiments of the present invention have been described in the context of a fully functional system, those skilled in the art will appreciate that the mechanism of the present invention and/or aspects thereof are capable of being distributed in the form of a computer readable means or medium of instructions in a variety of forms for execution on a processor, processors, or the like, and that the present invention applies equally regardless of the particular type of signal bearing media or means used to actually carry out the distribution. Examples of computer readable media or means include: nonvolatile, hard-coded type media such as read only memories (ROMs) or erasable, electrically programmable read only memories (EEPROMs), recordable type media such as floppy disks, hard disk drives and CD-ROMs, and transmission type media such as digital and analog communication links.

As shown in FIGS. 1-25, embodiments of the present invention also include a computer readable medium or means that is readable by a computer to enhance pharmaceutical order entry and administration by medical personnel and pharmaceutical inventory control within a medical institution. For example, in an embodiment of the present invention, the computer readable medium or means includes a set of instructions that, when executed by the computer, such as, for example, server 35, 37, cause the computer to perform the operation of displaying on a physician video display device 69 (FIG. 3) a graphical user interface including a medication order template or form 55 having database entry fields to allow medication order entry by a physician. The instructions can further perform the operations of: populating the medication order template or form 55 with default values or applying a medication order ingredient template. The medication order template preferably includes default values for a medication route, dose, frequency, and duration. The medication order template can include access to dosing recommendations, such as, for example, minimum and maximum dose, lifetime cumulative dosing, pediatric dosing, neonatal dosing, and geriatric dosing. The medication order template can also include access to standard medication order sets, IV templates, and chemotherapy templates.

The medication order template or form 55 can further provide access to tools for the physician to perform clinical and non-clinical checks. The clinical checking is performed to verify the proposed medication order does not exceed a normally prescribed dose range, interact negatively with other currently prescribed medications, or duplicate another currently active medication order. The non-clinical checking of the proposed medication order is performed to prevent violation of non-clinical medical institution rules, such as, for example, that: the medication order does not duplicate medication against a current medication profile at an ingredient level or at a therapeutic level; the patient is eligible to receive items listed in the medication order, the physician is authorized to prescribe items listed in the medication order to the specific patient; and the medication order does not include items having a quantity or duration exceeding preselected institutional limits.

In response to receipt of an entry in the medication order template or form 55 of a medication order parameter violating a preselected rule, a clinical and/or non-clinical alert is displayed. The instructions are provided to perform the operation of allowing the user to override the alerts, the act of which is termed an intervention. In response to such an intervention, operations performed include automatic intervention logging, and can include the displaying on the graphical user interface a text entry field to provide for entry by the physician of either a reason code or free-form text to describe a reason for the intervention. Further, the operations performed can include an automated update of a respective patient electronic medication administration record 45.

In an embodiment of the present invention, the computer readable medium or means includes a set of instructions that cause the computer to perform the operations of receiving an electronic medication order 57 entered by a physician, responsive to the medication order entry by the physician, and queuing the electronic medication order 57 in a pharmacist working queue. The queued electronic medication order 57 can be displayed on a pharmacy clinical workstation video display device 72 along with any clinical and non-clinical alerts encountered by the physician and any override reasons posted by the physician.

Further, displayed is an entry field providing the pharmacist an ability to override clinical or non-clinical alerts encountered during medication order review and verification. As with the physician, in response to such an intervention by the pharmacist, operations performed include automatic intervention logging, and can include the displaying a text entry field to provide for entry by the pharmacist of either a reason code or free-form text describing a reason for the intervention. Further, the operations performed can include processing the electronic medication order 57 responsive to the review and verification of the medication orders and the clinical and non-clinical checks of the medication orders.

In an embodiment of the present invention, the computer readable medium or means includes a set of instructions that cause the computer to perform the operation of displaying on a video device 89 positioned at a nursing unit located remote from the pharmacy, a graphical user interface including a nursing unit-level electronic medication administration display screen 86 having electronic medication administration record 45 data to allow medication administration entry by an authorized nursing unit member. The instructions can also include those to perform the operation of displaying an electronic medication administration schedule auto-refreshed at a preselected time interval to allow automated screen shifting along a medication administration timeline. The instructions can also include those to perform the operation of providing an alert to the nursing unit indicating a new or changed (modified) electronic medication order 57, in response to entry of the new or changed electronic medication order. This alert can be accomplished, for example, by providing automated highlighting of the new or changed orders on the electronic medication administration display screen 86, or by providing automated printing of the new and changed orders on a nursing unit printer 87.

In an embodiment of the present invention, the computer readable medium or means includes a set of instructions that cause the computer to perform the operations of: receiving a posting of a medication administration for an unscheduled medication order in a graphical user interface preferably displayed on a nursing unit video display device 89; performing an automated creation of an electronic medication order 57 for the administered medication order, in response to the posting of the medication administration; and providing a special queue for a pharmacist to review and verify electronic medication orders 57 created through posting such a medication administration.

In an embodiment of the present invention, the computer readable medium or means includes a set of instructions that cause the computer to perform the operations of: determining if any of a plurality of medication orders 57 for inpatient residents at a medical institution are about to expire within a preselected time period; and providing automated stop notification to a computer 61 associated with a physician responsible for a medication order 57 scheduled to expire within the preselected time period. The instructions can also include those to perform the operation of providing a physician work queue requiring the notified physician to either extend the medication order or confirm the medication order stop time. Advantageously, this requirement helps ensure inpatient medication service is not inadvertently interrupted.

Many modifications and other embodiments of the invention will come to the mind of one skilled in the art having the benefit of the teachings presented in the foregoing descriptions and the associated drawings. Therefore, it is to be understood that the invention is not to be to the illustrated embodiments disclosed, and that modifications and other embodiments are intended to be included within the scope of the appended claims. For example, a limited number of clinically significant rules are incorporated into medication administration program product with flexibility for rule changes. These rules can be expanded to include third party expert rules and a rule editor. Also for example, the system can be easily modified to implement uniquely tailored Care Docs, to replace selected charting forms, to capture medication administration information in addition to charting other pertinent patient care information. In such configuration, medication administration could be captured either directly on the Care Docs or captured using the electronic medication administration record process and subsequently populated on the Care Docs. Also for example, the medication administration program product can be easily implemented to include instructions to perform the operations of capturing, tracking and reporting of adverse drug events. Still further, bar-coding technology can be used to further improve accountability of inventory.

That claimed is:

1. A system positioned within a hospital to enhance pharmaceutical order entry and administration by medical personnel and enhanced pharmaceutical inventory control within a hospital, the system comprising:

a hospital information processing and management computer including memory to store data therein to thereby define a hospital information management server;

a database in communication with the hospital information management server and including a plurality of hospital patient medication profile records and a plurality of electronic medication administration records corresponding to the hospital patient medication profile records for each of a respective plurality of hospital patients, and including patient master data, a hospital drug formulary and a plurality of medication inventory records, each of the plurality of electronic medication administration records providing a single consolidated patient medication administration profile for a corresponding one of the plurality of hospital patients, the single medication profile including both hospital inpatient and outpatient prescribed medications, the electronic medication administration records also indicating unit dose-level dispensing and actual patient consumption verification of individual doses of a prescribed medication for hospital inpatient patients provided to perform clinical checks and non-clinical checks responsive to the hospital drug formulary;

a hospital communications network associated with the hospital in communication with the hospital information management server;

a plurality of hospital physician computers associated with at least one of a plurality of physicians and positioned in the hospital and remote from the hospital information management server, each in communication with the hospital information management server through the hospital communication network and each including memory and software stored in the memory adapted to provide access to the hospital information management server;

a plurality of hospital pharmacy computers associated with at least one of a plurality of pharmacists and positioned in the hospital and remote from the hospital information management server and remote from the plurality of physicians computers, each of the plurality of hospital pharmacy computers in communication with the hospital information management server through the hospital communication network and each of the hospital pharmacy computers including memory and software stored in the memory adapted to provide access to the hospital information management server;

a plurality of hospital nursing unit computers associated with at least one nursing unit member and positioned in the hospital and remote from the hospital information management server and remote from the plurality of hospital pharmacy computers and from the plurality of hospital physicians computers, each of the plurality of hospital nursing unit computers in communication with the hospital information management server through the hospital communication network, and each of the plurality of hospital nursing unit computers including memory and software stored in the memory and adapted to provide access to the hospital information management server;

at least one hospital nursing unit video display in communication with at least one of the plurality of hospital nursing unit computers positioned at a nursing unit, remote from the hospital information management server, and in communication with the hospital information management server through the hospital communication network;

a plurality of automated drug dispensing devices, each of the plurality of drug dispensing devices positioned in the hospital and in communication with the hospital information management server through the hospital communication network to store pharmaceuticals therein and to dispense the pharmaceuticals to one of the plurality of nursing unit members, pharmacists or physicians, each automated drug dispensing device including memory and software stored in the memory to provide access to the hospital information management server, to receive electronic medication administration records, and to provide an interface to modify electronic medication administration records, to thereby provide hospital personnel a tool for recording medication administered to patients, each of the plurality of automated drug dispensing devices also including an override function responsive to entry of hospital patient identification data to enable unscheduled or emergency withdrawal of medication from each of the plurality of automated drug dispensing device and positioned to provide medication removal event data and hospital patient identification data to the hospital information management server, the medication removal event data including medication identification, amount removed, and time of removal; and hospital information management software stored in the memory of the hospital information management server and including medication administration program product comprising a set of instructions that when executed by the hospital information management server cause the hospital information management server to perform a process of integrating medication order, verification and delivery within a hospital and a process of monitoring drug dispensing in the hospital, consisting of:

formatting at least one of the plurality of hospital patient medication profiles stored in the database, responsive to a medical records request from one of the plurality of physicians through one of the plurality of physician computers connected to the hospital information management server through the hospital communications network, to thereby enable a display of a selected hospital patient medication profile record on one of the plurality of physician computers;

formatting the hospital drug formulary stored in the database, responsive to a drug formulary request from one of the plurality of physicians through one of the plurality of physician computers connected to the hospital information management server through the hospital communications network, to thereby enable a display of the hospital drug formulary on one of the plurality of physician computers and allow a one of the plurality of physicians to search an available selection of medication;

creating a medication order entry form, responsive to a medication entry request, for the selected hospital patient medication profile record, the medication order entry form accessible by the one of the plurality of physicians through one of the plurality of physician computers connected through the hospital communications network to the hospital information management server, the medication order entry form allowing one of the plurality of physicians to use one of the plurality of physician computers to perform computerized order entry within the hospital, the medication order entry form having database record input fields that when supplied with input from by one of the plurality of physician computers, communicate the input through the hospital communications network to the hospital information management server;

writing the input supplied from the record input fields to the database to create an electronic medication order accessible by a one of the plurality of pharmacists using one of the plurality of pharmacist computers located within the hospital;

inspecting the electronic medication order, responsive to the receipt of the electronic medication order, with non-clinical checks and clinical checks using at least the hospital patient medication profile records and the single consolidated patient medication administration profile, the non-clinical checks determining at least whether the patient is post-op or pre-op and the clinical checks determining at least whether proper drug dosages for the one of the plurality of patients associated with the single consolidated patient medication administration profile are contained in the electronic medication order;

suspending the electronic medication order, automatically, responsive to at least a determination that the patient associated with the electronic medication order is pre-op or post-op;

notifying, responsive to suspending the electronic medication order, one of the plurality of physicians at one of the plurality of physician computers of the suspension of the medication order to thereby allow one of the plurality of physicians to override the medication order suspension;

creating an electronic medication verification form, responsive to the receipt of the electronic medication order, the electronic medication verification form accessible by one of the plurality of pharmacists through one of the plurality of pharmacist computers within the hospital, the electronic medication verification form allowing computerized input from the one of the plurality of pharmacists at one of the plurality of pharmacist computers to electronically document the verification of electronic medication orders, the electronic medication verification form having database input fields that when supplied with verification input from the plurality of pharmacist computers, communicate the verification input through the hospital communication network to the hospital information management;

writing the verification input into the database to store the electronic medication order with the verification input as a hospital inpatient verified medication order;

formatting the electronic medication administration records and hospital inpatient verified medication order, responsive to a nursing unit member request for access to the database, so that the electronic medication administration records and hospital inpatient verified medication order can be graphically displayed on the nursing unit video display connected to at least one of the plurality of nursing unit computers, the electronic medication administration records being displayed with database input fields so that the nursing unit member can enter medication administration input, and the hospital inpatient verified medication order being provided so that the nursing unit member can review one of the plurality of pharmacists and one of the plurality of physicians notes and special instructions and authenticate the hospital inpatient verified medication order;

updating the electronic medication administration records with the medication administration input, responsive to administration input from the nursing unit member computer or the drug dispensing device, the medication administration input indicating completed administration of the inpatient verified medication order and including the time of medication removal;

creating, automatically, a patient medication order responsive to the override function indicating an unscheduled or emergency medication removal event to thereby reduce incidence of medication dispensing without an electronic medication order; and checking the electronic medication administration records for the plurality of hospital patients to maintain proper medication inventory for the hospital.

2. A system as defined in claim 1, wherein the clinical checks include performing a comparison of the electronic medication order against the hospital patient medication profile both at individual ingredient level and at therapeutic level to verify medication is not being duplicated.

3. A system as defined in claim 1, wherein each automated drug dispensing device maintains an accounting of inventory of medication stored therein to periodically update the medication inventory in the database by connecting to the hospital management server over the hospital communications network.

4. A system as defined in claim 1, wherein each of the plurality of automated drug dispensing devices are positioned to access the medication administration program product to perform an automated posting of a time-of-removal of medication from the respective automated drug dispensing device to a patient associated electronic medication administration record, and wherein each of the plurality of automated drug dispensing devices further comprise a user input device positioned to allow the nursing unit member to post an actual medication administration time to the patient associated electronic medication administration record when so displayed.

5. A system as defined in claim 1, wherein the medication administration program product further includes instructions to perform the operation of:
creating, automatically, the electronic medication order responsive to input of medication administration event data describing an unscheduled medication withdrawal.

6. A system as defined in claim 1, wherein the medication administration program product further includes instructions to perform the operation of:
alerting at least one of the hospital nursing unit computers of a modified medication order responsive to entry of the modified medication order; and
updating electronic medication administration records and hospital inpatient verified medication orders, provided to one of the plurality of nursing unit computers for display on the nursing unit video display, along a medication administration timeline.

7. A system as defined in claim 1, further comprising:
a plurality of claim card printers, each connected to a respective one of the plurality of physicians computers to print a claim card indicating a medication corresponding to the electronic medication order; and
a plurality of nursing unit printers positioned remote from the hospital information management server, each in communication with the hospital information management server through the hospital communication network to print a modified medication order responsive to completion of an entry of the modified medication order.

8. A medication administration program product comprising a set of instructions stored in a memory of a computer defining a hospital information management server that when executed by the hospital information management server cause the hospital information management server to perform a process of integrating medication ordering, verification and delivery within a hospital and a process of monitoring drug dispensing in the hospital, the set of instructions consisting of:
formatting at least one of a plurality of hospital patient medication profiles stored in a database, responsive to a medical records request from one of a plurality of physicians through one of a plurality of physician computers connected to the hospital information management server through a hospital communications network, to thereby enable a display of selected hospital patient medication profile record on one of the plurality of physician computers;

formatting a hospital drug formulary stored in the database, responsive to a drug formulary request from one of the plurality of physicians through one of the plurality of physician computers connected to the hospital information management server through the hospital communications network, to thereby enable a display of the hospital drug formulary on one of the plurality of physician computers and allow a one of the plurality of physicians to search an available selection of medication;

creating a medication order entry form, responsive to a medication entry request, for the selected hospital patient medication profile record, the medication order entry form accessible by the one of the plurality of physicians through one of the plurality of physician computers connected through the hospital communications network to the hospital information management server, the medication order entry form allowing one of the plurality of physicians to use one of the plurality of physician computers to perform computerized order entry within the hospital, the medication order entry form having database record input fields that when supplied with input from by one of the plurality of physician computers, communicate the input through the hospital communications network to the hospital information management server;

writing the input supplied from the record input fields to the database to create an electronic medication order accessible by a one of a plurality of pharmacists using one of a plurality of pharmacist computers located within the hospital and connected to the hospital information management server via the hospital communications network;

inspecting the electronic medication order, responsive to the receipt of the electronic medication order, with non-clinical checks and clinical checks using at least the hospital patient medication profile records and a single consolidated patient medication administration profile, the non-clinical checks determining at least whether a patient associated with the single consolidated patient medication administration profile is post-op or pre-op and the clinical checks determining at least whether proper drug dosages for the patient associated with the single consolidated patient medication administration profile are contained in the electronic medication order;

suspending the electronic medication order, automatically, responsive to at least a determination that the patient associated with the electronic medication order is pre-op or post-op;

notifying, responsive to suspending the electronic medication order, one of the plurality of physicians at one of the plurality of physician computers of the suspension of the medication order to thereby allow one of the plurality of physicians to override the medication order suspension;

creating an electronic medication verification form, responsive to the receipt of the electronic medication order, the electronic medication verification form accessible by one of a plurality of pharmacists through one of a plurality of pharmacist computers within the hospital, the electronic medication verification form allowing computerized input from the one of the plurality of pharmacists at one of the plurality of pharmacist computers to electronically document the verification or electronic medication orders, the electronic medication verification form having database input fields that when supplied with verification input from the plurality of pharmacist computers, communicate the verification input through the hospital communication network to the hospital information management;

writing the verification input into the database to store the electronic medication order with the verification input as a hospital inpatient verified medication order;

formatting the electronic medication administration records and hospital inpatient verified medication order, responsive to a nursing unit member request for access to the database, so that the electronic medication administration records and hospital inpatient verified medication order can be displayed on a nursing unit video display connected to at least one of a plurality of nursing unit computers, the electronic medication administration records being displayed with database input fields so that the nursing unit member can enter medication administration input, and the hospital inpatient verified medication order being provided so that the nursing unit member can review one of the plurality of pharmacists and one of the plurality of physicians notes and special instructions and authenticate the hospital inpatient verified medication order; and updating the electronic medication administration records with the medication administration input, responsive to administration input from the nursing unit member computer or a drug dispensing device, the medication administration input indicating completed administration of the inpatient verified medication order and including the time of medication removal.

9. A medication administration program product as defined in claim 8, the set of instructions further consisting of:
accessing one of the hospital patient medication profile records stored in the database to display the single consolidated patient medication profile including both hospital inpatient and outpatient prescribed medications.

10. A medication administration program product as defined in claim 8, the set of instructions further consisting of:
creating, automatically, a patient medication order responsive to an override function indicating an unscheduled or emergency medication removal event to thereby reduce incidence of medication dispensing without an electronic medication order.

11. A medication administration program product as defined in claim 10,
wherein the medication administration input includes medication identification and amount removed; and
wherein the drug dispensing device further comprises a user input device positioned to allow the nursing unit member to post the time of medication removal to the electronic medication administration record.

12. A medication administration program product as in claim 8, the set of instructions further consisting of:
generating an automated alert indicating a modified medication order responsive to the modified medication order, the automated alert being formatted to enable display on the nursing unit computer.

13. A medication administration program product as defined in claim 8, the set of instructions further consisting of:
formatting the plurality of single consolidated patient medication administration profiles to display on the nursing unit video display as a multi-patient unit dose-level inpatient medication administration schedule auto-refreshed at a preselected time intervals to allow automated screen shifting along a medication administration timeline to thereby provide an automated real-time medication administration schedule.

14. A medication administration program product as defined in claim 8, the set of instructions further consisting of:

formatting at least one of the verified medication orders, responsive to the verified medication order being modified, so that the hospital nursing unit computer and a hospital nursing unit printer cause the hospital nursing unit printer to perform an automated print of the verified medication order report responsive to the modification.

15. A medication administration program product as defined in claim 8, the set of instructions further consisting of:

storing a plurality of medication inventory records in the database associated with the hospital information management server;

initiating automated inventory management transactions including issuing materials from stock and automated depletion of medication inventory from the medication inventory records responsive to the verified medication order; and initiating, automatically, replenishment of pharmaceuticals from external suppliers responsive to the automated depletion of an individual medication below a preselected level of inventory.

16. A computer-implemented method for causing a computer, defining a hospital information management server, to perform a process of electronically integrating medication ordering, verification and delivery within a hospital and a process of monitoring drug dispensing in the hospital the computer-implemented method comprising the steps of:

formatting at least one of a plurality of hospital patient medication profiles stored in a database, responsive to a medical records request from one of a plurality of physicians through one of a plurality of physician computers connected to the hospital information management server through a hospital communications network, to thereby enable a display of selected hospital patient medication profile record on one of the plurality of physician computers;

formatting a hospital drug formulary stored in the database, responsive to a drug formulary request from one of the plurality of physicians through one of the plurality of physician computers connected to the hospital information management server through the hospital communications network, to thereby enable a display of the hospital drug formulary on one of the plurality of physician computers and allow one of the plurality of physicians to search an available selection of medication;

creating a medication order entry form, responsive to a medication entry request, for the selected hospital patient medication profile record, the medication order entry form accessible by the one of the plurality of physicians through one of the plurality of physician computers connected through the hospital communications network to the hospital information management server, the medication order entry form allowing one of the plurality of physicians to use one of the plurality of physician computers to perform computerized order entry within the hospital, the medication order entry form having database record input fields that when supplied with input from by one of the plurality of physician computers, communicate the input through the hospital communications network to the hospital information management server;

writing the input supplied from the record input fields to the database to create an electronic medication order accessible by a one of a plurality of pharmacists using one of a plurality of pharmacist computers located within the hospital and connected to the hospital information management server via the hospital communications network;

inspecting the electronic medication order, responsive to the receipt of the electronic medication order, with non-clinical checks and clinical checks using at least the hospital patient medication profile records and a single consolidated patient medication administration profile, the non-clinical checks determining at least whether a patient associated with the single consolidated patient medication administration profile is post-op or pre-op and the clinical checks determining at least whether proper drug dosages for the patient associated with the single consolidated patient medication administration profile are contained in the electronic medication order;

suspending the electronic medication order, automatically, responsive to at least a determination that the patient associated with the electronic medication order is pre-op or post-op;

notifying, responsive to suspending the electronic medication order, one of the plurality of physicians at one of the plurality of physician computers of the suspension of the medication order to thereby allow one of the plurality of physicians to override the medication order suspension;

creating an electronic medication verification form, responsive to the receipt of the electronic medication order, the electronic medication verification form accessible by one of a plurality of pharmacists through one of a plurality of pharmacist computers within the hospital, the electronic medication verification form allowing computerized input from the one of the plurality of pharmacists at one of the plurality of pharmacist computers to electronically document the verification or electronic medication orders, the electronic medication verification form having database input fields that when supplied with verification input from the plurality of pharmacist computers, communicate the verification input through the hospital communication network to the hospital information management;

writing the verification input into the database to store the electronic medication order with the verification input as a hospital inpatient verified medication order;

formatting the electronic medication administration records and hospital inpatient verified medication order, responsive to a nursing unit member request for access to the database, so that the electronic medication administration records and hospital inpatient verified medication order can be displayed on a nursing unit video display connected to at least one of a plurality of nursing unit computers, the electronic medication administration records being displayed with database input fields so that the nursing unit member can enter medication administration input, and the hospital inpatient verified medication order being provided so that the nursing unit member can review one of the plurality of pharmacists and one of the plurality of physicians notes and special instructions and authenticate the hospital inpatient verified medication order; and updating the electronic medication administration records with the medication administration input, responsive to administration input from the nursing unit member computer or a drug dispensing device, the medication administration input indicating completed administration of the inpatient verified medication order and including the time of medication removal.

17. A computer implemented method as defined in claim 16, wherein the clinical checks verify one of the plurality of physicians is authorized to prescribe each of the items listed in the medication order to the hospital patient associated with the single consolidated patient medication profile; and the medication order does not include items having a quantity or duration exceeding preselected institutional limits.

18. A computer implemented method as defined in claim 16, further including the steps of:
allowing one of the plurality of pharmacists to modify the electronic medication order, responsive to the receipt of the electronic medication verification form, through the database input fields as verification input; and
substituting a drug in the single consolidated patient medication profile, responsive to the receipt of a command from the pharmacist computer authorizing the substitution, the command from the pharmacist computer being contingent upon consultation with one of the plurality of physicians.

19. A computer-implemented method as defined in claim 16, further comprising the steps of:
integrating pre-medication administration patient laboratory results with the medication order prior to the performance of the clinical and non-clinical checks; and
delaying, responsive to the clinical and non-clinical checks, creating at least a portion of the medication order verification form sent to the pharmacist when a predetermined pre-medication administration patient laboratory result criteria is met.

20. A computer-implemented method as defined in claim 16, further comprising a step of:
logging the overrides of the automatic suspensions ordered by one of the plurality of physicians and a hospital nursing unit member.

21. A computer-implemented method as defined in claim 16,
wherein the medication order form includes database input fields that have default values for at least one of a medication route, dose, frequency, and duration;
wherein the medication order form includes database input fields that allow a physician to access to dosing recommendations including at least one of the following: minimum and maximum dose, lifetime cumulative dosing, pediatric dosing, neonatal dosing, and geriatric dosing; and
wherein the medication order form includes database input fields that allow the physician to access at least standard medication order sets, IV templates, and chemotherapy templates.

22. A computer-implemented method as defined in claim 16, wherein the medication order form includes database input fields that include a tool to select and copy a prior active or inactive medication order to function as a template for a current medication order.

23. A computer-implemented method as defined in claim 16, further comprising the step of:
integrating inpatient and outpatient medication orders to provide the single consolidated patient medication profile for each patient of the plurality of hospital patients.

24. A computer-implemented method as defined in claim 16, further comprising the step of:
integrating patient laboratory results with the order template to provide the one of the plurality of physicians with data required to determine proper medication order ingredients.

25. A computer-implemented method as defined in claim 16, wherein the medication order form includes database input fields providing access to a master list of intervention codes grouped by code type; the computer-implement method further comprising the steps of:
logging override by one of the plurality of physicians during computerized medication order entry, overrides by one of the plurality of pharmacists during computerized medication order verification, and interventions by a hospital nursing unit member during at least one of computerized medication order entry and medication administration, to thereby enhance non-compliance tracking.

26. A computer-implemented method as defined in claim 16, wherein the database includes drug restriction data containing restrictions for each medication based on one of the plurality of physicians, specialty, patient, or a combination thereof, doctor-patient familial relationship restriction alerts and patient medication abuse propensity alerts.

27. A computer-implemented method as defined in claim 16, further comprising the steps of:
generating a patient medication stop notification to the hospital nursing unit member, a order by one of the plurality of physicians responsible for a medication order being stopped when within the preselected time; and
alerting one of the plurality of physicians of the medication order being stopped, so that the one of the plurality of physicians can opt to either extend the medication order identified by the patient medication stop notification or confirm the medication order stop time.

28. A computer-implemented method as defined in claim 27, further comprising the steps of:
reporting medication orders for inpatient residents at the hospital that are about to expire within a preselected time period, the report organized by at least one of hospital nursing unit or prescribing one of the plurality of physicians; and
wherein the non-clinical checking includes verifying that at least one day's supply of the ordered unit dose medication is available in inventory for hospital inpatient patients responsive to the medication order entry.

29. A computer-implemented method as defined in claim 16, further comprising the step of:
generating an automated alert indicating a modified medication order responsive to the modified medication order, the automated alert being formatted for display on the nursing unit computer.

30. A computer-implemented method as defined in claim 29, further comprising the step of:
formatting a plurality of the patient medication administration profiles to display on the nursing unit video display a multi-patient unit dose-level inpatient medication administration schedule auto-refreshed at a preselected time interval to allow automated screen shifting along a medication administration timeline to thereby provide an automated real-time medication administration schedule.

31. A computer-implemented method as defined in claim 30, wherein the step of generating the automated alert further comprises the step of:
formatting modified medication orders to display on the nursing unit video display with the modified medication orders highlighted on the administration schedule, responsive to entry of the modified medication order.

32. A computer-implemented method as defined in claim 30, further comprising the step of:

formatting modified medication orders to print on a nursing unit printer responsive to entry of the modified medication order.

33. A computer-implemented method as defined in claim 16, further comprising the steps of:
    posting medication administration event data for an emergency medical services, using a nursing unit computer, the medication order being posted using a graphical user interface; and
    creating, automatically, a hospital patient electronic emergency medical services medication order responsive to the posting of the medication administration event data for the emergency medication administration when the emergency medication administration is performed without a pre-existing electronic medication order.

34. A computer-implemented method as defined in claim 33,
    wherein the step of posting the medication administration for an emergency medication order is performed responsive to a medication removal event data generated responsive to medication removal from the automated drug dispensing device and responsive to hospital nursing unit member input of hospital patient identification data;
    wherein the medication removal event data includes medication identification, amount removed, and time of removal.

35. A computer-implemented method as defined in claim 33, further comprising the steps of:
    posting medication administration event data for an immunization medication order in the graphical user interface responsive to an immunization medication administration; and
    creating a patient electronic immunization medication order including an optional one of the plurality of physicians with a confirmation requirement within a preselected time interval, responsive to posting of the medication administration event data when the immunization medication administration is performed without a pre-existing immunization medical order.

36. A computer-implemented method as defined in claim 16, further comprising the steps of:
    integrating inpatient hospital patient medication and outpatient medication records stored in memory of a computer to provide the single patient medication profile for each patient of a plurality of patients.

37. A computer-implemented method as defined in claim 16, further comprising the step of:
    logging, automatically, any incidence of one of the plurality of physicians overriding an alert.

38. A computer-implemented method as defined in claim 16, further comprising the steps of:
    storing a plurality of medication inventory records stored in the memory of the hospital information management server;
    initiating automated inventory management transactions including issuing materials from stock and automated depletion of medication inventory from the medication inventory records responsive to the verified medication order and
    initiating, automatically, replenishment of pharmaceuticals from external suppliers responsive to the automated depletion of an individual medication below a preselected level of inventory.

* * * * *